(12) United States Patent
Chun et al.

(10) Patent No.: US 11,602,752 B2
(45) Date of Patent: Mar. 14, 2023

(54) APPARATUS FOR AMPLIFICATING NUCLEIC ACID AND FLUORESCENCE-DETECTING DEVICE

(71) Applicant: SEEGENE, INC., Seoul (KR)

(72) Inventors: Jong Yoon Chun, Seoul (KR); Seung Jae Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 1093 days.

(21) Appl. No.: 16/310,527

(22) PCT Filed: Jun. 30, 2017

(86) PCT No.: PCT/KR2017/006964
§ 371 (c)(1),
(2) Date: Dec. 17, 2018

(87) PCT Pub. No.: WO2018/004301
PCT Pub. Date: Jan. 4, 2018

(65) Prior Publication Data
US 2019/0358637 A1    Nov. 28, 2019

Related U.S. Application Data

(60) Provisional application No. 62/399,678, filed on Sep. 26, 2016.

(30) Foreign Application Priority Data

Jun. 30, 2016  (KR) ................. 10-2016-0083111
Nov. 14, 2016  (KR) ................. 10-2016-0151326

(51) Int. Cl.
| | | |
|---|---|---|
| *B01L 7/00* | (2006.01) | |
| *B01L 3/00* | (2006.01) | |
| *B01L 9/00* | (2006.01) | |
| *C12Q 1/6816* | (2018.01) | |
| *C12Q 1/6844* | (2018.01) | |
| *G01N 21/64* | (2006.01) | |
| *G01N 21/03* | (2006.01) | |

(52) U.S. Cl.
CPC ........... *B01L 7/5255* (2013.01); *B01L 3/5082* (2013.01); *B01L 9/523* (2013.01); *C12Q 1/6816* (2013.01); *C12Q 1/6846* (2013.01); *G01N 21/6428* (2013.01); *G01N 21/6452* (2013.01); *B01L 2200/028* (2013.01); *B01L 2300/0609* (2013.01); *B01L 2300/0663* (2013.01); *B01L 2300/0829* (2013.01); *B01L 2300/0832* (2013.01); *B01L 2300/0848* (2013.01); *B01L 2300/0851* (2013.01); *B01L 2300/0858* (2013.01); *B01L 2300/1805* (2013.01); *B01L 2300/1822* (2013.01); *G01N 2021/0382* (2013.01); *G01N 2021/6482* (2013.01)

(58) Field of Classification Search
CPC .................................. B01L 7/00; C12Q 1/686
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 5,210,015 A | 5/1993 | Gelfand et al. |
| 5,538,848 A | 7/1996 | Livak et al. |
| 5,876,930 A | 3/1999 | Livak et al. |
| 5,958,349 A | 9/1999 | Petersen et al. |
| 6,117,635 A | 9/2000 | Nazarenko et al. |
| 6,977,295 B2 | 12/2005 | Belotserkovskii et al. |
| 7,348,141 B2 | 3/2008 | French et al. |
| 7,537,886 B1 | 5/2009 | Nazarenko et al. |
| 8,137,616 B2 | 3/2012 | Sagner et al. |
| 8,236,504 B2 | 8/2012 | Kordunsky et al. |
| 2003/0157563 A1* | 8/2003 | Danssaert ................. B01L 7/52 435/7.1 |
| 2006/0204997 A1* | 9/2006 | Macioszek ........... G01N 35/026 435/6.15 |
| 2008/0268506 A1 | 10/2008 | Cobb |

(Continued)

FOREIGN PATENT DOCUMENTS

| | | |
|---|---|---|
| EP | 1613771 B1 | 3/2012 |
| JP | H07-303704 A | 11/1995 |

(Continued)

OTHER PUBLICATIONS

Jimenez, L., J. of Rapid Methods and Automation in Microbiology 9:263-270 (Year: 2001).*
International Search Report and Written Opinion issued in PCT/KR2017/006964, dated Oct. 23, 2017; ISA/KR.
Saiki et al., Abstract of "Enzymatic Amplification of Beta-Globin Genomic Sequences and Restriction Site Analysis for Diagnosis of Sickle Cell Anemia". Science Magazine, vol. 230, No. 4732, pp. 1350-1354. Retrieved from the Internet URL: http://dx.doi.org/10.1126/science.2999980 (1 page) (Pub date: Jan. 1988).

(Continued)

*Primary Examiner* — Ethan C Whisenant
(74) *Attorney, Agent, or Firm* — Harness, Dickey & Pierce, P.L.C.

(57) ABSTRACT

The present invention relates to an apparatus for performing a nucleic acid amplification reaction and a fluorescence detection device for reaction analysis. The nucleic acid amplification apparatus of the present invention uses a plurality of blocks having different reaction temperatures by independent temperature control and the movement between the blocks is performed along sliding recesses formed in the blocks, enabling to greatly shorten the total amplification time (TAT). In the fluorescence detection device of the present invention, the positions of the light source and the photodetector are very unique for the reaction vessel in which an excitation light is provided and an emission light is generated.

9 Claims, 41 Drawing Sheets

(56) References Cited

U.S. PATENT DOCUMENTS

| | | |
|---|---|---|
| 2014/0093430 A1 | 4/2014 | Chang et al. |
| 2015/0233828 A1* | 8/2015 | Courtney .................. G01J 3/10 250/200 |
| 2017/0008000 A1* | 1/2017 | Kim ..................... C12Q 1/6846 |

FOREIGN PATENT DOCUMENTS

| | | |
|---|---|---|
| JP | H07-303704 A | 11/1995 |
| JP | 2009-232871 A | 10/2009 |
| JP | 2014-030392 A | 2/2014 |
| JP | 2014030392 A | 2/2014 |
| JP | 2015-208232 A | 11/2015 |
| JP | 2015-208232 A | 11/2015 |
| KR | 20150094811 A | 8/2015 |
| WO | WO-2010/140982 A1 | 12/2010 |
| WO | WO-2012096523 A2 | 7/2012 |
| WO | WO-2012134195 A2 | 10/2012 |
| WO | WO-2012150835 A2 | 11/2012 |
| WO | WO-2013115442 A1 | 8/2013 |
| WO | WO-2014104818 A1 | 7/2014 |
| WO | WO-2015/119470 A1 | 8/2015 |

OTHER PUBLICATIONS

Tyagi et al., "Molecular Beacons: Probes that Fluoresce upon Hybridization", Nature Biotechnology, Mar. 1996, vol. 14, pp. 303-308.

Whitcombe et al., "Detection of PCR products using self-probing amplicons and fluorescence", Nature Biotechnology, Aug. 1999, vol. 17, pp. 804-807.

Nazarenko et al., "A closed tube format for amplification and detection of DNA based on energy transfer", Nucleic Acids Research, 1997, vol. 25, No. 12, pp. 2516-2521.

Duck et al., Abstract of "Probe amplifier system based on chimeric cycling oligonucleotides", Biotechniques, Aug. 1990, pp. 142-148.

Sherrill et al., "Nucleic Acid Analysis Using an Expanded Genetic Alphabet to Quench Fluorescence", Journal of the American Chemical Society, 2004, vol. 126, pp. 4550-4556.

French et al., "HyBeacon™ probes: a new tool for DNA sequence detection and allele discrimination", Molecular and Cellular Probes, 2001, vol. 15, pp. 363-374.

Bernard et al., "Homogeneous Amplification and Variant Detection by Fluorescent Hybridization Probes", Clinical Chemistry, 2000, vol. 46, No. 2, pp. 147-148.

* cited by examiner

SIDE

FRONT

PLAN

SIDE

FRONT

PLAN

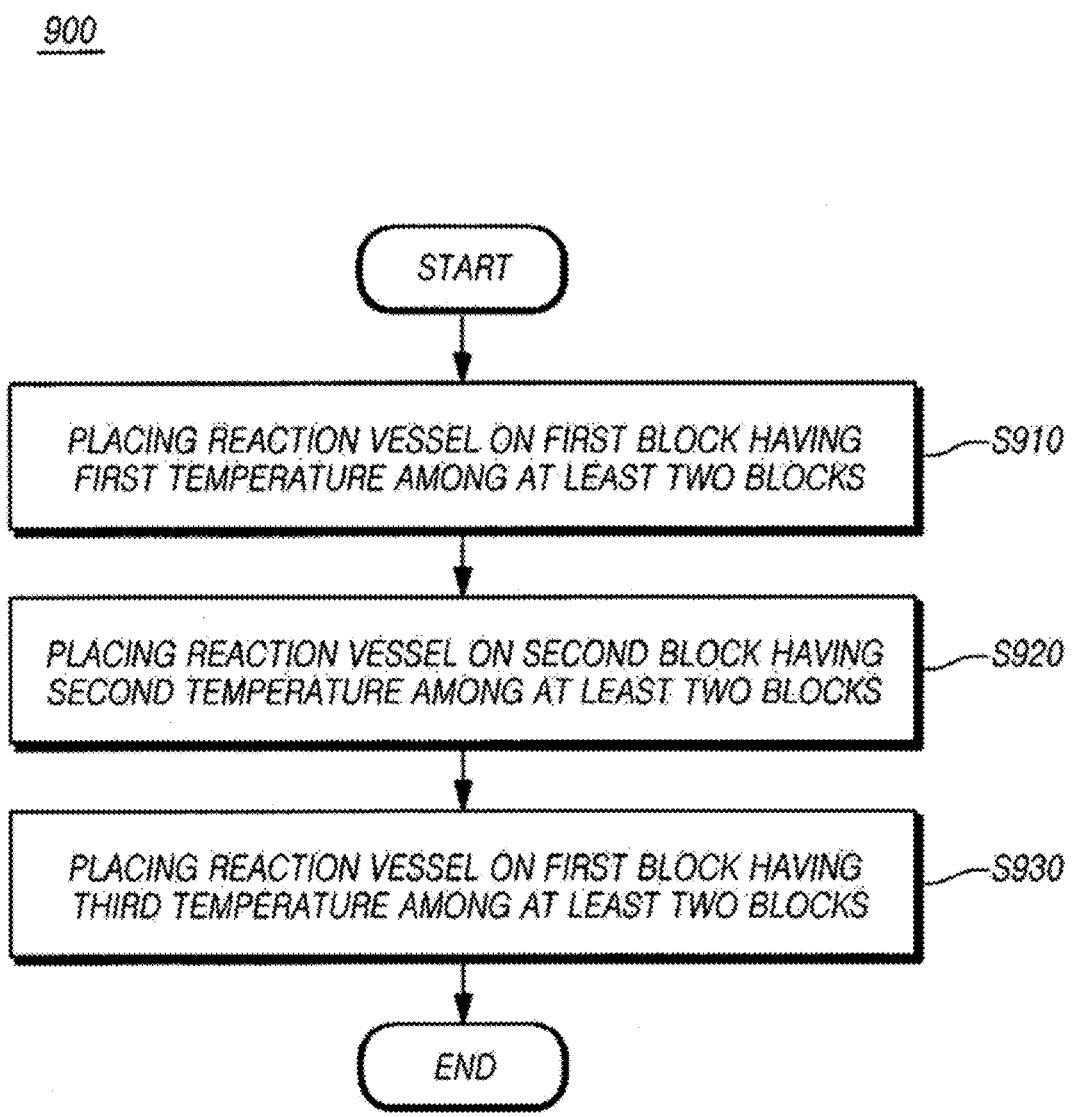

APPARATUS FOR AMPLIFICATING NUCLEIC ACID AND FLUORESCENCE-DETECTING DEVICE

CROSS-REFERENCE TO RELATED APPLICATIONS

This application is a U.S. National Phase Application under 35 U.S.C. 371 of International Application No. PCT/KR2017/006964, filed on Jun. 30, 2017, which claims the benefit of Korean Patent Application No. 2016-0083111, filed on Jun. 30, 2016, and Korean Patent Application No. 2016-0151326, filed on Nov. 14, 2016 in the Korean Intellectual Property Office, and U.S. Provisional Patent Application No. 62/399,678, filed on Sep. 26, 2016 in the United States Patent and Trademark Office, the disclosures of which are incorporated herein by reference.

BACKGROUND OF THE INVENTION

Field of the Invention

The present invention relates to a nucleic acid amplification technique for amplifying a nucleic acid molecule.

Description of the Related Art

The most widely used nucleic acid amplification reaction, which is well-known as a Polymerase Chain Reaction (PCR), repeats a cyclic process which includes denaturation of a double-stranded DNA, annealing of an oligonucleotide primer with a denatured DNA template, and extension of the primer by a DNA polymerase (U.S. Pat. Nos. 4,683,195, 4,683,202, and 4,800,159 of Mullis et al.; Saiki et al., (1985) Science 230, 1350-1354).

Recently, various nucleic acid amplification apparatuses have been developed for carrying out a nucleic acid amplification reaction. An example of a nucleic acid amplification apparatus is configured to mount a vessel including a sample solution including a template nucleic acid in one reaction chamber, and to perform a nucleic acid amplification reaction by repeatedly heating and cooling the vessel.

However, since the conventional apparatuses for a nucleic acid amplification use one reaction chamber, there are problems in that it is necessary to include a complicated structure for an accurate temperature control over the overall area of the reaction chamber. Furthermore, the conventional apparatuses performs the repeated heating and cooling of one reaction chamber, and such operation manner is considered a main cause to make the entire time for conducting the nucleic acid amplification reaction much longer.

There have been reported various fluorescence detection apparatuses and devices for reaction analysis, in particular apparatuses and devices for analyzing a nucleic acid amplification reaction in a real-time manner.

For example, the Biorad's real-time PCR apparatus CFX96 consists of two devices: a thermal cycler configured to conduct a nucleic acid amplification reaction in the lower part of the apparatus and an optical device configured to analyze (or monitor) the amplification reaction in real time at the upper part of the apparatus.

In the CFX 96 apparatus, the nucleic acid amplification reaction of a sample is achieved through temperature control of a single heat block fixed to a body of a thermal cycler. The optical device at the top of the CFX96 apparatus includes an optical shuttle with six light sources and six detectors, which moves in the X-axis and Y-axis to detect fluorescence generated in the nucleic acid amplification reaction in real time (U.S. Pat. No. 8,236,504). FIG. 1 shows the optical shuttle (i.e., an optical module 10) of the CFX96 apparatus. In FIG. 1, a reaction vessel 13 is located in a sample well 14 configured in a heat block 15, and a nucleic acid amplification reaction proceeds in the reaction vessel 13. Fluorescence generated from the reaction vessel 13 is measured at a predetermined time interval while the nucleic acid amplification reaction is proceeding. In fluorescence measurement, excitation light 22 generated from a light source 11, passes through a filter 17 and lens 18, and is then provided to the reaction vessel 13. Emission light 23 emitted from a reaction mixture in the reaction vessel 13 is guided by a beam splitter 21 to a photodiode (i.e., photodetector 12), passes through a filter 19 and lens 20, and is then detected at the photodiode 12.

Where a light source is located above a reaction vessel, such as the optical shuttle of the CFX 96, precise positioning of the light source is required because the excitation light has to pass through an upper part of the reaction vessel with relatively narrow area. In addition, the conventional technologies have difficulty in applying excitation light with the same light path length to all reaction tubes. Furthermore, where the photodetector is located above the reaction vessel, such as the optical shuttle of the CFX96, precise positioning of the photodetector is required and it will be difficult to detect the emission light with the same light path length from all reaction tubes.

Most of real-time nucleic acid amplification apparatuses, including the CFX96 apparatus, require precise positioning of sophisticated light sources and photodetectors.

As another real-time nucleic acid amplification apparatus, AB7500 (Thermo Fisher Scientific, Inc.) is an apparatus in which a single light source irradiates a reaction plate through five types of filters placed above a reaction plate in a circular disc shape and the fluorescence emitted is detected by a photodetector above the reaction plate. However, the AB7500 apparatus has serious drawbacks in the senses that the light from the light source is spread in a circle and thus the edge of the reaction plate in rectangular shape is very likely not to be irradiated, whereby the fluorescence detection is uneven over all areas of the reaction plate.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

To be free from shortcomings of the conventional technologies described above, the present invention provides an apparatus for a nucleic acid amplification reaction in which a temperature control of heating blocks is more conveniently conducted and a time for conducting an entire nucleic acid amplification reaction becomes much shorter.

In addition, the present invention provides a fluorescence detection device in which a light source and a photodetector are elaborately arranged and the excitation of a reaction mixture by excitation light and fluorescence detection of emission light are carried out in significantly improved manner, thereby being capable of solving the problems and limitations of conventional technologies (e.g., non-uniformity of excitation light path length and emission light path length, needs of a beam splitter and complex configuration).

In one aspect of this invention, there is provided an apparatus for performing a nucleic acid amplification reaction comprising: (i) a main body; (ii) at least two blocks positioned on the main body and each having at least one sliding recess formed such that when a reaction vessel is inserted into a sliding recess, the reaction vessel is capable of being moved along sliding recesses between the at least two blocks, the at least two blocks being configured to be subjected to independent temperature control; and (iii) a moving module configured to move the at least two blocks and/or the reaction vessel such that the reaction vessel is moved along the sliding recesses in relative to the at least two blocks.

In another aspect of this invention, there is provided a fluorescence detection device for reaction analysis comprising at least one optical module comprising: (a) a support structure; (b) an accommodation hole for a photodetector formed in one plane of the support structure, and having an optically open structure toward a location in which a reaction vessel is positioned; and (c) an optical unit comprising: (c-1) a light source for providing excitation light; and (c-2) a photodetector configured to be positioned in the accommodation hole for the photodetector such that the photodetector is arranged in an emission light path from the reaction vessel.

In another aspect of this invention, there is provided a reaction tube for a nucleic acid amplification comprising: (i) an upper part having a hollow-cylindrical shape or hollow-polygonal column shape; and (ii) a lower part configured to accommodate a reaction mixture for amplifying a nucleic acid, and fluidically connected to the upper part, the lower part having a flattened shape including front and rear planes each having a flat face, side planes narrower than the front plane, and a bottom plane, wherein the flat face of each of the front and rear planes is thermoconductively in contact with a block used for the nucleic acid amplification reaction.

In another aspect of this invention, there is provided a reaction vessel for a nucleic acid amplification comprising two or more reaction containers. Each of the reaction containers comprises an upper part and a lower part configured to accommodate a reaction mixture for amplifying a nucleic acid. The upper part has a hollow-cylindrical shape or hollow-polygonal column shape. The lower part is positioned below the upper part, and is fluidically connected to the upper part. The lower part has a flattened shape, including (i) front and rear planes each having a flat face, (ii) side planes that are narrower than the front plane, and (iii) a bottom plane. Here, the flat face of each of the front and rear planes is thermoconductively in contacted with a block used for the nucleic acid amplification reaction.

In still another aspect of the invention, there is provided a method for a nucleic acid amplification, comprising: (i) placing at a first time a reaction vessel containing a reaction mixture on a first block having a first temperature among at least two blocks such that the reaction vessel is inserted into a sliding recess of the first block; wherein the at least two blocks have at least one sliding recess formed such that when the reaction vessel is inserted into a sliding recess, the reaction vessel is capable of being moved along sliding recesses between the at least two blocks; wherein the at least two blocks are configured to be subjected to independent temperature control; and (ii) placing at a second time the reaction vessel on a second block having a second temperature such that the reaction vessel is inserted into a sliding recess of the second block.

The nucleic acid amplification apparatus of the present invention uses a plurality of blocks having different reaction temperatures by independent temperature control and the movement between the blocks is performed along sliding recesses formed in the blocks, enabling to greatly shorten the total amplification time (TAT).

In the fluorescence detection device of the present invention, the positions of the light source and the photodetector are very unique for the reaction vessel in which an excitation light is provided and an emission light is generated.

BRIEF DESCRIPTION OF THE DRAWINGS

FIG. 36 is a flowchart illustrating a method for a nucleic acid amplification according to yet another embodiment.

DETAILED DESCRIPTION OF THIS INVENTION

Figure 1:
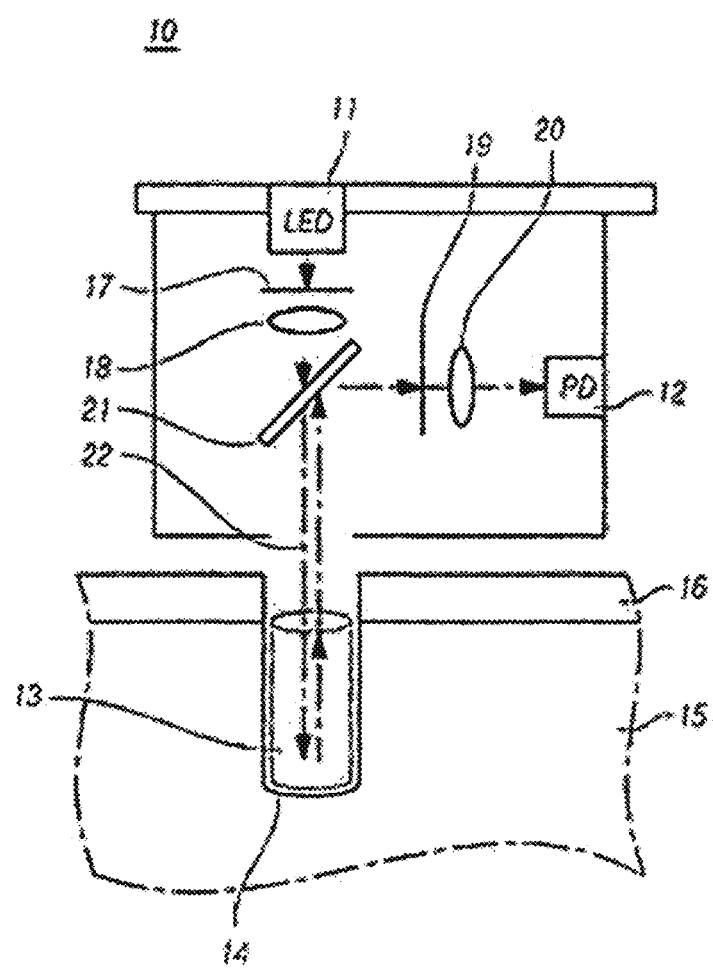
FIG. 1 shows an optical module of a conventional apparatus for performing a nucleic acid amplification reaction.

Hereinafter, aspects of the exemplary embodiments will be described in detail with reference to the accompanying drawings. In adding reference numerals to elements in each drawing, the same elements will be designated by the same reference numerals, if possible, although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b), (i), (ii) or the like may be used herein when describing components of the present invention. These terms are merely used to distinguish one structural element from other structural elements, and a property, an order, a sequence and the like of a corresponding structural element are not limited by the term. It should be noted that if it is described in the specification that one component is "connected," "coupled" or "joined" to another component, a third component may be "connected," "coupled," and "joined" between the first and second components, although the first component may be directly connected, coupled or joined to the second component.

Figure 2:
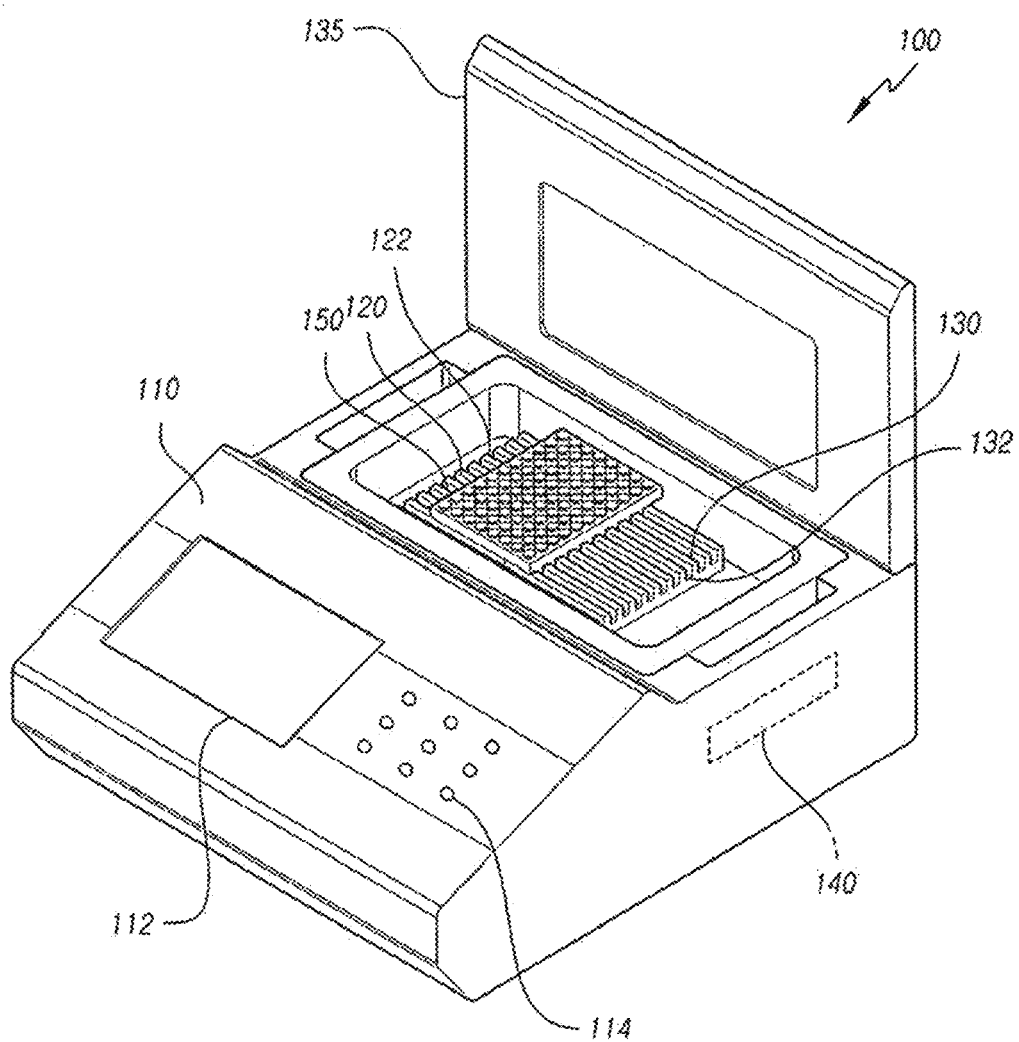
FIG. 2 is a perspective view illustrating a nucleic acid amplification apparatus according to one embodiment.

FIG. 2 is a perspective view illustrating an apparatus for a nucleic acid amplification reaction according to one embodiment.

Referring to FIG. 2, an apparatus 100 for a nucleic acid amplification reaction according to one embodiment refers to an apparatus that conducts a nucleic acid amplification reaction to amplify a nucleic acid having a specific nucleotide sequence. In particular, the apparatus for a nucleic acid amplification reaction refers to an apparatus that conducts a nucleic acid amplification reaction through a temperature control.

For example, in order to amplify a deoxyribonucleic acid (DNA) having a specific nucleotide sequence, the apparatus for a nucleic acid amplification reaction may perform a denaturing step, an annealing step, and an extension (or amplification) step.

The denaturing step refers to a step of separating a double-stranded DNA into single-stranded DNAs by heating a solution containing a specimen including the double-stranded template DNA and a reagent to a specific temperature (e.g., 95° C.). The annealing step refers to a step of forming a partial DNA-primer hybrids by providing a oligonucleotide primer having a nucleotide sequence complementary to a nucleotide sequence of a nucleic acid to be amplified, and cooling the provided primer together with the separated single-stranded DNAs to a specific temperature (e.g., 60° C.) so that the primer hybridizes to the specific nucleotide sequence of the single-stranded DNAs. The extension step performs a step of forming a double-stranded DNA based on the primer of the partial DNA-primer hybrids using a DNA polymerase by maintaining the solution at a specific temperature (e.g., 72° C.) after the annealing step.

When the above-described three steps are repeated, for example, 10 to 50 times, the DNA having a specific nucleotide sequence may be exponentially amplified. Alternatively, the apparatus 100 for a nucleic acid amplification reaction may perform the annealing step and the extension step simultaneously. In such a case, the apparatus 100 for a nucleic acid amplification reaction may perform two steps including a denaturing step and an annealing/extension step so as to complete a first cycle.

Referring to FIG. 2, the apparatus 100 for a nucleic acid amplification reaction according to one embodiment of the present invention may comprise a main body 110, at least two blocks 120, 130, and a moving module 140.

The main body 110 forms the body of the apparatus 100 for a nucleic acid amplification reaction. The main body 110 may comprise a display device 112 configured to display an image and information and an input device 114 configured to input various pieces of information.

The blocks 120, 130 are positioned in the main body 110. The main body 110 may comprise a separate space configured to accommodate the blocks 120, 130. The main body 110 may comprise a cover 135 configured to open/close the separate space configured to accommodate the blocks 120, 130.

The terms "block" and "heat block" used herein will be used interchangeably with no intended distinction between these terms.

Each of the blocks 120, 130 has at least one sliding recess 122, 132 formed such that when a reaction vessel 150 is inserted into a sliding recess 122, 132, the reaction vessel is capable of being moved along sliding recesses between the at least two blocks. According to one embodiment, it is a portion of the reaction vessel that is inserted into the sliding recess. The portion of the reaction vessel which is inserted into the sliding recess on the blocks is the lower part of the reaction vessel, and comprises at least a portion that includes a reaction mixture for a nucleic acid amplification.

In the present invention, the reaction vessel refers to a closed space in which a reaction is conducted. The reaction vessel comprise one reaction container or two or more reaction containers. The reaction container may refer to a unit that is capable of accommodating a reactant (e.g., a reaction solution or a reaction mixture). Each of a test tube, a PCR tube, a strip tube, and a multi-well PCR plate may be an implemented example of the reaction vessel that comprises one reaction container or two or more reaction containers.

According to one embodiment, the whole or the greater part, or a part of the reaction vessel 150 may be inserted into the sliding recess to be movable. In this case, the shape of the reaction vessel 150 or the shape of the sliding recess is determined such that the whole or the greater part, or a part of the reaction vessel 150 is inserted into the sliding recess (e.g., the whole or the greater part as well as the lower part of the reaction container has a flat face).

In addition, the temperatures of the blocks 120, 130 may be controlled independently.

The moving module 140 may be positioned in the main body 110. The moving module 140 may be configured to move at least two blocks 120, 130 and/or the reaction vessel 150 such that the reaction vessel 150 is moved along the sliding recesses 122, 132 in relative to the at least two blocks. The moving module 140 may be positioned on at least one of the lateral side, the front side, the rear side, the top side, and the bottom side of any of the blocks 120, 130 or the reaction vessel 150 in the space within the main body 110.

The apparatus 100 for a nucleic acid amplification reaction according to the present invention may comprise a processor configured to control components elements inside the apparatus to conduct a reaction depending on an input reaction condition, or configured to display a progress of the reaction.

The apparatus 100 for a nucleic acid amplification reaction according to one embodiment of the present invention may be connected to a computer device via a cable or wirelessly.

FIGS. 3A to 3C are views illustrating forms of at least two blocks, respectively.

Referring to FIGS. 3A to 3C, at least two blocks 120, 130 may be physically connected to each other or physically separated from each other.

While FIG. 3A illustrates at least two blocks 120, 130 that are physically connected to each other, the blocks 120, 130 may be separated from each other in terms of thermal conduction so that the temperatures of the blocks may be capable of being controlled independently. For example, the two blocks 120, 130 may comprise two sections 120a, 130a, which are physically connected to each other, but are separated from each other in terms of thermal conduction. The portion where the two blocks 120, 130 are physically connected to each other may comprise an insulation material which prevents thermal conduction.

As illustrated in FIGS. 3B and 3C, the at least two blocks 120, 130 that are physically separated from each other, and separated from each other in terms of thermal conduction so that the temperatures of the blocks may be controlled independently. For example, the two blocks 120, 130 may comprise two sections 120a, 130a, which are physically separated from each other and separated from each other in terms of thermal conduction. As illustrated in FIG. 3C, a region 150a in which the reaction vessel 150 is able to be positioned may exist between two sections 120a, 130a of the two blocks 120, 130.

Heat transfer modules 160, 170 may be positioned correspondiing to two sections 120a, 130a so as to independently supply heat or to independently absorb heat. The two blocks 120, 130 are controlled independently to have different temperatures by the heat transfer modules 160, 170, and the temperatures of each of the two blocks 120, 130 may be converted to two or more different temperatures.

According to one embodiment of the present invention, the heat transfer modules 160, 170 may be physically connected to, or separated from, each other.

Hereinafter, the blocks including at least two sections 120a, 130a, which are physically separated from each other or separated from each other in terms of thermal conduction even if the at least two sections 120a, 130a are physically connected to each other, are defined as at least two blocks 120, 130.

According to one embodiment of the present invention, the apparatus 100 for a nucleic acid amplification reaction comprises two blocks 120, 130 that comprise two sections, which are physically separated from each other or separated from each other in terms of thermal conduction even if the two sections are physically connected to each other. According to another embodiment of the present invention, the apparatus 100 for a nucleic acid amplification reaction comprises three blocks that comprise three sections that are physically separated from each other or separated from each other in terms of thermal conduction even if the three sections are physically connected to each other.

Each of the blocks 120, 130 may comprise a plurality of sliding recesses. Because the sliding recesses are formed in a plural number, reactions of a number of samples may be conducted simultaneously. Each of the blocks 120, 130 may comprise one or more, two or more, three or more, four or more, six or more, or eight or more sliding recesses. Each of the blocks 120, 130 may comprise 30 or less, 25 or less, 20 or less, 15 or less, or 12 or less sliding recesses. The number and interval of sliding recess formed in the blocks 120, 130 may be equal to each other. By forming the sliding recess with the same number and interval in the blocks 120, 130, when the reaction vessel is moved from one block to another block, the reaction vessel may be moved in an inserted state.

When a plurality of sliding recesses is formed in the plurality of blocks 120, 130, the plurality of sliding recesses formed in one block is controlled together in terms of thermal conductance. In other words, a plurality of sliding recesses formed in one block may be subjected to a temperature control by one heat transfer module 360, or by a plurality of heat transfer modules 360, but, in any case, the plurality of sliding recesses formed in one block is controlled to have the same temperature.

When a plurality of blocks is arranged, the side faces of the blocks at both ends where the movement of the reaction vessel is not permitted are formed such that the sliding recess is blocked.

The width and shape of the sliding recess 122 may be determined in consideration of the reaction vessel 150 to be inserted (in particular, the lower part thereof). Specifically, the width of sliding recess 122 may have a dimension sufficient to accommodate the side width W1 of the lower part of reaction vessel 150 so as to allow the reaction vessel to be moved along the sliding recess 122, and to allow sliding recess 122 to be in contact to the reaction vessel 150 in terms of thermal conductance. The depth of the sliding recess 122 may have a dimension sufficient to accommodates the whole or a portion of the vertical length of the reaction vessel 150 and allows the reaction vessel 150 to be moved along the sliding vessel. The sliding recess 122 is not particularly limited in terms of shape, but may have a straight line or a curve line shape so as to allow the reaction vessel 150 to be moved linearly or curvedly along the sliding recess 122. Specifically, the sliding recess 122 has a straight line shape so as to allow the reaction vessel 150 to be moved linearly along the sliding recess 122.

Specifically, the width of each sliding recess 122 may be 1 mm or more and 7 mm or less or 5 mm or less based on the bottom plane of the sliding recess 122. Specifically, the width of each sliding recess 122 may be 1 mm or more and 7 mm or less based on the bottom plane of the sliding recess 122. In addition, the depth of each sliding recess 122 may be 2 mm or more or 3 mm or more, and 15 mm or less, 10 mm or less, or 5 mm or less. Specifically, the depth of each sliding recess 122 may be 3-15 mm or 3-10 mm.

According to one embodiment, the blocks may be manufactured using a material that has an excellent thermal capacity and thermal conductivity, etc. The blocks may be made of a metal or a metal alloy (e.g., iron, copper, aluminum, gold, silver, or an alloy including any of them).

Figure 4:
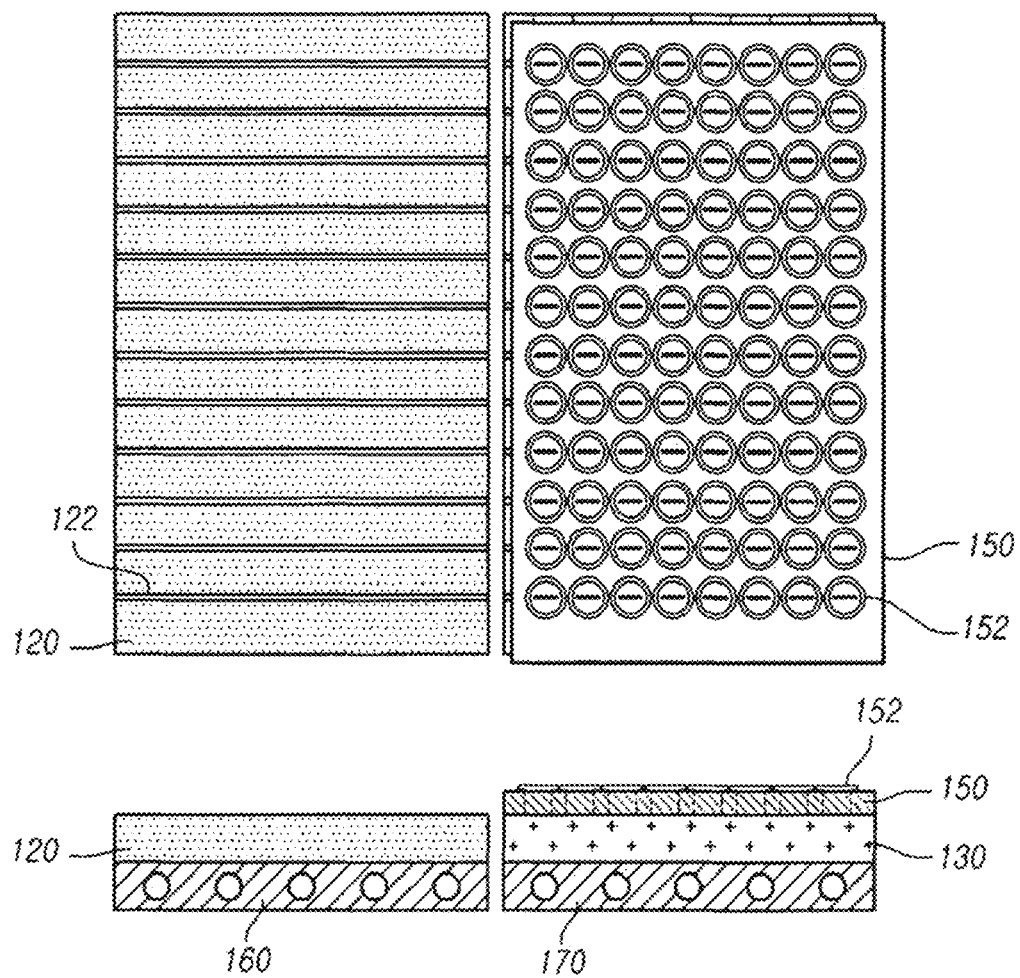
FIGS. 4 and 5 are views illustrating operations in which a reaction vessel is moved along sliding recesses of the blocks.
Figure 5:
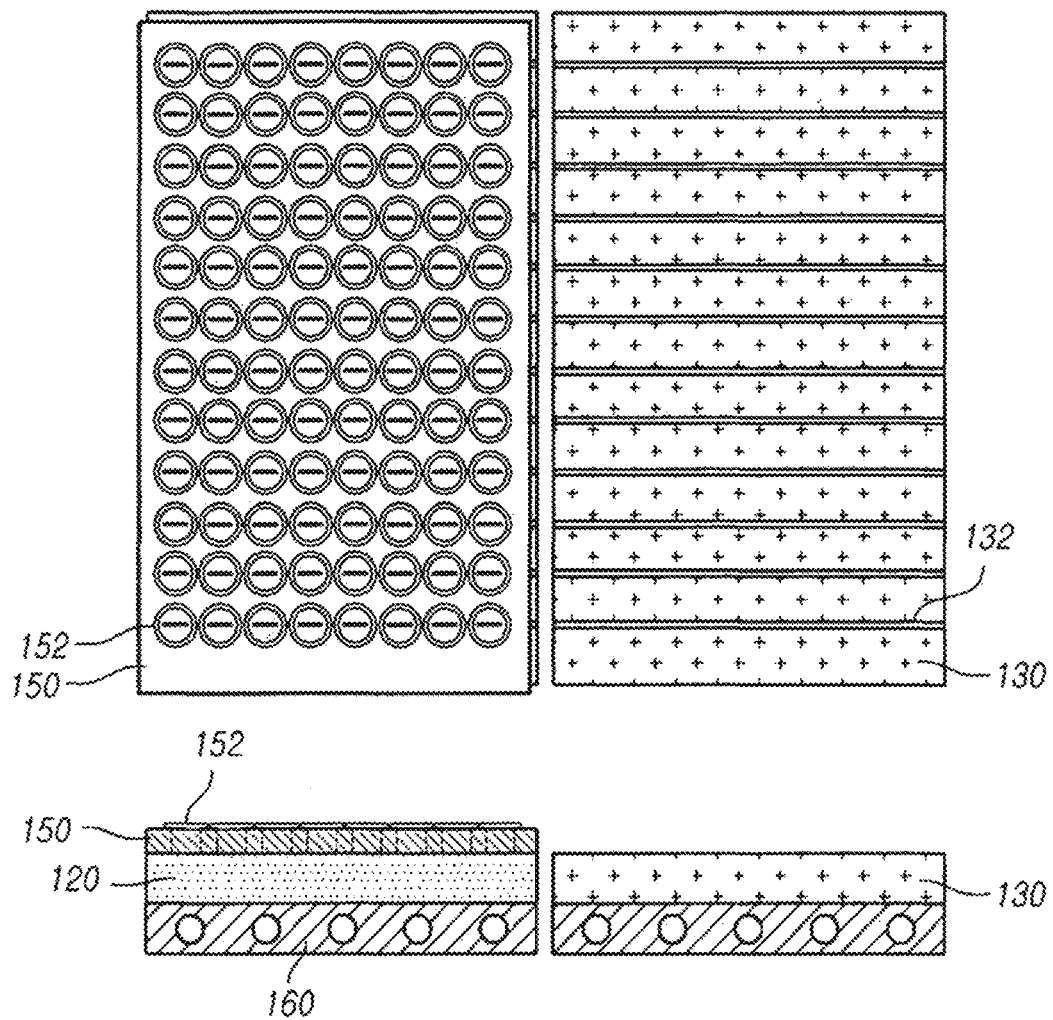

FIGS. 4 and 5 are views illustrating operations in which a reaction vessel is moved along sliding recesses of the blocks.

When the two blocks 120, 130 are positioned adjacent to each other as illustrated in FIG. 3A or FIG. 3B, in the apparatus 100 for a nucleic acid amplification reaction, the reaction vessel 150 is positioned on one of the two blocks 120 and 130 as illustrated in FIG. 4, and after a certain period of time, the reaction vessel 150 is positioned on the other one 130 of the two blocks 120, 130 as illustrated in FIG. 5.

In other words, among at least two blocks 120, 130 respectively having at least one sliding recess 122, 132 formed, at a first time, a reaction vessel 150 in which a reaction mixture is contained is positioned on one block 130 having a first temperature such that the reaction vessel 150 is inserted into a sliding recess 132 of the one block 130. At a second time after a predetermined length of time from the first time, the reaction vessel 150 may be positioned on another block 120 having a second temperature among the blocks 120, 130 such that the reaction vessel 150 is inserted into a sliding recess 122 of the another block 120.

In addition, at the second time, the temperature of the one block 130 is changed to a third temperature, and at a third time, and the reaction vessel 150 may be positioned on the one block 130 having a third temperature such that a portion of the reaction vessel 150 is inserted into the sliding recess 132 of the one block 130.

At this time, the reaction vessel 150 may be moved along sliding recesses 122, 132 of the blocks 120, 130 to any one of the two blocks 120, 130.

Figure 6:
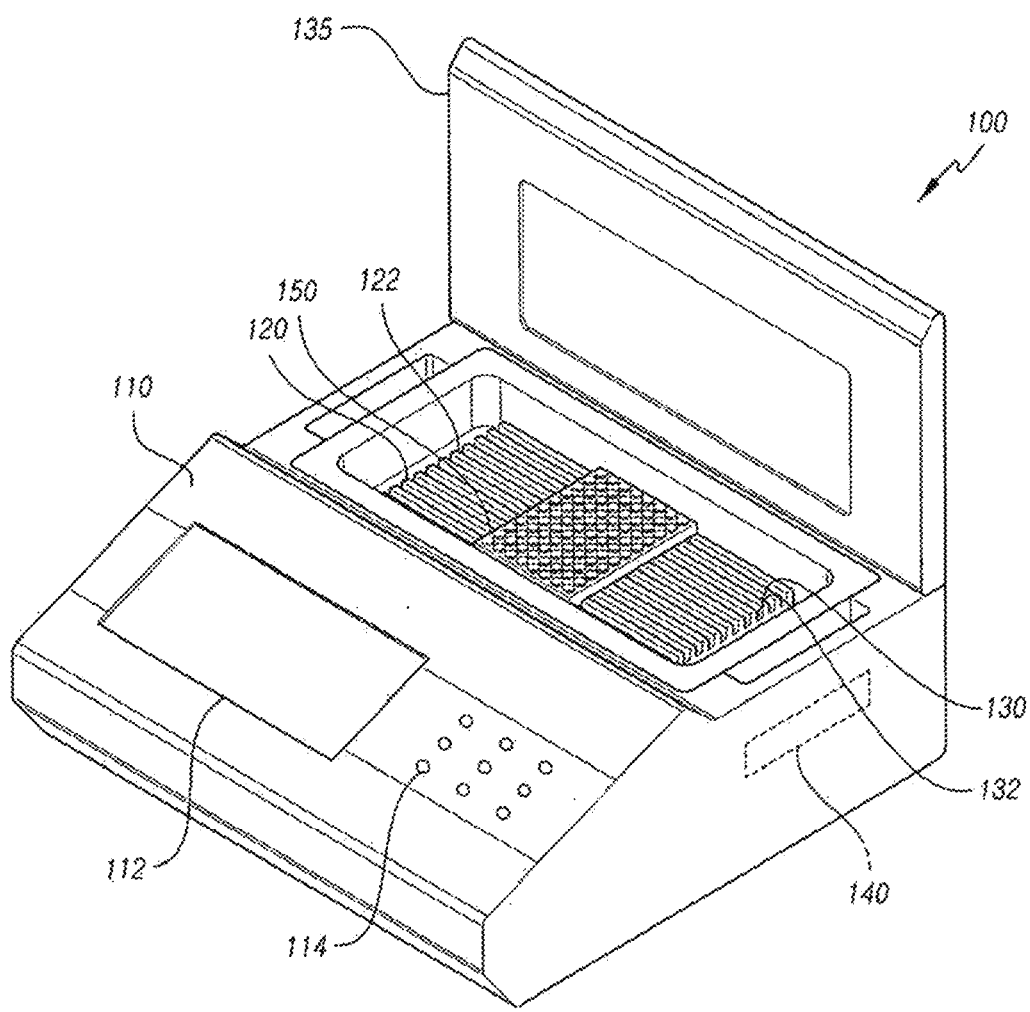
FIG. 6 is a perspective view illustrating an apparatus for a nucleic acid amplification reaction in which the two blocks of FIG. 3C are separated from each other with a specific region being interposed therebetween.
Figure 7:
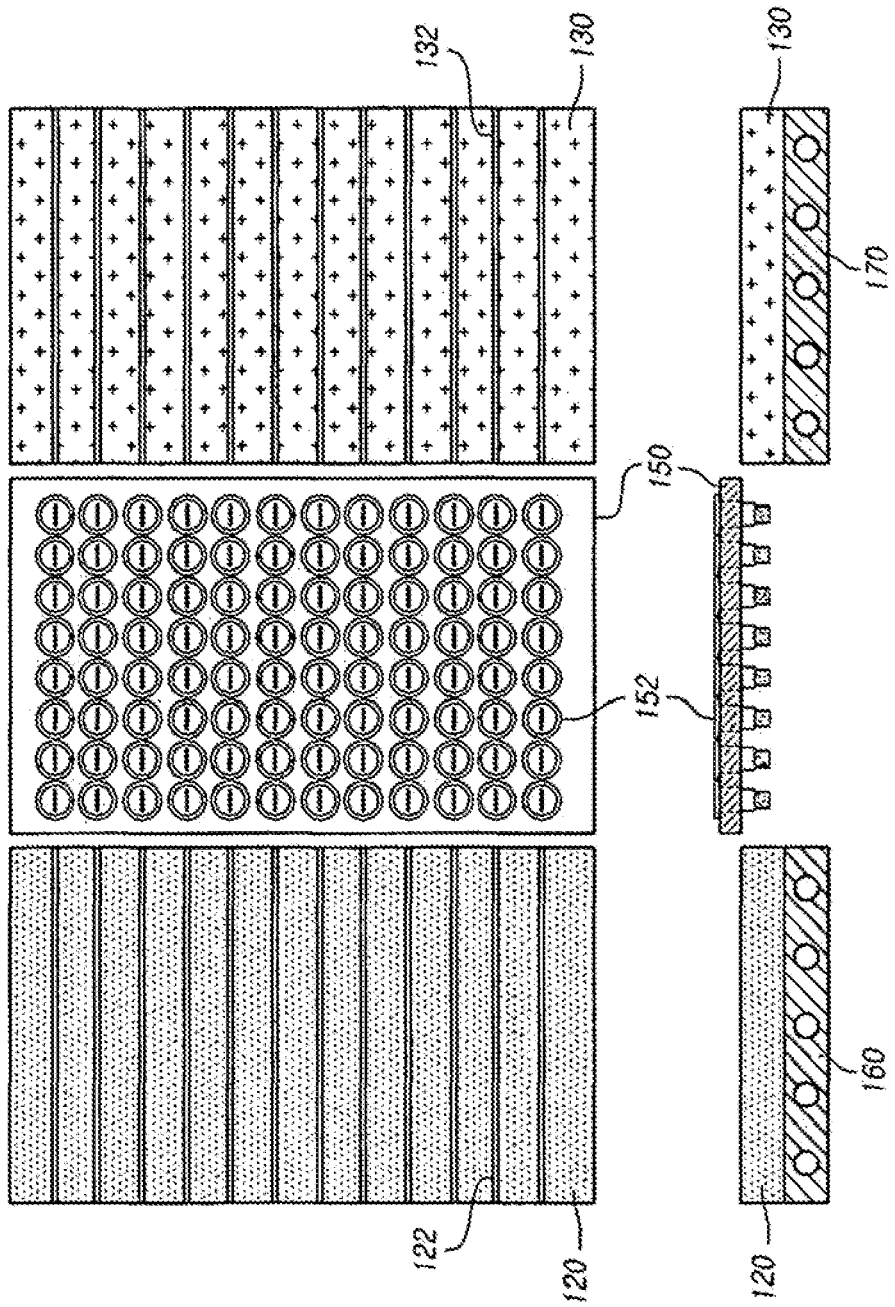
FIG. 7 is a view illustrating operations in which a reaction vessel is stationary and one of the blocks is moved.

FIG. 6 is a perspective view illustrating an apparatus for a nucleic acid amplification reaction in which the two blocks of FIG. 3C are separated from each other with a specific region being interposed therebetween. FIG. 7 is a view illustrating operations in which the reaction vessel is stationary and at least one of the blocks is moved.

Referring to FIGS. 6 and 7, the reaction vessel 150 is positioned between two blocks 120, 130 in the apparatus 100 for a nucleic acid amplification reaction, and heat transfer modules 160, 170 each configured to independently supply heat or absorb heat may be positioned for each of the two blocks 120, 130. Two blocks 120, 130 are independently controlled to have different temperatures by the heat transfer modules 160, 170, and the temperatures of each of the blocks 120, 130 may be converted to two or more different temperatures.

At this time, the reaction vessel is stationary, and the at least two blocks 120, 130 are moved by the moving module such that the reaction vessel 150 may be relatively moved to one of the two blocks 120, 130. In other words, the moving module is configured such that at least one of the at least two blocks is moved along the reaction vessel inserted so as to allow the reaction vessel to be positioned in one of the at least two blocks. Specifically, the two blocks 120, 130 are moved along an inserted contact surface such that the reaction vessel 150 may be positioned in one of the two blocks 120, 130; wherein the inserted contact surface means a contact surface which is formed between the block and the reaction vessel when the reaction vessel is inserted into the sliding recess.

The reaction vessel 150 may be fixed by being connected to a reaction vessel fixing unit (not illustrated), which is fixed to at least one face within a block reception space. The reaction vessel 150 may be fixed by being placed on, or inserted into, the reaction vessel fixing unit.

As found in FIGS. 4, 5, and 7, the reaction vessel 150 may be moved along the sliding recess 122, 132 of two blocks 120, 130 to be repeatedly positioned on one of the two blocks 120, 130, which are controlled independently to have different temperatures, and thus, three steps, which are composed of a denaturing step, an annealing step, and an extending step, or two steps, which are composed of a denaturing step and an annealing/extending step, may be repeated, for example, for 10 to 50 times so that a DNA having a specific nucleotide sequence can be exponentially amplified.

Because the reaction vessel 150 is moved along the sliding recess 122, 132 of the two blocks 120, 130 to be repeatedly positioned on one of the two blocks 120, 130, which are controlled independently to have different temperatures, the time for conducting the entire nucleic acid amplification reaction can be reduced.

For example, in an apparatus for a nucleic acid amplification reaction using only one block, it is necessary to repeat the operations of raising and lowering the temperature of the block when the above-mentioned entire nucleic acid amplification reaction is conducted. As described above, the reaction vessel 150 moves along the sliding recess 122, 132 of the two blocks 120, 130 to be repeatedly positioned on one of the two blocks 120, 130, which are controlled independently to have different temperatures. Thus, while a specific step in the nucleic acid amplification reaction is conducted in a specific block, the temperature of the other block may be changed for the next step. Accordingly, it is possible to save the time that is consumed for repeatedly raising and lowering the temperature of the block in the apparatus that uses only single block for a nucleic acid amplification reaction.

It is possible to independently control the temperatures of the blocks 120, 130, and a temperature change of ±1° C./sec or more, ±2° C./sec or more, ±3° C./sec or more, ±3.5° C./sec or more, ±4° C./sec or more, ±4.5° C./sec or more, ±5° C./sec or more, ±6° C./sec or more, ±8° C./sec or more, or ±10° C./sec or more is enabled by a heat transfer means.

Figure 3:
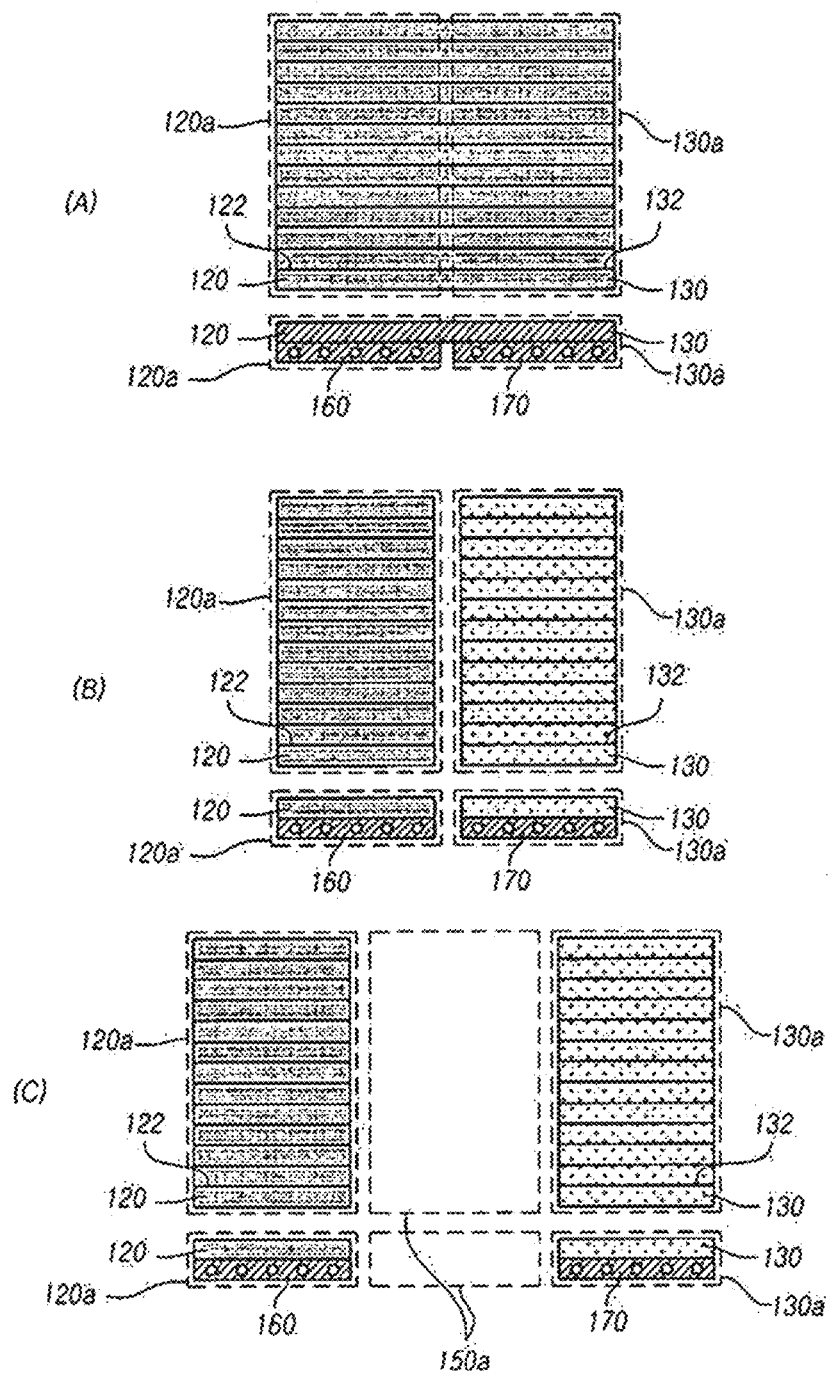
FIGS. 3A to 3C are views illustrating forms of exemplified blocks used in the present invention.

As illustrated in FIGS. 3 to 5, the reaction vessel 150 comprises two or more reaction containers, which may be: coupled to each other; separated from each other; or arranged in a row.

According to one embodiment, the reaction containers may be tubes 152 (i.e., tube form). For example, the reaction vessel 150 may comprise m×n tubes 152 (m and n are integers larger than 1). For example, the reaction vessel 150 may comprise 16, 24, 48, or 96 or more tubes 152. Meanwhile, the number of the tubes 152 of the reaction vessel 150, which are accommodated in respective sliding recesses 122 and 132 of the two blocks 120, 130 may be m or n. For example, each of the sliding recesses 122, 132 may accommodate at least 3, 5 or 6 tubes 152 of the reaction vessel. Each of the sliding recesses 122, 132 may accommodate not more than 20, 15, 10 or 8 tubes 152 of the reaction vessel.

According to one embodiment, each of the reaction containers of the reaction vessel has a flattened shape at its lower part, which is inserted into the sliding recess. Specifically, a side plane of the lower part of each of the reaction containers is tapered toward its bottom plane and the sliding recess is tapered toward its bottom plane so as to accommodate the lower part of each of the reaction containers.

According to one embodiment, the two or more reaction containers have a tube form comprising: (i) an upper part having a hollow-cylindrical shape or hollow-polygonal column shape; and (ii) a lower part configured to accommodate a reaction mixture for amplifying a nucleic acid, and fluidically connected to the upper part, the lower part having a flattened shape including front and rear planes each having a flat face, side planes narrower than the front plane, and a bottom plane, wherein the flat face of each of the front and rear planes is thermoconductively in contact with the at least two blocks.

According to one embodiment, each of the blocks 120, 130 has a top plane area and sliding recesses sufficient independently to accommodate all of the reaction containers comprised in the reaction vessel 150.

According to one embodiment, the reaction vessel 150 may be positioned on one block at the first time, and at the second time after a predetermined length of time from the first time, may be positioned on the other block. Thus, the top planes of the respective blocks 120, 130 may have the same dimension. In addition, according to one embodiment, the top plane of each of the blocks 120, 130 may have an area sufficient to accommodate all of the reaction containers of the reaction vessel 150, and each of the blocks 120, 130 may be formed with sliding recesses 122, 132 sufficient to accommodate all of the reaction containers comprised in the reaction container 150. The shapes of the blocks may vary depending on the arrangement of the sliding recesses. When the top plane of each of the blocks has a rectangular shape, the reaction vessel 150 may be efficiently moved between the blocks.

The area of the top plane of one block may vary depending on the reaction vessel 150 to be accommodated therein, and although not especially limited, may accommodate, for example, 16, 24, 48, or 96 or more reaction containers, each of which has a diameter of 5 to 10 mm, at once.

According to one embodiment, the top plane of each of the blocks 120, 130 has a rectangular or square shape. According to one embodiment, the length and breadth of the top plane of each of the blocks 120 and 130 may be 30 mm or more, 50 mm or more, or 70 mm or more, and 250 mm or less, 200 mm or less, 170 mm or less, 150 mm or less, or 100 mm or less. According to one embodiment, the at least two blocks may be the same in dimension and shape.

Although the above embodiment is described with the apparatus having two blocks, an apparatus having three, or more blocks may be also provided. For example, when three blocks are provided, the reaction vessel may be moved along the sliding recess of the three blocks, which are controlled to have different temperatures.

In the foregoing, descriptions have been made with reference to the entire configuration of an apparatus for a nucleic acid amplification, and a relative movement between the blocks and the reaction vessel. Hereinafter, a relative movement mechanism between the blocks and the reaction vessel of the apparatus for a nucleic acid amplification will be described.

FIGS. 8A to 8D are exploded perspective views illustrating an apparatus for a nucleic acid amplification according to another embodiment. FIGS. 8A to 8D illustrate detailed configurations of the blocks, the reaction vessel, and the moving module in the apparatus for a nucleic acid amplification of FIGS. 4, 5, and 7.

Referring to FIGS. 8A to 8D, an apparatus 200 for a nucleic acid amplification reaction according to another embodiment of the present invention may comprise at least two blocks 220, 230, and a moving module 240.

Each of the blocks 220, 230 has at least one sliding recess 222, 232 formed such that when a reaction vessel 250 is inserted into a sliding recess 222, 232, the reaction vessel is capable of being moved along sliding recesses between the at least two blocks.

The moving module 240 may be configured to move the at least two blocks 220, 230 and/or the reaction vessel 250 such that the reaction vessel is moved along the sliding recesses 222, 232 in relative to the at least two blocks.

The moving module 240 comprises a power transmission and driving unit 244 coupled to one of a power unit 242 providing power, the blocks 220, 230 and/or the reaction vessel 250 such that the power transmission and driving unit 244 moves one of the blocks 220, 230 and/or the reaction vessel 250 using power.

When the power transmission and driving unit 244 of the moving module 240 are coupled to the at least two blocks 220, 230 and/or the reaction vessel 250, the power transmission and driving unit 244 of the moving module 240 may be physically directly coupled to the at least two blocks 220, 230 and/or the reaction vessel 250. Alternatively, the power transmission and driving unit 244 may be physically indirectly coupled to the at least two blocks 220, 230 and/or the reaction vessel 250 through connection means (e.g., a reaction vessel holder 280).

The power unit 242 may generally be a well-known device for providing power (e.g., an electric motor, an engine, or an electromagnetic device), but is not limited to. The power transmission and driving unit 244 may be a well-known component or device that operates a target object using the power provided from the power unit 242 (e.g., various types of belts, power transmission bars, chains, screw threads or gears).

Figure 8A:
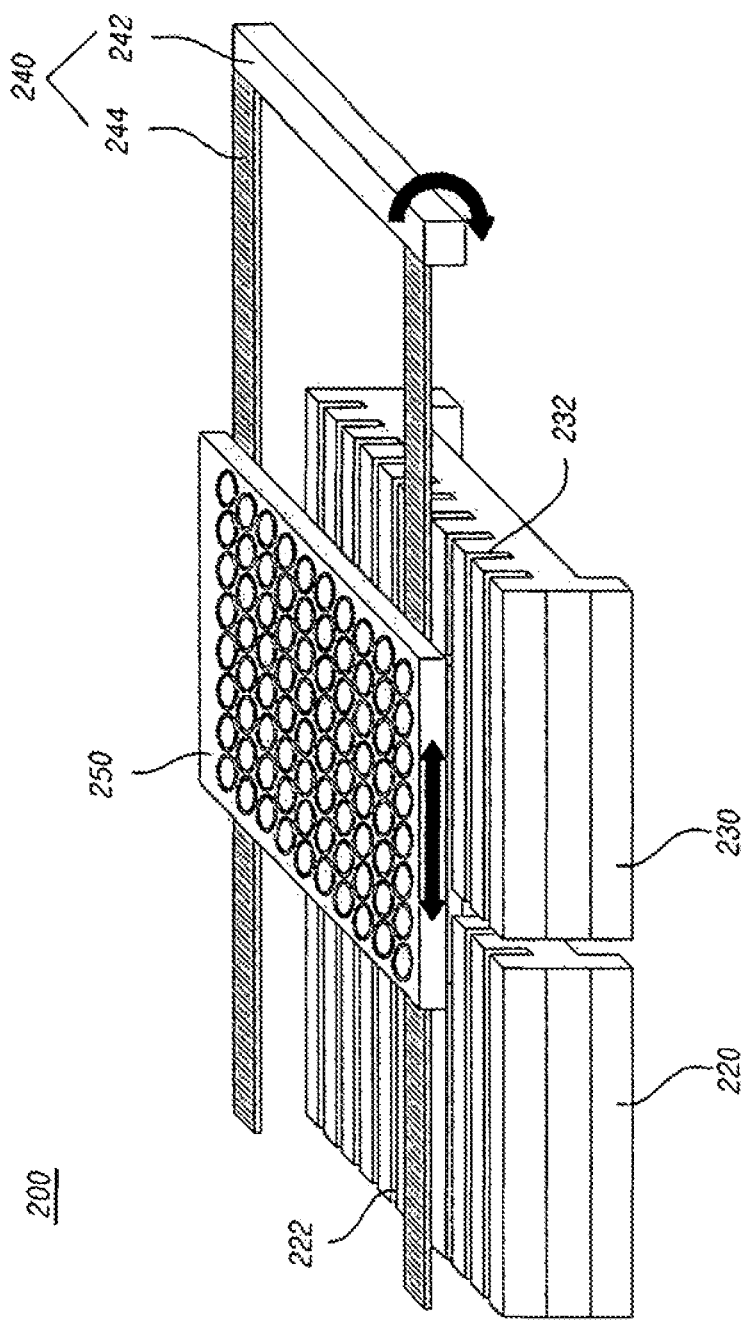
FIGS. 8A to 8D are exploded perspective views illustrating an apparatus for a nucleic acid amplification reaction according to another embodiment.

As illustrated in FIG. 8A, the power transmission and driving unit 244 may be coupled to the reaction vessel 250, and moves the reaction vessel 250 by using the power provided by the power unit 242.

Figure 8B:
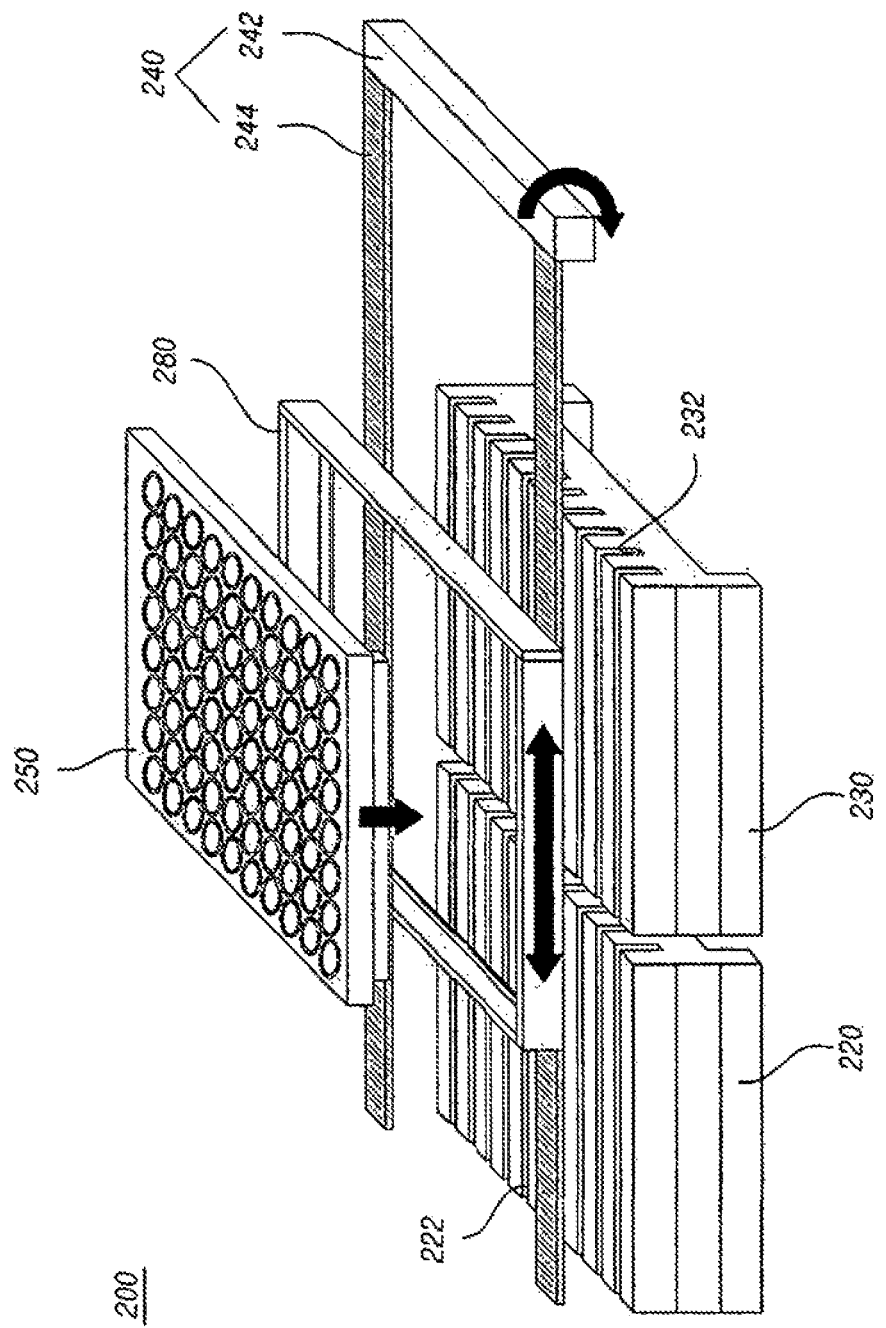

As illustrated in FIG. 8B, the apparatus 200 for a nucleic acid amplification may further comprise a reaction vessel holder 280 configured to accommodate the reaction vessel 250 wherein the apparatus 200 comprises the moving module comprising a power unit configured to provide power and a power transmission and driving unit. The power transmission and driving unit 244 may be coupled to the reaction vessel holder 280, and may move the reaction vessel holder 280 using the power provided by the power unit. When the power transmission and driving unit 244 moves the reaction vessel holder 280, the reaction vessel 250 accommodated in the reaction vessel holder 280 is also moved together with the reaction vessel holder 280.

Figure 8C:
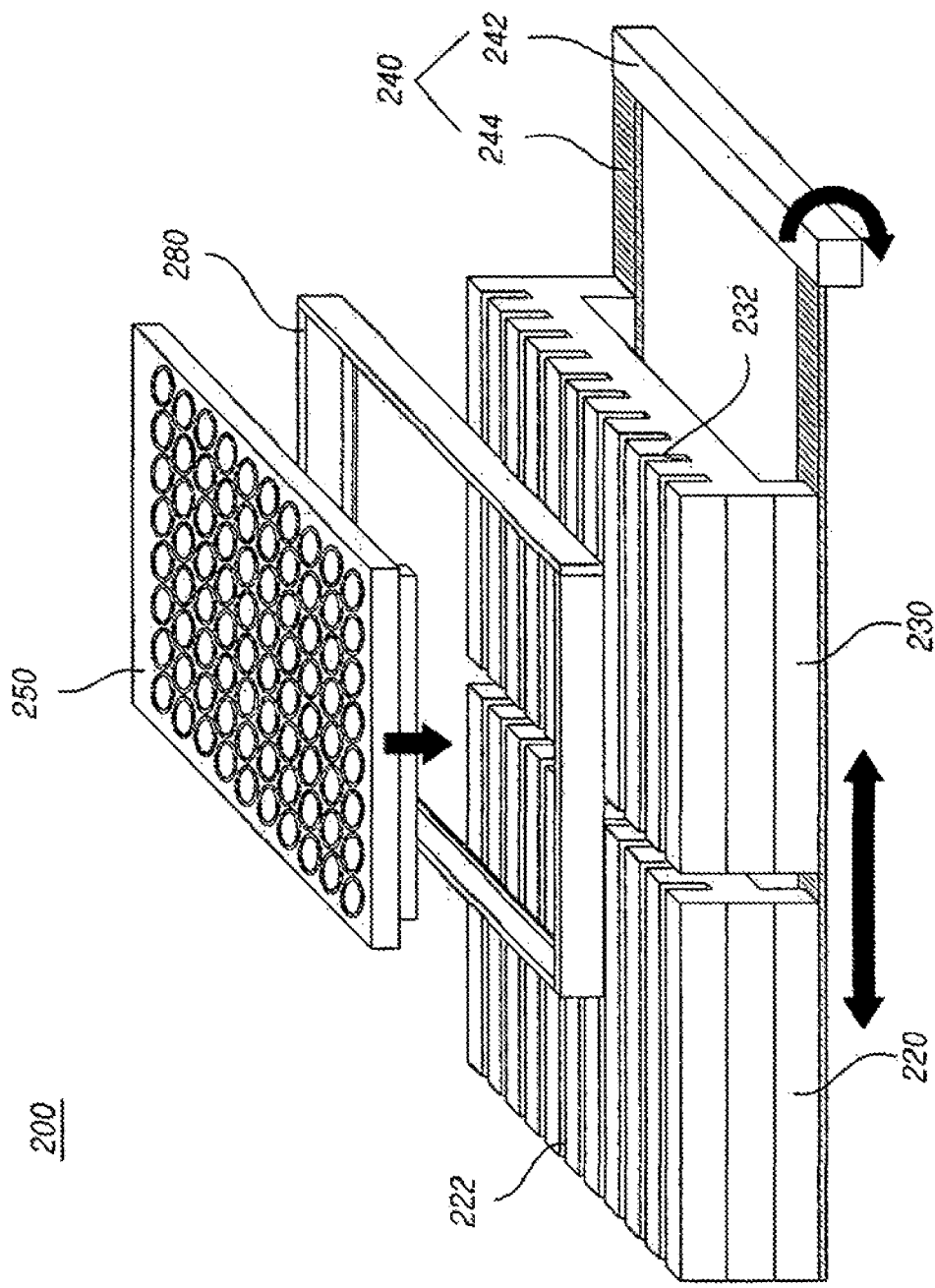
Figure 8D:
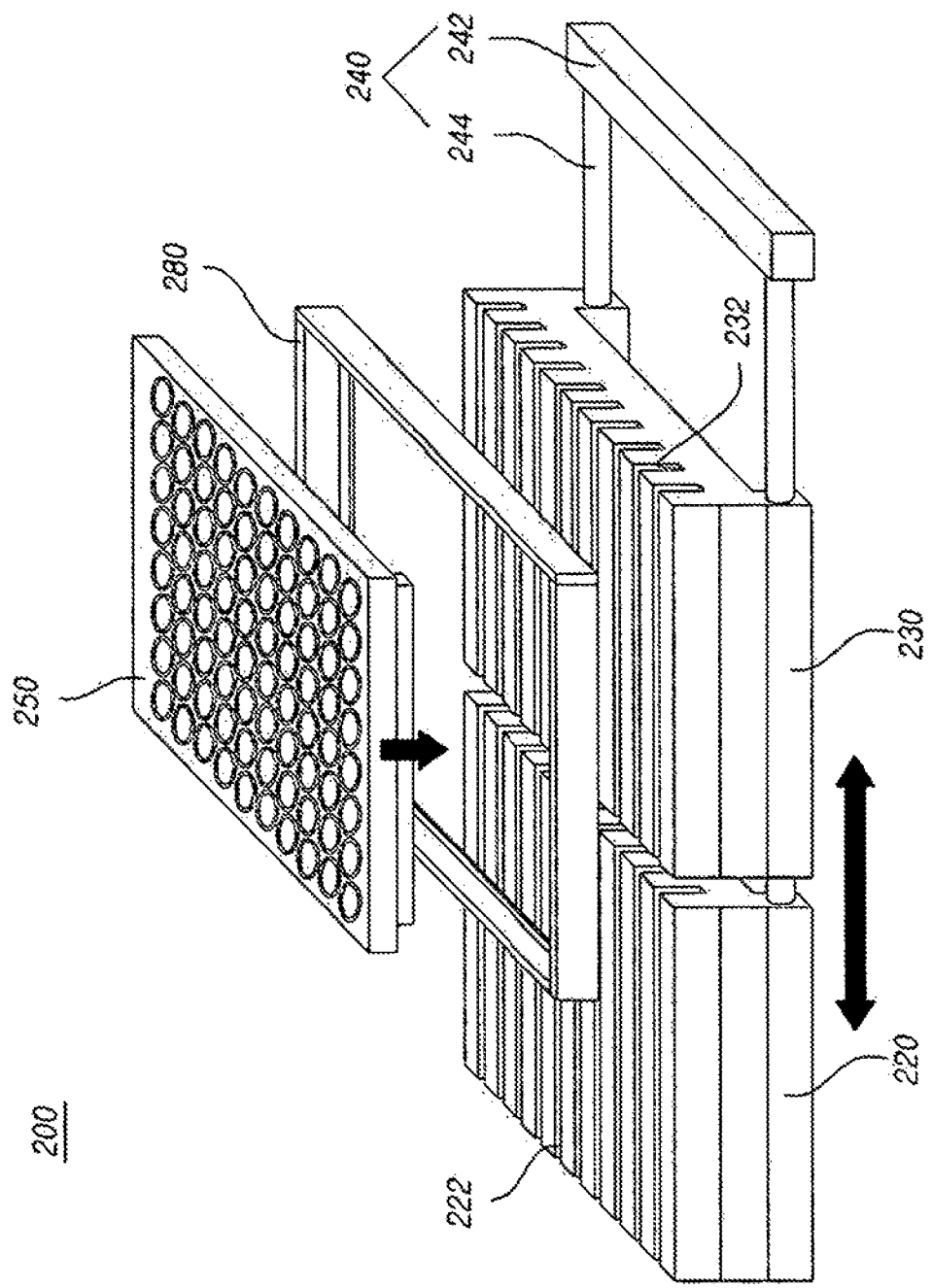

As illustrated in FIGS. 8C and 8D, the power transmission and driving unit 244 may be coupled to the blocks 220, 230 so as to move one of the blocks 220, 230.

As illustrated in FIG. 8C, the power transmission and driving unit 244 may be coupled to the lower part of two blocks 220, 230 via belts, and may move one of the blocks 220, 230 in one direction and the opposite direction using the power of the power unit 242.

As illustrated in FIG. 8D, the power transmission and driving unit 244 may be coupled to the two blocks 220, 230 via connection bars that penetrates a portion of each of the blocks 220, 230, and may move one or both of the blocks using the power provided by the power unit 242.

Although the power transmission and driving unit 244 may be coupled to the blocks 220, 230 and may move one of the blocks 220, 230 as described above with reference to FIGS. 8C and 8D, the power transmission and driving unit 244 may simultaneously move the blocks 220, 230.

According to another embodiment, two or more power units 242 may be provided. For example, separate power units 242 may be provided at the opposite sides in the moving direction, respectively.

The power transmission and driving unit 244 connected to the reaction vessel, the reaction vessel holder, or the blocks 220, 230 may be connected to, and operated by, two or more power units 242.

In addition, the blocks 220, 230 may be connected to separate connection modules, respectively, and the movements of the blocks 220, 230 may be independently controlled.

Figure 9:
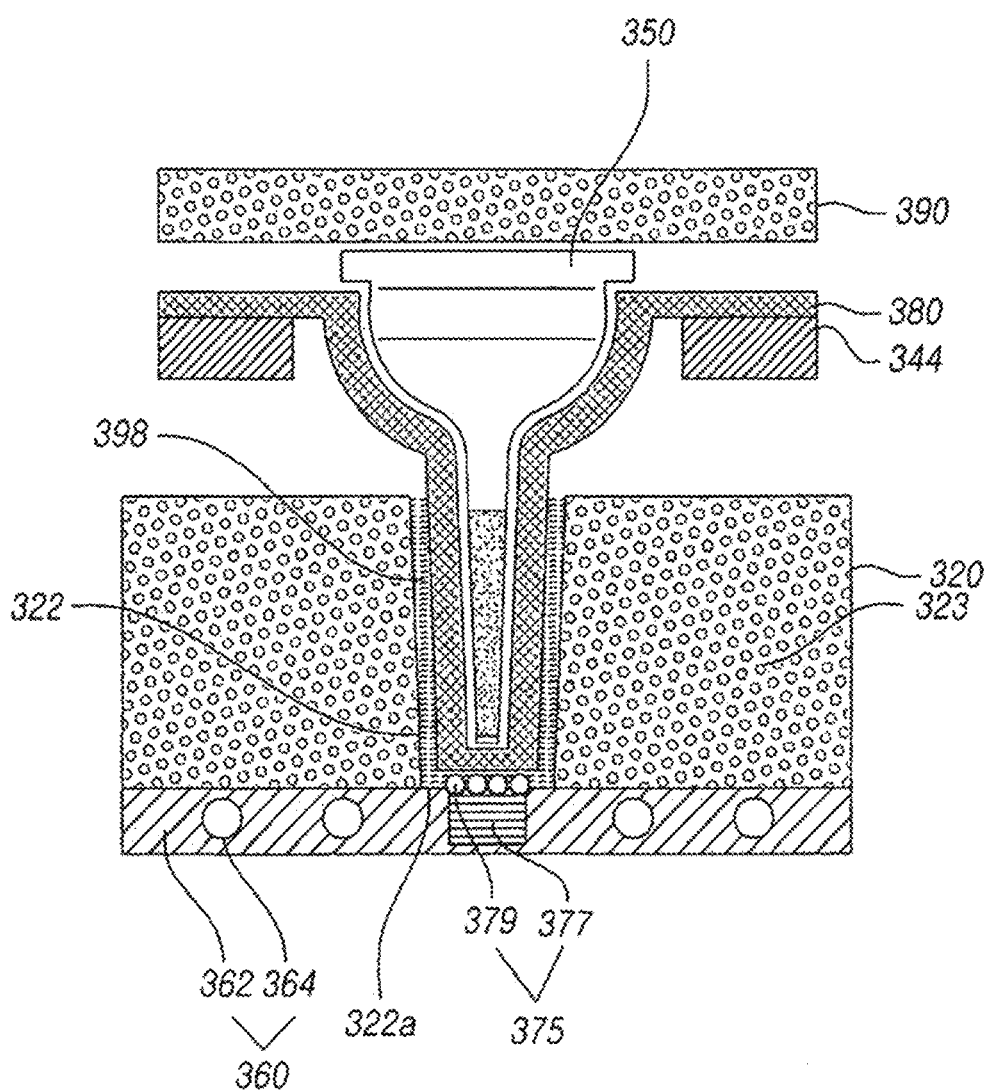
FIG. 9 is an exploded sectional view illustrating an apparatus for a nucleic acid amplification reaction according to still another embodiment.

FIG. 9 is an exploded sectional view illustrating a nucleic acid amplification apparatus according to still another embodiment.

An apparatus for a nucleic acid amplification 300 according to still another embodiment may additionally comprise a heat transfer module 360 configured to supply heat to each block 320 or to absorb heat from each block 320. The heat transfer module 360 may control the temperature of the respective blocks 320 to have different temperatures and may adjust the temperature of the respective blocks 320 to two or more different temperatures.

The heat transfer module 360 may be a device that enables both of heating and cooling. The heat transfer module 360 may separately comprise a heat supply means that supplies heat and a heat absorption means that absorbs heat.

The cooling may be conducted using the flow of a fluid or a gas.

The heat transfer module 360 may comprise the heat supply means that supplies heat with no the cooling means.

The heat transfer module 360 may be positioned below the at least two blocks 320 or positioned on or in a lateral side of the sliding recess of the least two blocks.

The sliding recess 322 may comprise a recess guide 323 positioned at the lateral side of the sliding recess 322 of the block 320. The heat transfer module 360 may be positioned at the recess guide 323 of the sliding recess 322 of the at least two blocks 320.

For example, the heat transfer module 360 may comprise a thermoelectric element 362. The thermoelectric element 362 may be, for example, a peltier element that converts electric energy into thermal energy. Upon being provided with electric energy, the thermoelectric element 362 may serve as a heating element that supplies heat or a cooling element that absorbs heat. Accordingly, depending on the heating and cooling of the thermoelectric element 362, the blocks 320, 330 may transfer heat to the reaction vessel 350, or may absorb heat from the reaction vessel 350.

The thermoelectric element 362 may be a peltier element that may conduct both of heat supply and heat absorption for the blocks 320, 330, and may be positioned below the blocks 320, 330 in the form of a plate.

The heat transfer module 360 may further comprise a cooling device (e.g., a coolant conduit 364 as illustrated in FIG. 9) or a heat absorption means in order to complement the heat absorption performance of the thermoelectric element 362.

While it has been described in the above-mentioned example that the heat transfer module 360 is positioned below the block 320, the present invention is not limited thereto. For example, the heat transfer module 360 may be positioned on or in a lateral side of the sliding recess of the blocks or on a recess guide 323 of the sliding recess 322 of the block 320. In addition, while it has been described that the heat transfer module 360 has a plate shape, the heat transfer module 360 may take various shapes such as a bar shape. For example, the heat transfer module 360 may be implemented below the block 320 by two or more bars, or may be implemented in the form of a bar in the recess guide 323 positioned at the lateral side of the sliding recess 322 of the block 320. Alternatively, the heat transfer module 360 may be implemented in such a manner that an individually controlled heat transfer element exists in at least one contact surface between each reaction container within the reaction vessel 350 and the block.

Referring to FIG. 9, the apparatus 300 for a nucleic acid amplification reaction according to still another embodiment of the present invention may further comprise a pressure control module 390 that provides pressure to the top plane of the reaction vessel 350 or reduces pressure from the top plane of reaction vessel 350. According to still another embodiment, the apparatus 300 for a nucleic acid amplification may further comprise a pressure control module (not illustrated) that provides pressure to a side plane of the reaction vessel 350 or reduces pressure from a side plane of the reaction vessel 350.

During a heat transfer reaction, the pressure control module 390 may apply pressure to the reaction vessel 350 so as to make the reaction vessel 350 and the block 320 be in close contact with each other as much as possible so as to improve the heat conductivity and to prevent the evaporation of the sample, or to prevent a cap from being opened. In addition, when moving the reaction vessel, the pressure control module 390 may reduce the pressure applied to the reaction vessel 350 so as to reduce the friction of the contact surfaces between the reaction vessel 350 and the block 320, thereby facilitating the sliding or movement.

The pressure control module 390 may comprise, for example, a cover configured to cover the top plane of the reaction vessel 350.

Meanwhile, as illustrated in FIG. 9, the reaction vessel holder 380 may have a form that encloses the whole of the upper and lower parts of the reaction vessel 350. In other words, the reaction vessel holder 380 may have the same shape as that of the reaction vessel 350 to accommodate the reaction vessel 350 therein. In such a case, the reaction vessel holder 380, which accommodates the reaction vessel 350, may be inserted in the sliding recess 322 of each block 320. In that event, the heat supplying and absorbing by the heat transfer module 360 may occur in the order of the block 320, the reaction vessel holder 380 and the reaction vessel 350. According to still another embodiment, the reaction vessel holder 380 may take a form of holding a portion (upper part or lower part) of the reaction vessel 350.

When the reaction vessel 350 or each block 320 is relatively moved, the reaction vessel holder 380 and the inner surface of the sliding recess 322 of the block 320 are in contact with each other. Accordingly, the reaction vessel holder 380 may be made of a material that is highly heat-conductive and wear-resistant, such as a metal or a metal alloy (e.g., iron, copper, aluminum, gold, silver, or an alloy thereof), but not limited to. For example, the reaction vessel holder 380 may be made of various plastics or novel materials that are imparted with a heat transfer characteristic.

According to still another embodiment, the apparatus 300 for a nucleic acid amplification may further comprise a movement assist means to reduce friction caused by movement of the reaction vessel 350 along the sliding recesses.

The movement assist means comprises a movement assist module.

For example, as illustrated in FIG. 9, a reaction vessel movement assist module 375 may comprise a bearing 379 and a shock-absorbing spring 377. The bearing 379 may partially protrude from the inner bottom plane 322a of the sliding recess 322 of each block 320, and may be partially inserted into the inner bottom plane 322a. The shock-absorbing spring 377 is in contact with the bearing 379 under the bearing 379.

The shock-absorbing spring 377 may provide an elastic force such that a portion of the bearing 379 protrudes from the inner bottom plane 322a of the sliding recess 322 as described above when the reaction vessel 350 or the reaction vessel holder 380 is not positioned on the bearing 379, or the pressure control module 390 does not press the reaction vessel 350 or the reaction vessel holder 380.

When the reaction vessel 350 is moved and a portion of the bearing 379 protrudes, the friction between the bottom plane 322a of the sliding recess 322 and the reaction vessel 350 may be reduced. Furthermore, the bearing 379 may be configured to be rotatable when the reaction vessel 350 is moved, such that the friction may be further reduced when the reaction vessel 350 is moved.

When the reaction vessel 350 or the reaction vessel holder 380 is positioned above the bearing 379 and the pressure control module 390 presses the reaction vessel 350 or the reaction vessel holder 380, the whole of the bearing 379 is inserted into the inner bottom plane 322a of the sliding recess 322, and the reaction vessel 350 or the reaction vessel holder 380 comes in contact with the inner bottom plane 322a of the sliding recess 322.

When an nucleic acid amplification reaction is performed and the bearing 379 is wholly inserted into the inner bottom plane 322a of the sliding recess 322, the contact area between the reaction vessel 350 and the inner bottom plane 322a of the sliding recess 322 may be increased, which enables a more efficient heat transfer.

FIG. 9 illustrates an example in which the power transmission and driving unit 344 is positioned above the recess guides 323 of the sliding recess 322 and is connected to the reaction vessel holder 380. The power transmission and driving unit 344 may be positioned above the recess guides 323 of two or more sliding recesses 322, and may be connected to the reaction vessel 350, the reaction vessel holder 380 or the block 320. As the number of the power transmission and driving units 344 increases, the movement of the reaction vessel 350 becomes more smooth.

According to still another embodiment, the movement assist means may be a thermal grease.

The thermal grease 398 may be applied on at least one of the reaction vessel 350, the reaction vessel holder 380, and the inner plane of the sliding recess 322 of each block 320, but not limited thereto. For example, as illustrated in FIG. 9, the thermal grease 398 may be applied on the inner plane of the sliding recess 322 of each block 320.

According to still another embodiment, the apparatus 300 for a nucleic acid amplification may further comprise a reaction vessel lifting module 395 configured to lift the reaction vessel 350 when the pressure provided to the top plane of the reaction vessel 350 is reduced.

Figure 10:
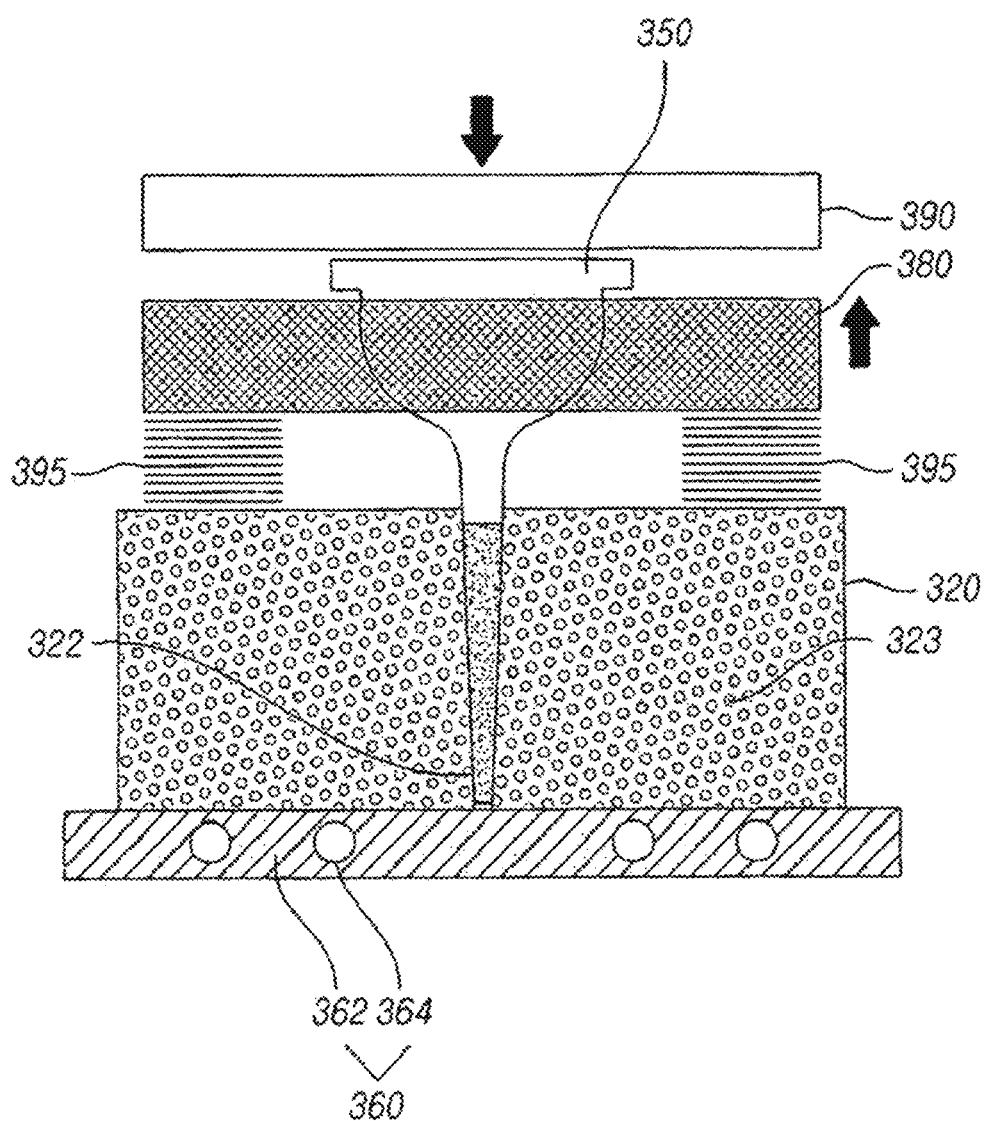
FIGS. 10 and 11 are exploded sectional views illustrating an apparatus for a nucleic acid amplification reaction according to still another embodiment.
Figure 11:
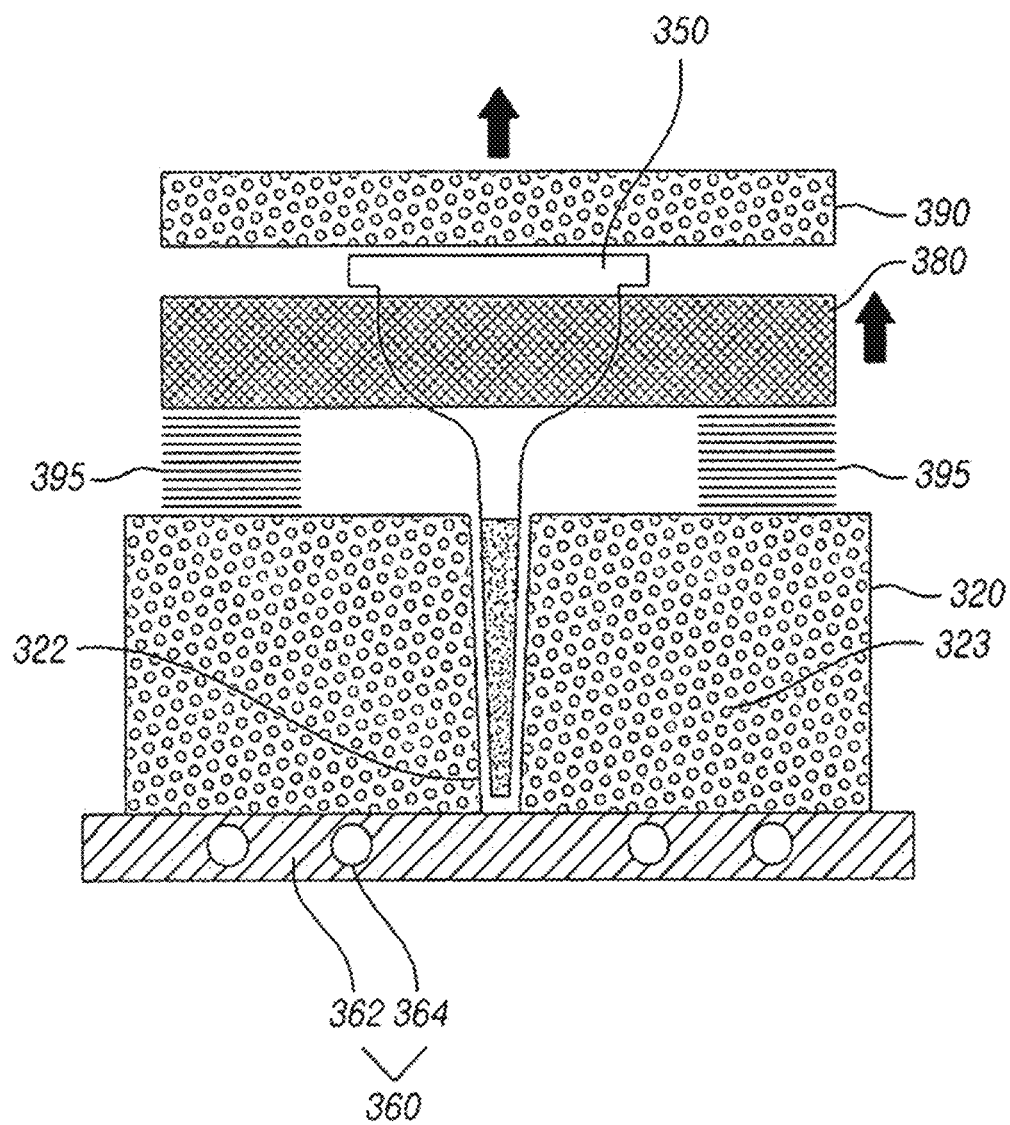

For example, the reaction vessel lifting module 395 may comprise lifting springs 395 as illustrated in FIGS. 10 and 11. The reaction vessel lifting module 395 may be interposed between the recess guide 323 of the sliding recess 322 and the bottom plane of the reaction vessel 350 or the reaction vessel holder 380.

In FIG. 10, when the pressure control module 390 presses the reaction vessel 350 or the reaction vessel holder 380, the lifting springs 395 are contracted, and the reaction vessel 350 or the reaction vessel holder 380 comes in close contact with the inner bottom plane 322a of the sliding recess 322.

In FIG. 11, when the pressure control module 390 does not press the reaction vessel 350 or the reaction vessel holder 380, the lifting springs 395 provide an elastic force such that the reaction vessel 350 or the reaction vessel holder 380 is separated from the inner bottom plane 322a of the sliding recess 322.

The reaction vessel lifting module 395 may be used as movement assist means. That is, the reaction vessel lifting module 395 may cause the reaction vessel 350 to be separated from the inner bottom plane 322a of the sliding recess 322 when the reaction vessel 350 is moved such that the reaction vessel 350 may be moved more easily. In particular, the lower part of the reaction vessel 350 is tapered toward the bottom plane, and the sliding recess 322 is tapered toward the bottom plane 322a such that the reaction vessel 350 may be moved more efficiently in a case where the block 320 configured to accommodate the lower part of the reaction vessel 350 is used. When the reaction vessel 350 with a tapered lower part is lifted by the lifting module 395 as in FIG. 11, the contact surfaces between the reaction vessel 350 and the sliding recess 322 may be reduced or eliminated, and the reaction vessel may be moved in the state where the frictional force is minimized.

The shock-absorbing spring 377 of FIG. 9 may also be an example of the lifting module.

The lifting module 395 may be positioned on the bottom plane 322a of the sliding recess 322 of the block 320 or the top plane of the block 320, but not limited thereto.

By properly designing the shape or material of the reaction vessel 350 or the reaction vessel holder 380 and the relative width of the sliding recess 322 of each block 320, it is possible to achieve the same performance without including the reaction vessel lifting module for lifting the reaction vessel 350 or the reaction vessel holder 380 when moving the reaction vessel 350 or the reaction vessel holder 380.

According to one embodiment, the apparatus further comprises a fluorescence detection device for reaction analysis comprising at least one optical module comprising: (a) a support structure; (b) an accommodation hole for a photodetector formed in one plane of the support structure, and having an optically open structure toward a location in which the reaction vessel is positioned; and (c) an optical unit comprising: (c-1) a light source for providing excitation light; and (c-2) a photodetector configured to be positioned in the accommodation hole for the photodetector such that the photodetector is arranged in an emission light path from the reaction vessel.

Alternatively, the nucleic acid amplification apparatus of the present invention may be configured to comprise a conventional detection device (or a signal detection module) as a detection device. For example, the configuration of a conventional detection device in which the detection device is not located adjacent to the heat block and the light source and photodetector are located above or below the heat block may be adopted.

Figure 12:
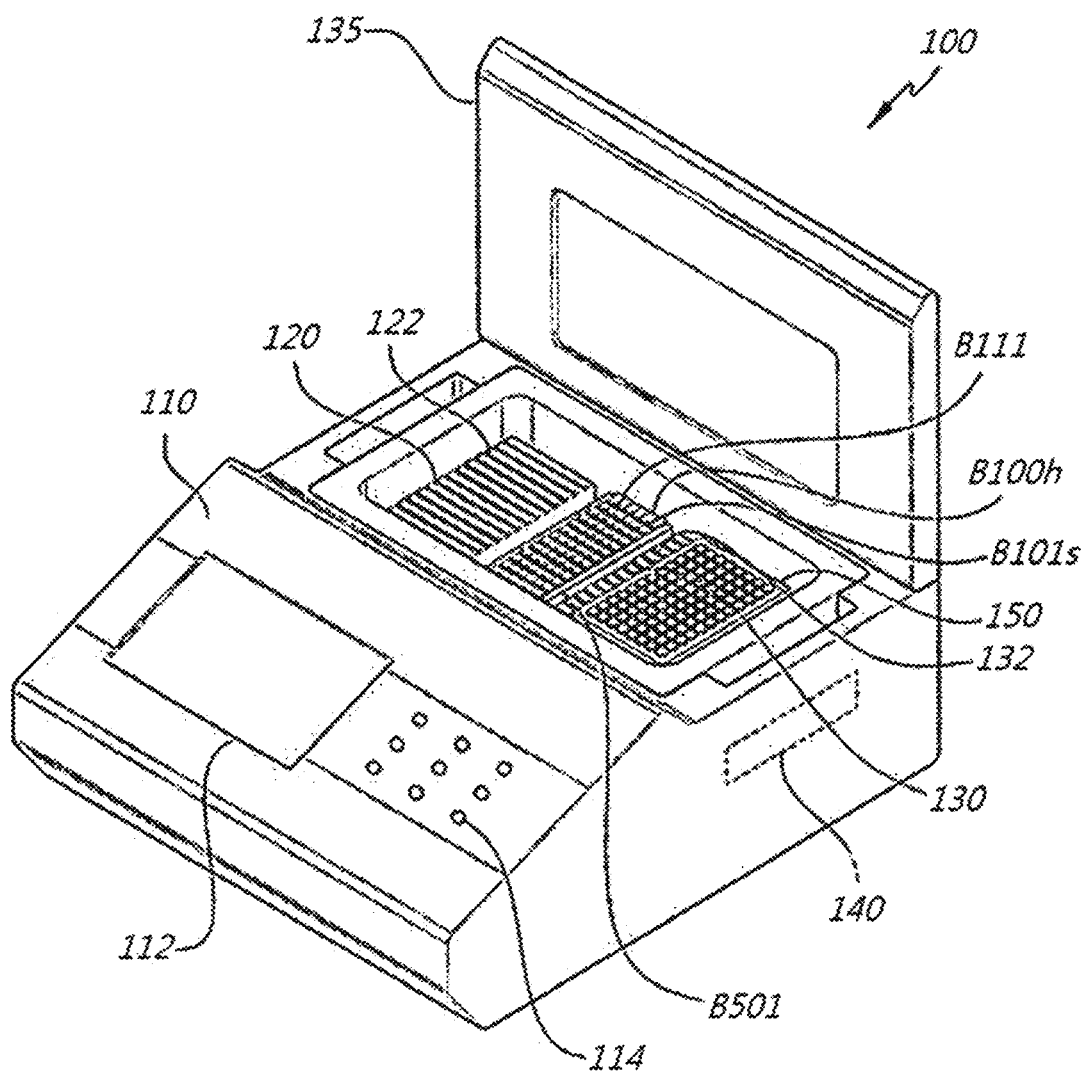
FIG. 12 shows an embodiment of a nucleic acid amplification apparatus of the present invention comprising an optical module between two heat blocks.

FIG. 12 shows an embodiment of a nucleic acid amplification apparatus of the present invention.

In FIG. 12, the nucleic acid amplification apparatus 100 comprises the main body 110, two heat blocks 120, 130, a detection device comprising an optical module B100*h* and the moving module 140. The blocks 120, 130 and the optical module B100*h* are positioned in the main body 110.

The moving module 140 may be positioned in the main body 110. The moving module 140 may be configured to move at least one of the two blocks 120, 130, the optical module B100*h* and the reaction vessel 150 such that the reaction vessel 150 is moved along the sliding recesses 122 and 132 in relative to the two blocks 120, 130 and the optical module B100*h*. The moving module 140 may be positioned on at least one of the lateral side, the front side, the rear side, the top side, and the bottom side of the blocks 120, 130, the optical module B100*h* or the reaction vessel 150.

According to one embodiment, the support structure B101, B101*s* of the fluorescence detection device B100 has at least one sliding recess B111 formed such that when the reaction vessel 150 is inserted into a sliding recess, the reaction vessel is capable of being moved along sliding recesses between the support structure and the at least two blocks 120, 130. In this arrangement, the reaction vessel may be reciprocated between the support structure and the at least two blocks.

According to one embodiment, the at least one sliding recess B111 of the support structure B101, B101*s* is connected to the at least one sliding recess 122, 132 of the at least two blocks 120, 130 with respect to the movement of the reaction vessel 150 such that when the reaction vessel 150 is inserted into a sliding recess, the reaction vessel is capable of being moved along sliding recesses between the support structure B101, B101*s* and the at least two blocks 120, 130.

The sliding recess 122, 132, B111 is not particularly limited in terms of shape, but may have a straight line or a curve line shape so as to allow the reaction vessel 150 to be moved linearly or curvedly along the sliding recess 122, 132, B111. Specifically, the sliding recess 122, 132, B111 has a straight line shape so as to allow the reaction vessel 150 to be moved linearly along the sliding recess 122, 132, B111.

Figure 30A:
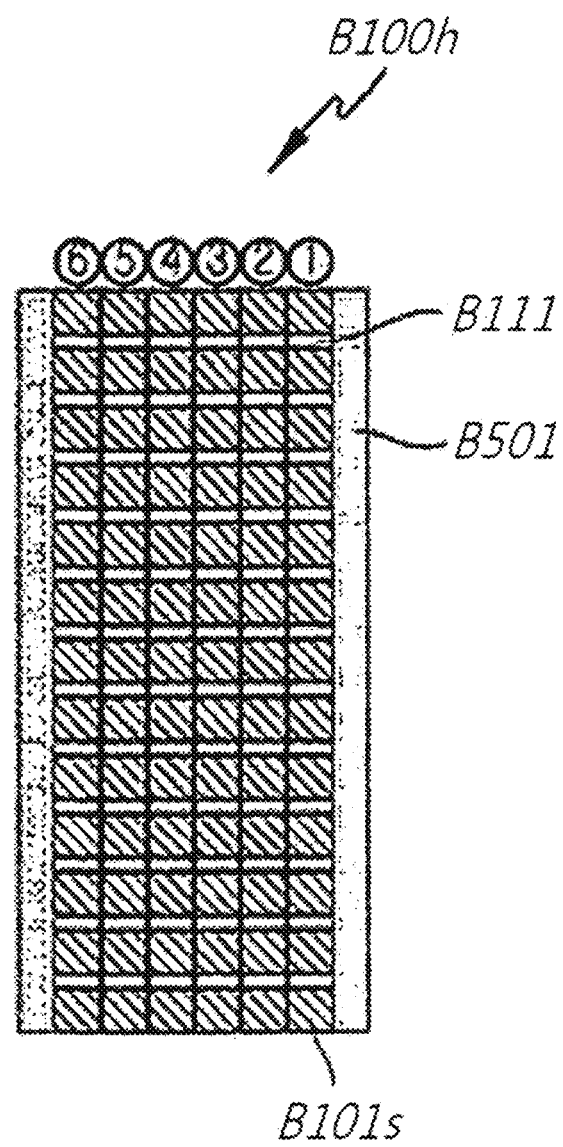
FIG. 30A is a schematic view of six optical modules including a support structure with sliding recesses. The six optical modules are mounted on an optical module base.

FIG. 30A is a schematic view of six optical modules including a support structure with sliding recesses. The six optical modules are mounted on an optical module base. The six optical modules B100*h* mounted on an optical module base B501 may be arranged in a space where the heat blocks 120, 130 in the main body 110 are positioned. A plurality of sliding recesses B111 is formed in the support structure of the six optical modules B100*h* and is connected to the plurality of sliding recesses 122, 132 of the heat blocks 120, 130.

Figure 30B:
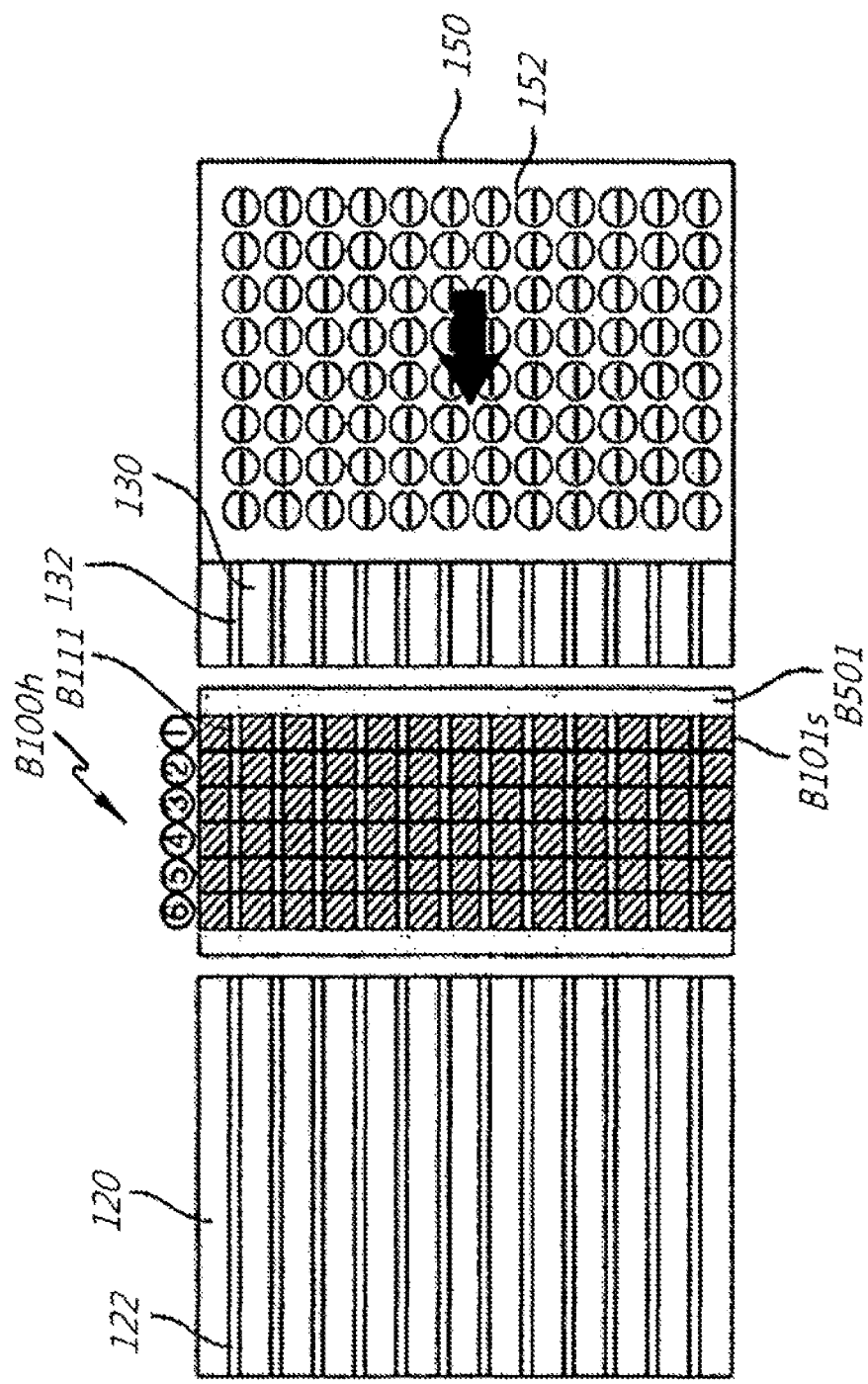
FIG. 30B shows an embodiment of the arrangement of an optical module and two heat blocks in a nucleic acid amplification apparatus of the present invention.

FIG. 30B shows one embodiment of the arrangement of an optical module of FIG. 30A and two heat blocks in a nucleic acid amplification apparatus of the present invention. A plurality of sliding recesses 122, 132 is formed in the heat blocks 120, 130 such that when the reaction tube 152 of the reaction vessel 150 is inserted into the sliding recesses 122, 132, the reaction vessel is capable of being moved along the sliding recesses 122, 132 between the heat blocks 120, 130, and corresponding sliding recesses Bill are formed in a straight line such that the reaction vessel 150 can move linearly between the heat blocks 120, 130 and the six optical modules B100*h*. The optical module B100*h* of the detection device is located between the two heat blocks 120, 130. To advance the reaction of a reaction mixture in the reaction tube 152, the reaction tube 152 of the reaction vessel 150 is inserted laterally into the sliding recesses of the right heat block. Then, the reaction vessel 150 is moved to the left side in a sliding manner such that all the reaction tubes 152 of the reaction vessel 150 are positioned in the right heat block. After the reaction is performed for a certain period of time, the reaction vessel 150 is moved to the optical module B100*h* and fluorescence emitted from the reaction vessel 150 is measured.

Fluorescence measurement may be performed in a continuous movement mode or an interrupted movement mode of the reaction vessel 150 in the optical module B100*h*. Specifically, the measurement of fluorescence may be performed during the continuous movement of the reaction vessel 150 in the optical module B100*h*. For example, when the reaction vessel tapered at its lower part described below is moved along the sliding recess, the reaction vessel may be moved with a minimized frictional force by slightly lifting the reaction vessel to separate contact surfaces between the reaction vessel and the sliding recess. Then, fluorescence may be measured while continuously moving along the sliding recess of the optical module in this manner. Alternatively, the measurement of fluorescence may be performed during an interrupted movement process including a pause step of the reaction vessel 150 for detecting fluorescence in the optical module B100*h*. For example, when the reaction vessel tapered at its lower part described below is slightly lifted to move along the sliding recess and the reaction vessel is positioned at a location where fluorescence may be measured by the optical module, the reaction vessel permits to pause and slightly press and then fluorescence is measured.

The reaction vessel 150 is further moved to the left side and located in the left heat block 120. After the reaction proceeds for a certain period of time, the reaction vessel 150 is again moved to the detection device B100 and then moved to the right heat block 130. In this manner, the reaction vessel 150 is moved and positioned in the left and right heat blocks 120, 130 and the reaction apparatus 100, and the reaction and detection are performed.

The fluorescence detection device may be arranged in various positions with respect to heat blocks. For example, the fluorescence detection device may be arranged in the right or left side of heat blocks. Alternatively, the fluorescence detection device is arranged between the heat blocks.

According to an embodiment, the fluorescence detection device is located between the at least two heat blocks. Specifically, the fluorescence detection device is located between two heat blocks.

According to an embodiment, in the arrangement of the heat blocks and the fluorescence detection device, the heat blocks and the fluorescence detection device are separated from each other in terms of thermal conduction (specifically, space) such that heat of the heat blocks is not transmitted to the fluorescence detection device. A light source and a photodetector of the fluorescence detection device are generally sensitive to heat, and their function is deteriorated when they are exposed to heat for a long time. According to one embodiment of the present invention, the fluorescence detection device, particularly the support structure or optical module base, is made of a material with low thermal conductivity.

Figure 13:
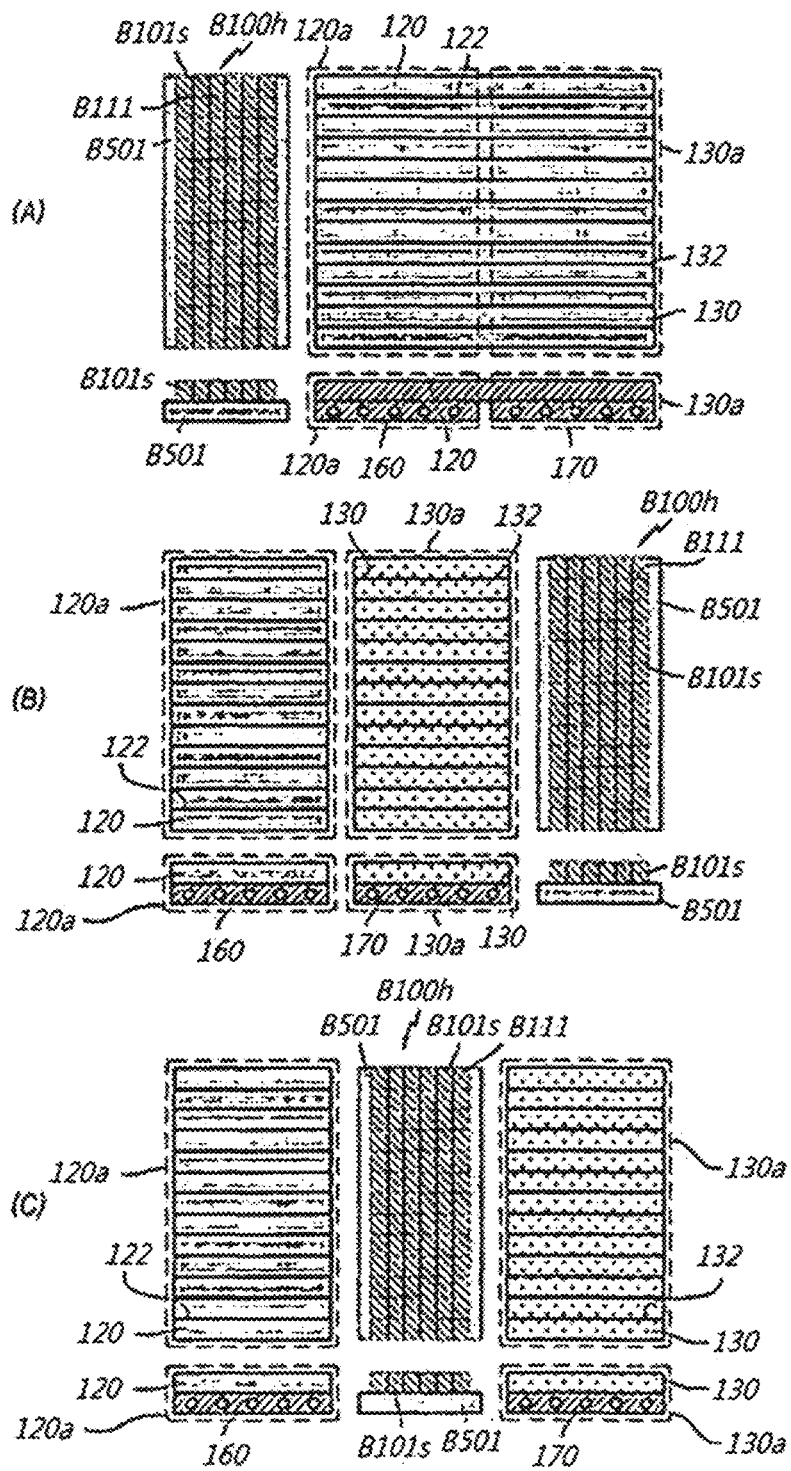
FIG. 13 is a schematic diagram showing an embodiment of arrangement of a heat block and an optical module in a nucleic acid amplification apparatus of the present invention.

FIG. 13 illustrates the arrangement of the heat block and the fluorescence detection device. In (A) and (B) of FIG. 13, the fluorescence detection device comprising the optical module B101 on the optical module base B501 is located in the left and right sides of the two heat blocks 120, 130. In (C) of FIG. 13, the fluorescence detection device comprising the optical module B101 on the optical module base B501 is located between two heat blocks 120, 130.

Figure 14:
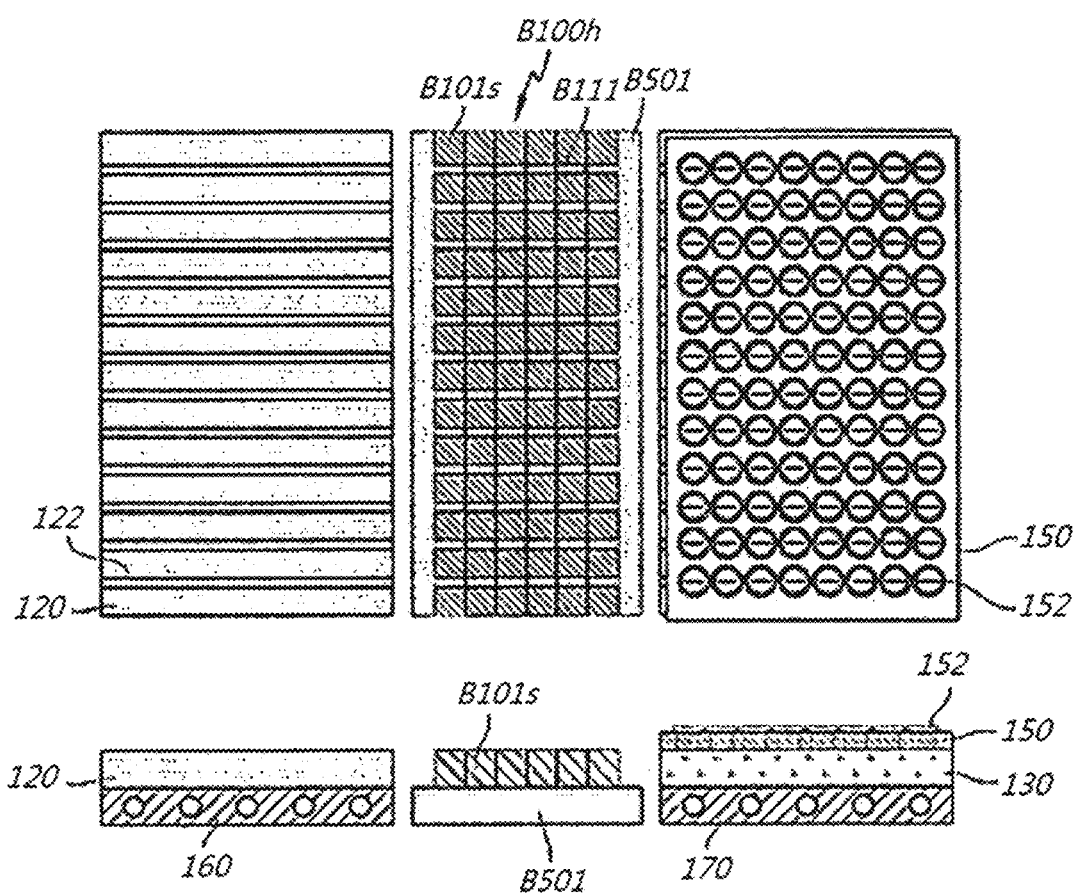
FIGS. 14-16 are views illustrating operations in which a reaction vessel is moved along sliding recesses of heat blocks and an optical module.
Figure 15:
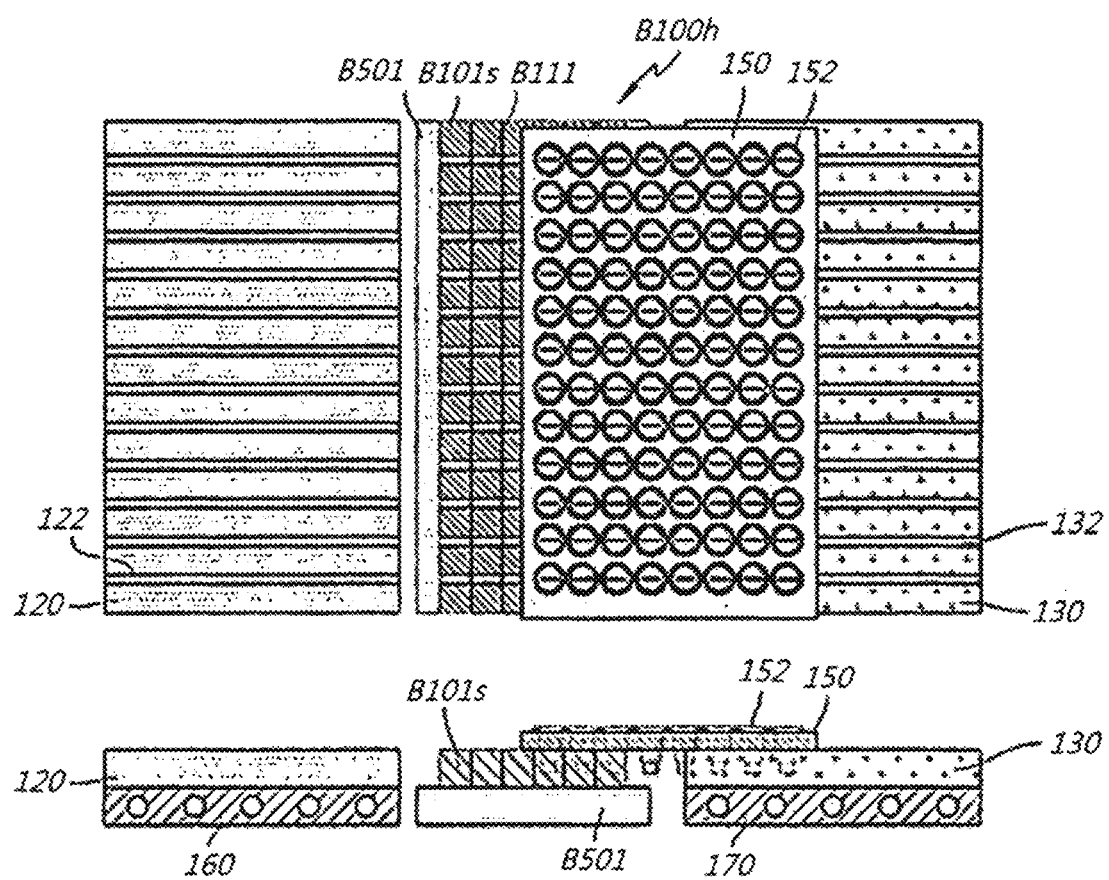
Figure 16:
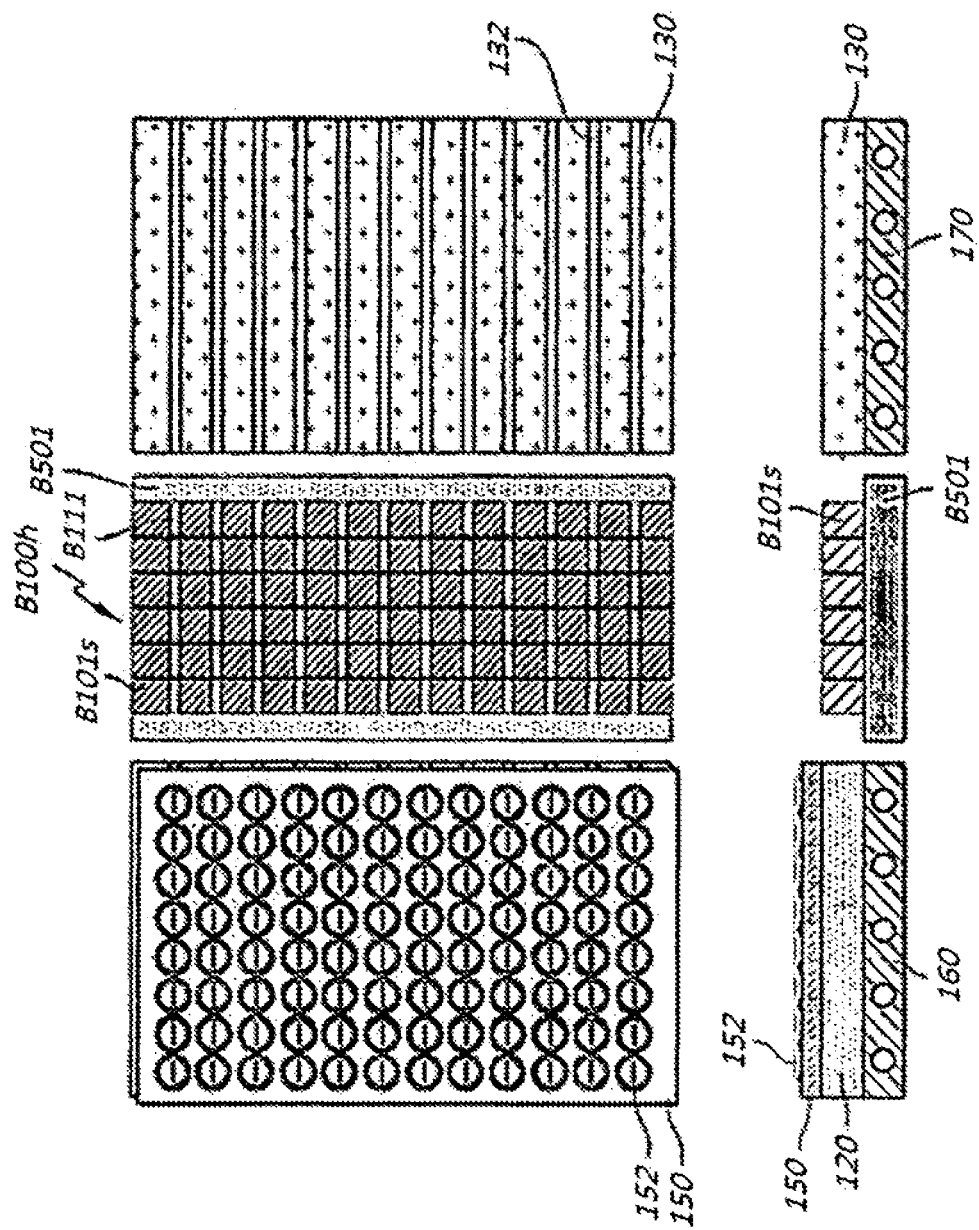

FIGS. 14-16 show operations by which the reaction vessel is moved along the sliding recesses 122, 132, B111 of the heat blocks 120, 130 and the optical module B100h. The sliding recesses 122, 132, B111 of the heat blocks 120, 130 and the optical module B100h are placed in a straight line, and the reaction vessel 150 is linearly reciprocated along the sliding recesses 122, 132, B111 forming the straight line. In the nucleic acid amplification apparatus 100, the reaction vessel 150 is positioned in one of the two heat blocks 120, 130 for reaction and then positioned in the optical module B100h for detection. Afterwards, the reaction vessel 150 is located in the other heat block 120 for reaction and then positioned in the optical module B100h for detection. Through this reciprocating linear movement, the temperature and time conditions are provided by the two heat blocks 120, 130 such that the reaction proceeds in the reaction mixture in the reaction vessel 150, and fluorescence from the reaction mixture is detected in real time in the optical module. That is, the nucleic acid amplification apparatus 100 may monitor the progress of the reaction in real time during the reaction progress. The temperatures of the two heat blocks 120, 130 are controlled by the heat transfer modules 160, 170.

When a reaction is conducted and fluorescence is detected according to technologies for real-time detection of fluorescence signals from cycles of denaturation-annealing-elongation reaction such as TaqMan method (U.S. Pat. Nos. 5,210,015 and 5,538,848), the apparatus of the present invention may be operated as follows: For convenience of description, the following description is made based on a cycling reaction of denaturing-annealing-extending reaction-detection.

The reaction vessel is placed in a first heat block set at a first temperature (denaturation temperature, for example 95° C.) for the denaturation step and then paused for a certain period of time, and then the reaction vessel is placed in a second heat block set at a second temperature (annealing temperature, for example, 65° C.) along the sliding recesses of the heat blocks and the optical module, and the annealing step is performed while pausing for a certain period of time. Afterwards, the reaction vessel is placed in the first heat block set at a third temperature (extension temperature, for example, 72° C.) along the sliding recesses of the heat blocks and the optical module, and the extension step is performed while pausing for a certain period of time, and then fluorescence is detected at a time point when the reaction vessel is located in the optical module during moving to the second heat block set to the first temperature through the optical module. By repeating this process, progress of reaction and detection of fluorescence may be performed in real time.

Unlike conventional nucleic acid amplification apparatuses, the apparatus of the present invention is operated such that the reaction proceeds by reciprocating the reaction vessel between heat blocks preset at desired temperatures and fluorescence is detected in real-time manner in this reciprocating process. Therefore, the apparatus of the present invention enables to perform a real-time nucleic acid amplification and detection very quickly without limitations of ramping time.

In the apparatus of the present invention, the moving module allows the reaction vessel to move along the sliding recess in relative to the heat block and the support structure of the detection device. More specifically, the moving module moves the reaction vessel.

FIGS. 17-20 show the relative movement of the reaction vessel by the moving module.

Each of the blocks 220, 230 and the optical module B100h has at least one sliding recess 222, 232, B111 formed such that when a part of the reaction vessel 250 is inserted into the sliding recess 222, 232, B111, the reaction vessel is capable of being moved along the sliding recess. The moving module 240 may be configured to relatively move at least one of the heat blocks 220, 230, the optical module B100h and the reaction vessel 250 along the sliding recess 222, 232, B111.

The moving module 240 comprises a power unit 242 configured to provide power and a power transmission and driving unit 244 coupled to one of the heat blocks 220, 230 and the optical module B100h, and the reaction vessel 250 and configured to move the heat blocks 220, 230, the optical module B100h or the reaction vessel 250 using the power.

The moving module 240 comprises a power transmission and driving unit 244 coupled to one of a power unit 242 providing power, the blocks 220, 230, the optical module B100h and/or the reaction vessel 250 such that the power transmission and driving unit 244 moves one of the blocks 220, 230, the optical module B100h and/or the reaction vessel 250 using power.

When the power transmission and driving unit 244 of the moving module 240 are coupled to one of the heat blocks 220, 230, the optical module B100h and the reaction vessel 250, the power transmission and driving unit 244 may be physically directly coupled to it. Alternatively, the power transmission and driving unit 244 are may be physically indirectly coupled to one of the heat blocks 220, 230, the optical module B100h and the reaction vessel 250 through connection means (e.g., a reaction vessel holder 280).

Figure 17:
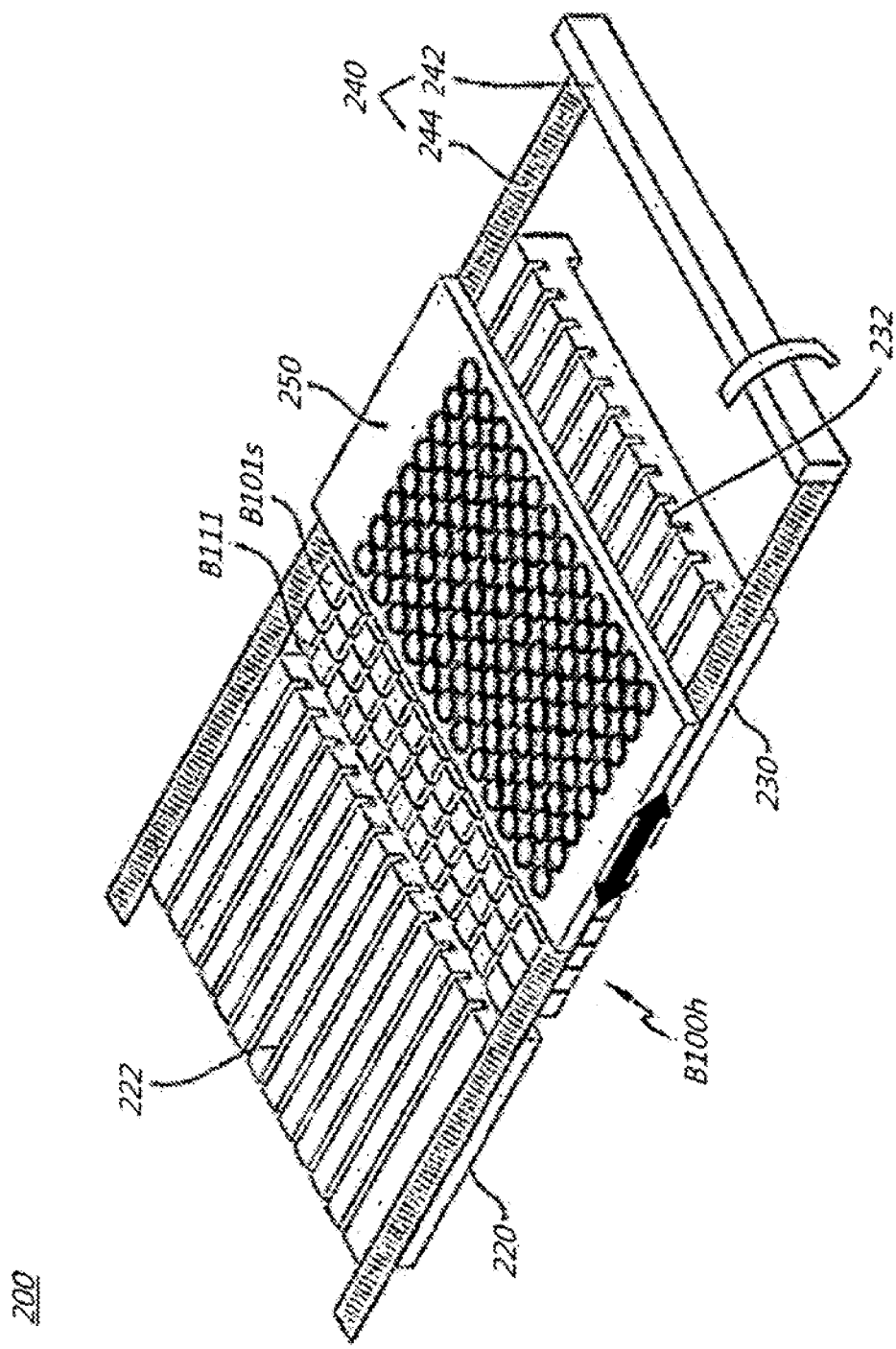
FIGS. 17-20 are views illustrating operations in which a reaction vessel is moved in relative to heat blocks and an optical module by a moving module.

As illustrated in FIG. 17, the power transmission and driving unit 244 may be coupled to the reaction vessel 250, and moves the reaction vessel 250 by using the power provided by the power unit 242.

Figure 18:
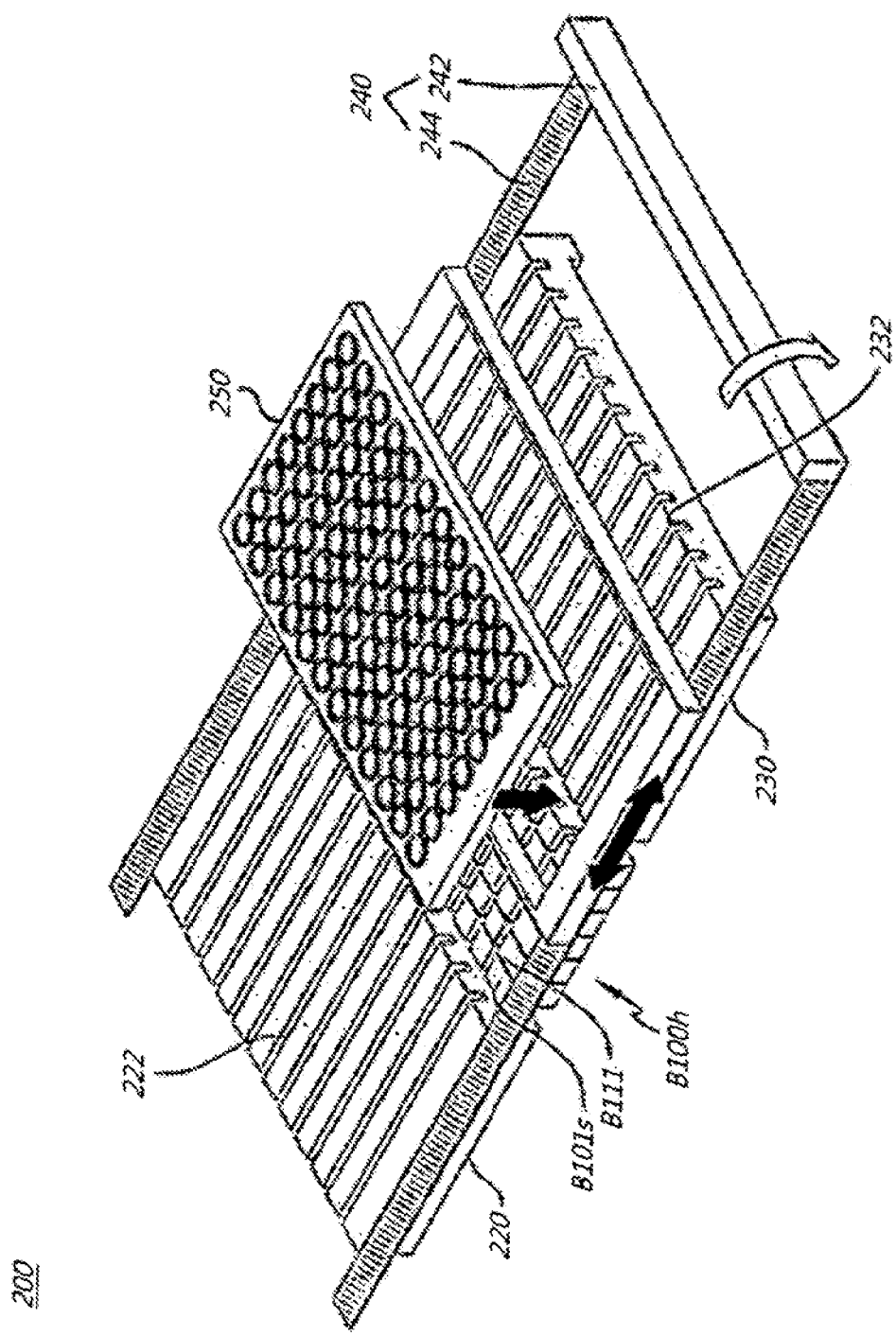

As illustrated in FIG. 18, the apparatus 200 for a nucleic acid amplification may further comprise the reaction vessel holder 280 configured to accommodate the reaction vessel 250. The power transmission and driving unit 244 may be coupled to the reaction vessel holder 280, and may move the reaction vessel holder 280. Because the power transmission and driving unit 244 moves the reaction vessel holder 280, the reaction vessel 250 accommodated in the reaction vessel holder 280 is also moved together with the reaction vessel holder 280.

Figure 19:
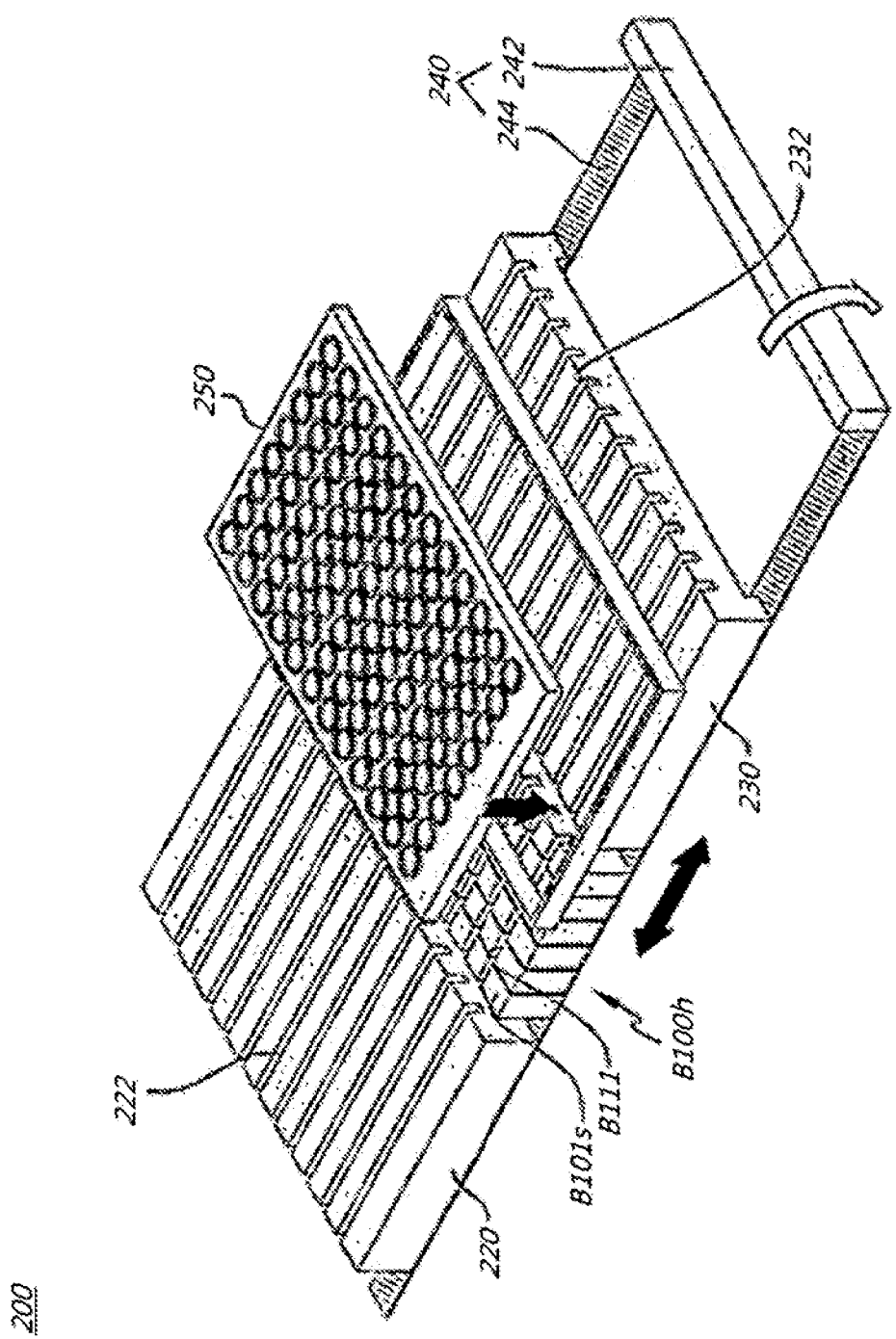
Figure 20:
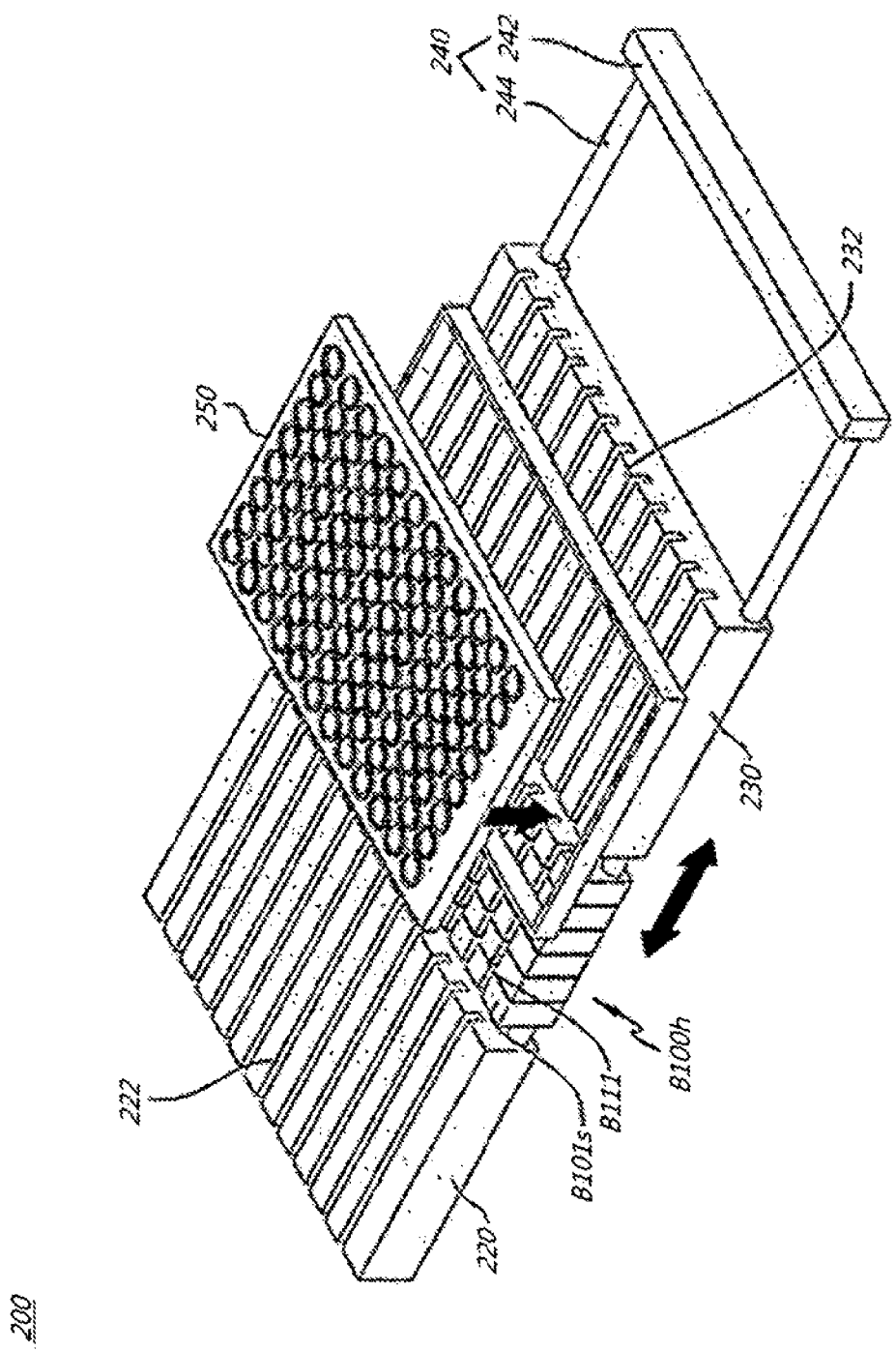

As illustrated in FIGS. 19 and 20, the power transmission and driving unit 244 may be coupled to the heat blocks 220, 230 and the optical module B100h (specifically, the support structure B101) so as to move the heat blocks 220, 230 and the optical module B100h. As illustrated in FIG. 19, the power transmission and driving unit 244 may be coupled to the lower part of the two heat blocks 220, 230 and the optical module B100h through belts, and may move the heat blocks 220, 230 and the optical module B100h using the power of the power unit 242. As illustrated in FIG. 20, the power transmission and driving unit 244 may be coupled to the two heat blocks 220, 230 and the optical module B100h through connection bars that penetrates a portion of each of the blocks 220, 230 and the optical module B100h, and may move the heat blocks 220, 230 and the optical module B100h using the power provided by the power unit 242.

The power transmission and driving unit 244 connected to the reaction vessel 250, the reaction vessel holder 280, or the blocks 220, 230 and the optical module B100h may be connected to and operated by two or more power units 242. In addition, the blocks 220, 230 and the optical module B100h each may be connected to a separate connection module and the movements of the blocks 220, 230 and the optical module B100h may be independently controlled.

According to an embodiment, the transverse end of the heat block has a trimmed edge. Placing the reaction vessel in the heat block is generally accomplished by inserting and moving the reaction vessel into the sliding recess through the transverse end of the heat block. In this case, when the edge of the transverse end is trimmed (e.g., a cut or rounded edge), the reaction vessel may be more easily inserted and moved into the sliding recess of the heat block.

Specifically, the transverse end of the heat block and the support structure of the detection device have a trimmed edge. Specifically, the transverse end of the heat block in the direction in which the reaction vessel enters has a trimmed edge.

Figure 21:
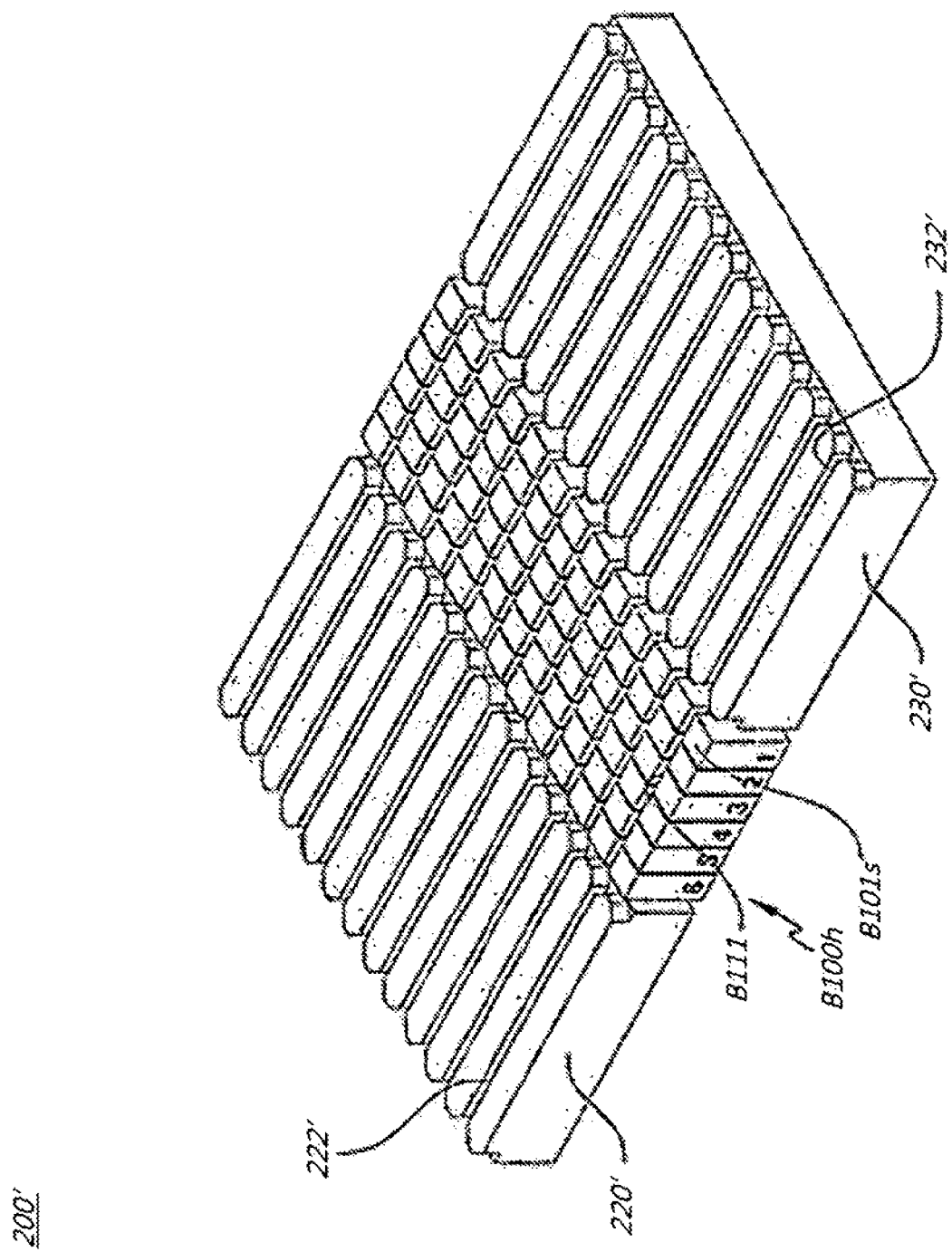
FIG. 21 shows an embodiment of the arrangement of two heat blocks and an optical module.
Figure 22:
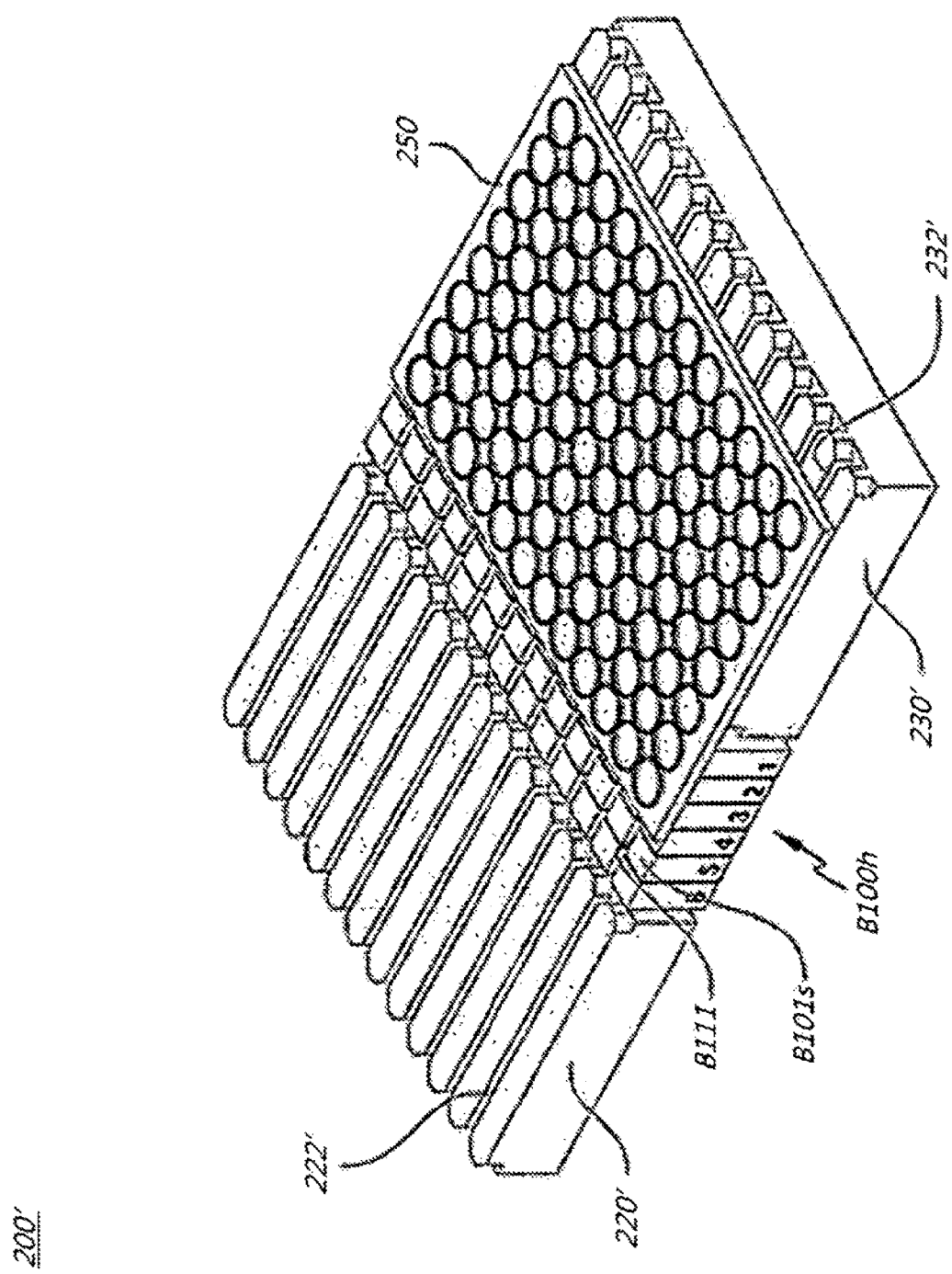
FIG. 22 shows an embodiment of the movement of a reaction vessel between two heat blocks and an optical module.

FIGS. 21-22 show one embodiment of the arrangement of the heat block and the optical module, and the movement of the reaction vessel in the apparatus of the present invention. In Figures, the transverse end of the heat blocks 220', 230' has a trimmed edge. The six optical modules B100h comprise the support structure B101 in which sliding recesses B111 are formed. The reaction vessel 250 is inserted into the sliding recesses 232' through the transverse end of the right heat block 230' and then moved.

Referring to FIGS. 13-16, the heat transfer modules 160, 170 each configured to independently supply or absorb heat may be positioned below the two heat blocks 120, 130. Two blocks 120, 130 are independently controlled to have different temperatures by the heat transfer modules 160, 170 and the temperature of each of the blocks 120, 130 may be converted to two or more different temperatures.

For a detailed description of the fluorescence detection device in the apparatus for performing a nucleic acid amplification reaction, reference is made to the description of a fluorescence detection device for reaction analysis of the invention as below.

In another aspect of the present invention, there is provided a fluorescence detection device for reaction analysis comprising at least one optical module comprising: (a) a support structure; (b) an accommodation hole for a photodetector formed in one plane of the support structure, and having an optically open structure toward a location in which a reaction vessel is positioned; and (c) an optical unit comprising: (c-1) a light source for providing excitation light; and (c-2) a photodetector configured to be positioned in the accommodation hole for the photodetector such that the photodetector is arranged in an emission light path from the reaction vessel.

The fluorescence detection device for reaction analysis is well adopted into the present amplification apparatus. Therefore, the common descriptions between them are omitted in order to avoid undue redundancy leading to the complexity of this specification.

The device of the present invention comprises a support structure. FIGS. 23A-23B and FIGS. 25-28B illustrate the support structure B101, B101s in the device of the present invention. The support structure B101, B101s may be provided with any material and any structure as long as an accommodation hole for a photodetector B201 may be formed and a photodetector B202 may be mounted therein. For example, the support structure B101, B101s may be made of metal, polymer (or plastic), or silicon. The support structure B101, B101s may be provided in various shapes and structures. For example, the support structure may have a plate shape, a recess-formed plate shape, or a shape of a hexahedron, a hexahedron having a long axis or a hexahedron having a long axis formed with a recess.

Figure 23A:
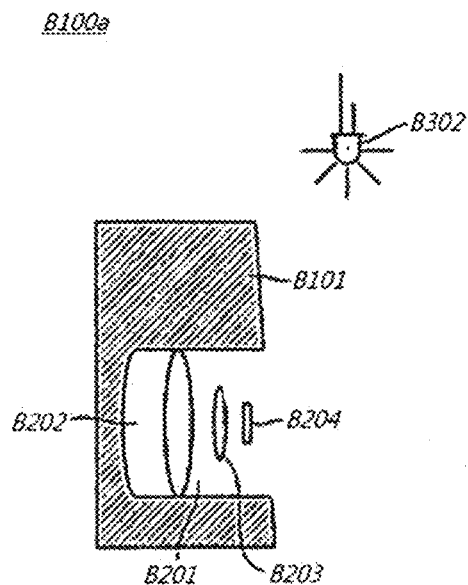
FIG. 23A shows an embodiment of an optical module of a fluorescence detection device of the present invention.
Figure 23B:
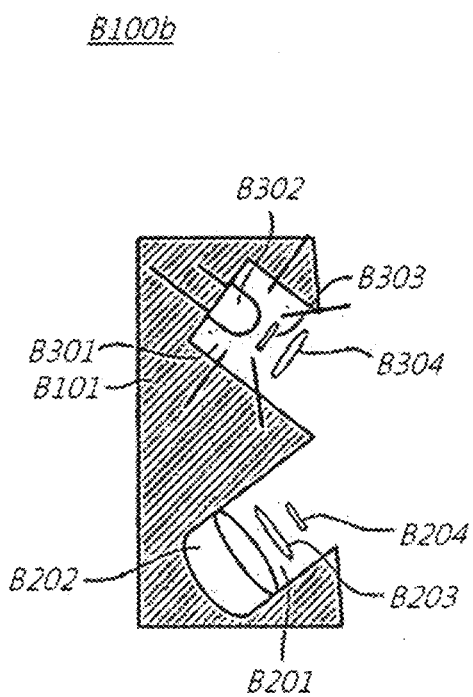
FIG. 23B shows an embodiment of an optical module of a fluorescence detection device of the present invention.
Figure 25:
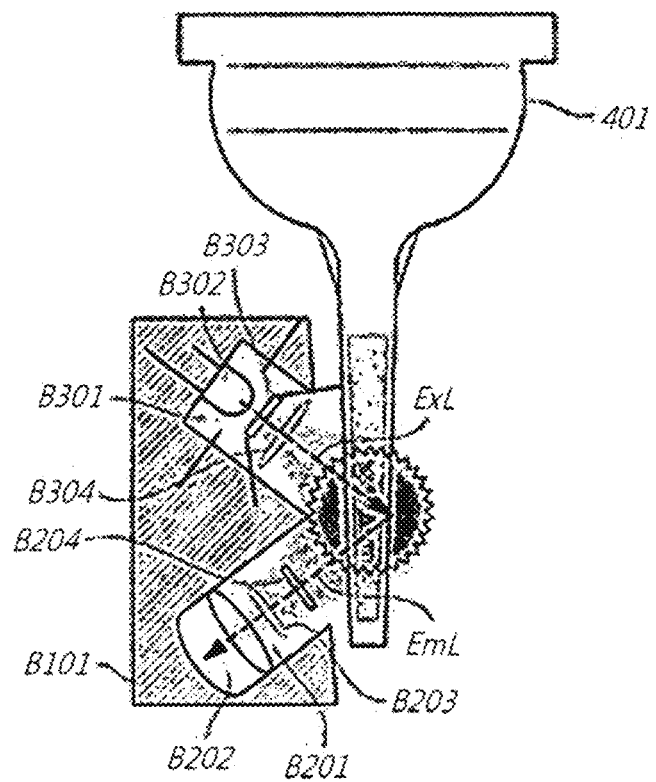
FIG. 25 shows an embodiment of an arrangement of an optical module for excitation and detection.
Figure 26:
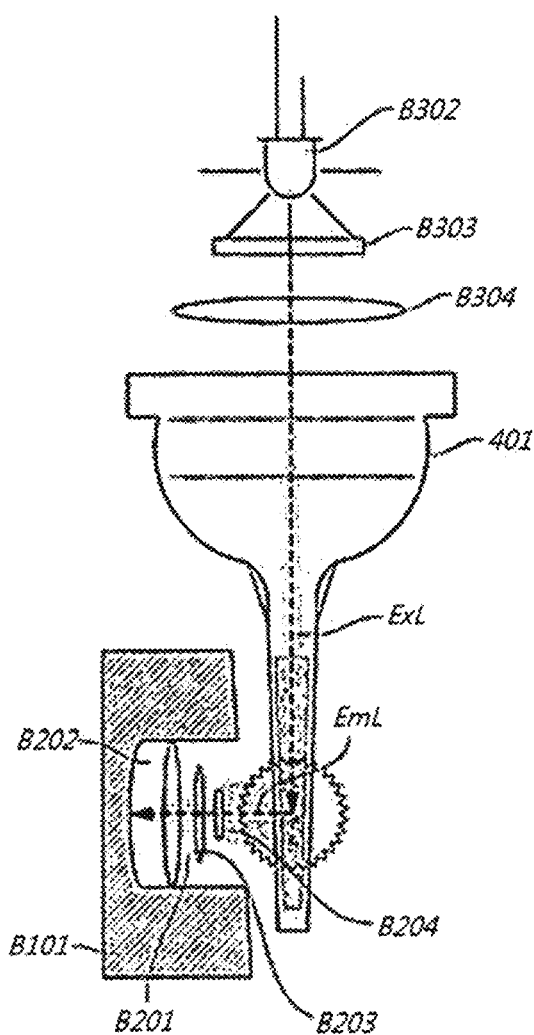
FIG. 26 represents another embodiment of an arrangement of an optical module for excitation and detection.
Figure 27A:
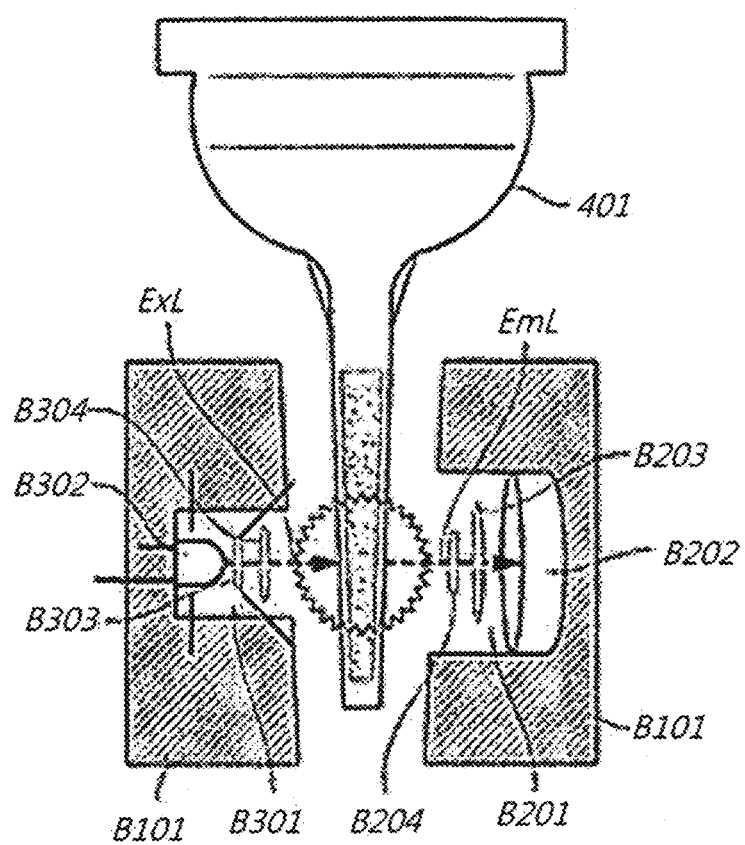
FIGS. 27A and 27B illustrate still another embodiment of an arrangement of an optical module for excitation and detection.
Figure 27B:
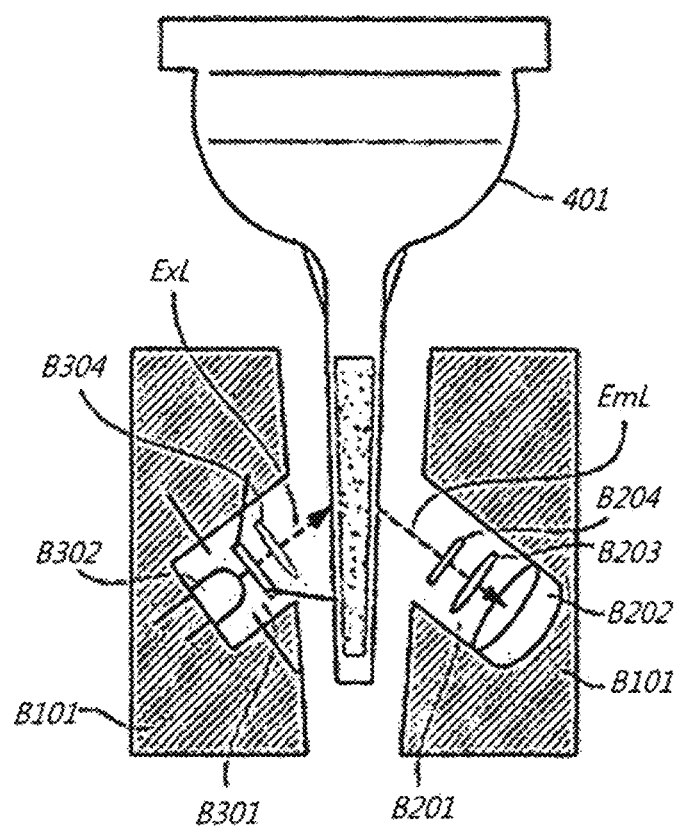

In FIGS. 23A and 26, the accommodation hole for the photodetector B201 is formed in the support structure B101. In FIGS. 23B, 25 and 28A-28B, the accommodation hole for the photodetector B201 and an accommodation hole for a light source B301 are formed in the support structure B101. Although the accommodation hole for the light source B301 is shown as being formed above the accommodation hole for the photodetector B201 in the figure, they may be arranged in the opposite and be formed side by side on both sides. Alternatively, in FIGS. 27A and 27B, the accommodation hole for the photodetector B201 is formed in the left side of the support structure B101, and the accommodation hole for the light source B301 is formed in the right side of the support structure B101. In FIGS. 27A and 27B, the accommodation hole for the photodetector B201 and the accommodation hole for the light source B301 may be arranged in the opposite. Alternatively, one of the accommodation hole for the photodetector B201 and the accommodation hole for the light source B301 may be formed in the lower surface of the support structure and the other may be formed in the side surface or vice versa (not shown). In FIGS. 23A-23B and 25-27B, the support structure B101 is schematically shown, and specifically the support structure B101 may have a closed structure such that other external lights do not interfere with emission light from a reaction vessel (see FIGS. 28A-28B).

FIGS. 23A-23B and FIGS. 25-28B illustrate the accommodation hole for the photodetector B201 formed in the support structure B101, B101s. The accommodation hole for the photodetector B201 is a structure in which the photodetector B202 is mounted and is formed in one plane of the support structure B101, B101s. Specifically, the accommodation hole for the photodetector B201 is not formed in the top plane of the support structure B101, B101s but formed in the lateral plane or the bottom plane of the support structure B101 (see FIGS. 23B and 25-28B). More specifically, the accommodation hole for the photodetector B201 is formed in the lateral plane of the support structure B101, B101s facing the location where the reaction vessel 401 including the reaction mixture to be detected is placed (see FIGS. 25-28B). More specifically, the accommodation hole for the photodetector B201 is formed in the lateral plane of the support structure B101, B101s facing the location where the reaction vessel 401 is placed, such that the photodetector B202 in the accommodation hole B201 may be positioned in an emission light path, EmL from the reaction vessel 401 (see FIGS. 25, 26, and 27A-27B). Alternatively, the accommodation hole for the photodetector B201 is formed in the bottom plane of the support structure B101, B101s such that the photodetector B202 in the accommodation hole B201 may be positioned in an emission light path, EmL from the reaction vessel 401 (not shown).

The accommodation hole for the photodetector B201 is optically open toward the direction in which the reaction vessel 401 is positioned and optically closed in the other direction. The accommodation hole for the photodetector B201 is a space that physically accommodates the photodetector B202 and is formed such that the emission light from the reaction vessel 401 detected by the photodetector B202 is not interfered (FIGS. 25-28B).

The accommodation hole for the photodetector B201 is optically open toward a position at which the reaction vessel 401 is positioned to provide a light path for the emission light from the reaction vessel 401 transmitted to the photodetector B202 (FIGS. 25-28B). The expression that one direction of the accommodation hole for the photodetector B201 is optically open means that the photodetector B202 accommodated therein has an open structure with respect to emission light so as to receive emission light from the reaction vessel 401. The expression that a direction of the accommodation hole for the photodetector B201 is optically closed means that the accommodation hole for the photodetector B201 has a closed structure such that emission light from the reaction vessel 401 transmitted to the photodetector B202 is not interfered by other external lights. For example, the accommodation hole for the photodetector B201 may have a structure in which directions other than the direction to which the reaction vessel 401 is located are physically closed. The photodetector B202 is mounted in the accommodation hole for the photodetector B201 and a signal detected by the photodetector B202 may be transmitted to a signal processor through a cable. For the communication between the photodetector B202 and the signal processor, the accommodation hole for the photodetector B201 may be physically open at a location of the photodetector B202 in the accommodation hole B201. In this case, such physical opening may be minimized such that directions other than the direction of the accommodation hole B201 to where the reaction vessel 401 is located may have an optically closed structure.

The accommodation hole for the photodetector B201 may be located in various positions of a lateral plane of the support structure B101, B101s, for example, an upper part, a lower part, or a center of a lateral plane of the support structure B101, B101s. One or more accommodation holes for the photodetector B201 may be formed.

An optical unit in the present invention comprises a light source for generating excitation light and a photodetector. FIGS. 23A-23B and 25-28B illustrate the optical unit.

The light source B302 used in the present invention may be located at various positions as long as it may excite a fluorescent material in the reaction vessel 401.

According to one embodiment of the present invention, the light source B302 is arranged above the reaction vessel 401 such that the excitation light is transmitted to the reaction vessel 401 to excite a fluorescent material in the reaction vessel 401. More specifically, the light source B302 may be located at any point on the long axis of the reaction vessel 401 above the reaction vessel 401 (see FIGS. 23A and 26). In this case, the light source B302 may be provided to be physically separated from the support structure B101. For example, the light source may be attached and located on the top of a lid or the cover (135 in FIG. 12), rather than the body in which the heat block is located.

Alternatively, the light source B302 may be arranged next to the reaction vessel 401 such that the excitation light is transmitted to the reaction vessel 401 to excite a fluorescent material in the reaction vessel 401 (FIG. 23B and FIGS. 25-28B). Specifically, the light source B302 is arranged in a plane facing the front or rear plane of the reaction vessel 401 such that the excitation light is transmitted to the reaction vessel to excite a fluorescent material in the reaction vessel (FIG. 23B and FIGS. 25-28B).

As used herein, the term "next to a reaction vessel" refers to directions relative to a reaction vessel except for the upper and lower sides of the reaction vessel, specifically represents directions relative to a reaction vessel excluding the upper and lower sides of the reaction vessel and the direction of movement of the reaction vessel. For example, in the case of using a tube of the present invention described below as the reaction vessel 401 (a reaction tube having a flattened plane at its lower part), "next to the reaction vessel of the reaction vessel 401" indicates a plane facing the front or rear plane of the reaction vessel 401.

In the present invention, the position of this light source B302 relative to the reaction vessel 401, i.e., the path of the excitation light relative to the reaction vessel 401 is a unique approach compared to conventionally known technologies (e.g., U.S. Pat. Nos. 8,137,616 and 8,236,504). According to the conventional technologies, the light source B302 is positioned above the reaction vessel 401 such that excitation light is transmitted from the upper side of the reaction vessel 401 to the lower side. Unlikely, in one embodiment of the present invention, the light source is located in a plane facing the front or rear plane of the reaction vessel 401 containing the reaction mixture, and the excitation light excites the fluorescent material contained in the reaction mixture. The prior arts require precise positioning of the light source B302 in the senses that excitation light has to pass through the upper part of the reaction vessel 401 having a relatively narrow area. Furthermore, the prior arts have difficulties in applying excitation light of the same light path length to all the reaction tubes 401. The disadvantages of these prior arts lead to a well-to-well variation. According to one embodiment of the present invention, the light source B302 is arranged in a plane facing the front or rear plane of the reaction vessel 401 containing the reaction mixture and the excitation light is transmitted to the fluorescent material of the reaction mixture such that the excitation light of the same light path length may be applied to all of the reaction tubes 401 without precise positioning of the light source B302, thereby greatly reducing the well-to-well variation.

According to an embodiment of the present invention, the light source is arranged below the reaction vessel such that the excitation light is transmitted to the reaction vessel to excite a fluorescent material in the reaction vessel (not shown).

According to an embodiment of the present invention, the light source B302 is installed in the accommodation hole for the light source B301 formed in one plane of the support structure B101, B101s, the accommodation hole for the light source B301 has optically open structure toward a direction in which the reaction vessel 401 is located and optically closed structure in the other directions (see FIGS. 23B, 25 and 27A-28B). Specifically, the accommodation hole for the light source B301 is formed in the lateral plane of the support structure B101, B101s (see FIGS. 23B, 25, 27A and 28B). Alternatively, the accommodation hole for the light source B301 is formed in the bottom plane of the support structure B101, B101s (not shown). More specifically, the accommodation hole for the light source B301 is formed in the lateral plane of the support structure B101, B101s facing the location where the reaction vessel 401 containing the reaction mixture to be detected is located (see FIGS. 25, 27A and 28B). Alternatively, the accommodation hole for the light source B301 is formed in the bottom plane of the support structure B101, B101s facing the bottom plane of the reaction vessel 401 located (not shown). More specifically, the accommodation hole for the light source B301 is formed in the lateral plane of the support structure B101, B101s facing the location where the reaction vessel 401 is located, and the light source B302 accommodated allows the excitation light to be transmitted to the reaction vessel 401.

The accommodation hole for the light source B301 has optically open structure toward a direction in which the reaction vessel 401 is located and optically closed structure in the other direction. The accommodation hole for the light source B301 is a space for physically accommodating the light source B302 and is formed such that the light source B302 can transmit the excitation light to the reaction vessel 401.

The accommodation hole for the light source B301 is optically opened toward the direction in which the reaction vessel 401 is positioned so as to provide a light path which excitation light from the light source B302 can be transmitted to the reaction vessel 401. The expression that one direction of the accommodation hole for the light source B301 is optically open means that the accommodation hole for the light source B301 has an open structure with respect to the reaction vessel 401 such that the excitation light from the light source B302 accommodated can be transmitted to the reaction vessel 401. The expression that a direction of the accommodation hole for the light source B301 is optically closed means that the accommodation hole for the light source B301 has a closed structure such that the excitation light from the light source B302 is not transmitted in any other direction than the direction toward the reaction vessel 401. For example, the accommodation hole for the light source B301 may have a structure in which any other direction than the direction toward the reaction vessel 401 is physically closed. The light source B302 is mounted in the accommodation hole for the light source B301 and may be connected through a cable to a processor which communicates a signal for activating and deactivating the light source B302. The accommodation hole for the light source B301 may has physically open structure at the position of the accommodation hole for the light source B301 in which the light source B302 is mounted for connection between the light source B302 and the processor. In this case, when such physical opening is minimized, any other direction than the direction toward the reaction vessel 401 may have an optically closed structure.

The accommodation hole for the light source B301 may be located at various positions of a lateral plane of the support structure B101, B101s, for example, an upper part, a lower part, or a center of the lateral plane of the support structure B101, B101s. One or more accommodation holes for the light source B301 may be formed.

The accommodation hole for the light source B301 may be formed in the same plane (see FIGS. 23B, 25, 28A and 28B) as or facing plane (see FIGS. 27A-27B) to the plane of the support structure B101, B101s in which the accommodation hole for the photodetector B201 is formed. Alternatively, the accommodation hole for the light source B301 may be formed in a lateral plane of the support structure B101, B101s and the accommodation hole for the photodetector B201 may be formed in a bottom plane.

When the accommodation hole for the light source B301 is formed in the same plane as the plane in which the accommodation hole for the photodetector B201 is formed, the light source B302 and/or the accommodation hole for the light source B301 may be formed such that excitation light reaches the reaction vessel at an incident angle of 10-80°, specifically 20-70°, 30-60° or 30-50° with respect to a long axis of the reaction vessel (see FIG. 25).

When the accommodation hole for the light source B301 is formed in the same plane as the plane in which the accommodation hole for the photodetector B201 is formed, the accommodation hole for the light source B301 may be located above, below, or beside the accommodation hole for the photodetector B201.

When the accommodation hole for the light source B301 is formed in a plane different from the plane in which the accommodation hole for the photodetector B201 is formed, the accommodation hole for the light source B301 may be formed in a plane facing the plane in which the accommodation hole for the photodetector B201 is formed (see FIGS. 27A and 27B). In this case, the light source B302 and the photodetector B202 are formed in locations facing each other with respect to the reaction vessel 401 (see FIGS. 27A and 27B). In this arrangement, the photodetector B202 and the light source B302 may be positioned such that excitation light path ExL from the light source B302 and emission light path EmL from the reaction vessel 401 are placed in a straight line (see FIG. 27A). For example, the light source B302 and the photodetector B202 may be installed in a direction perpendicular to the long axis of the reaction vessel 401 (see FIG. 27A). Alternatively, the photodetector B202 and the light source B302 may be arranged such that the excitation light path ExL from the light source B302 and the emission light path EmL from the reaction vessel 401 are not placed in a straight line (see FIG. 27B). For example, the light source B302 and the photodetector B202 may be installed at an acute angle to long axis of the reaction vessel 401 (see FIG. 27B).

When the accommodation hole for the light source B301 is formed in a plane different from the plane of the support structure B101 in which the accommodation hole for the photodetector B201 is formed, the accommodation hole for the light source B301 may be formed in a lateral plane of the support structure B101, B101s and the accommodation hole for the photodetector B201 may be formed in a bottom plane (not shown). In this case, the light source B302 is formed in a direction perpendicular to the photodetector B202 (not shown). In this arrangement, the photodetector B202 and the light source B302 may be positioned such that excitation light path ExL from the light source B302 and emission light path EmL from the reaction vessel 401 are placed in a perpendicular line (not shown).

As the light source B302, a light source that generates monochromatic excitation light or polychromatic excitation light may be used. For monochromatic excitation, a monochromatic light emitting diode (LED) (e.g., a 470 nm blue LED) or a monochromatic laser may be used. With regard to polychromatic excitation, white LEDs, halogen lamps, xenon lamps, tungsten-halogen lamps or quartz tungsten-halogen lamps may be used. When a light source 302 generating polychromatic excitation light is used, a suitable filter 303 may be used to provide light with a desired excitation wavelength (see FIGS. 23B and 25-28A).

In addition, the light source B302 may be used in "a light source-optical fiber" manner. In this case, the optical fiber may be installed in the accommodation hole for the light source B301 and the light source B302 may be installed in another part of the support structure such that the light source B302 and the optical fiber are optically connected to each other. In connection with installation in the accommodation hole for the light source, the light source is understood herein to encompass the light source-optical fiber. Therefore, the description that the light source is installed in the accommodation hole for the light source encompasses that the optical fiber connected to the light source is installed in the accommodation hole for the light source.

The excitation wavelength provided by the light source B302 may be, for example, 450-490 nm (for FAM or SYBR Green I), 515-535 nm (for Hex, Vic, Tet or Cal Gold 540), 560-590 nm (for Rox, Texas Red or Cal Red 610), 620-650 nm (for Cy5 or Quasar 670) and 672-684 nm (for Quasar 705).

A lens B304 may additionally be installed between the light source B302 and the reaction vessel 401 such that excitation light from the light source B302 is focused on the reaction mixture in the reaction vessel 401 (see FIGS. 23B and 25-28A). Alternatively, the lens B304 may be installed in the light source-filter-lens-reaction vessel order (see FIGS. 23B and 25-28A).

The optical unit used in the present invention comprises a photodetector. FIGS. 23A-23B and FIGS. 25-28B illustrate the photodetector B202.

Figure 24:
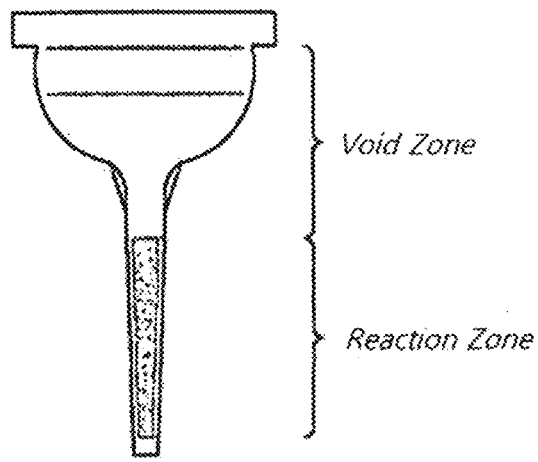
FIG. 24 is a schematic diagram of a reaction tube 401 of a reaction vessel useful in the present invention.

In FIG. 24, the reaction vessel 401 may be divided into a reaction zone where a reaction mixture (containing a fluorescent material) is occupied and a reaction (for example, a nucleic acid amplification reaction) proceeds and a void zone that is not occupied by the reaction mixture. By excitation light of the light source B302, emission light is generated from the fluorescent material in the reaction vessel 401, and the emission light is emitted in various directions. In one embodiment of the present invention, the photodetector B202 is arranged in the emission light path of the emission light which passes through a reaction zone occupied by a reaction mixture in the reaction vessel 401 and does not pass through a void zone not occupied by the reaction mixture (see FIGS. 24-27B). This localization of the photodetector is one of the features of the present invention.

According to the present invention, the photodetector B202 is typically localized such that the photodetector B202 detects a sideward directional emission of an emission light EmL with respect to the excitation light path ExL of the light source B302. According to one embodiment of the present invention, the photodetector B202 is arranged to detect a sideward directional emission of an emission light EmL with respect to the excitation light path ExL of the light source B302. The sideward emission light with respect to the excitation light path ExL may be an emission light emitted laterally from the reaction zone 401. According to one embodiment of the present invention, the photodetector B202 is arranged to detect the emission light emitted laterally from the reaction zone 401. According to another embodiment, the photodetector B202 is arranged below the reaction vessel 401 or in a plane facing the front or rear plane of the reaction vessel 401.

According to an embodiment, the photodetector B202 may be formed in the same plane as the plane of the support structure B101, B101s in which the light source B302 is installed.

When the accommodation hole for the light source B301 and the accommodation hole for the photodetector B201 are formed in the same plane of the support structure B101, B101s (see FIGS. 23B, 25 and 28A and 28B), the photodetector B202 and/or the accommodation hole for the photodetector B201 may be formed such that the emission light from the reaction vessel 401 reaches the photodetector B202 at an angle of 10-80°, specifically 20-70°, 30-60° or 30-50° with respect to a long axis of the reaction vessel 401. When the accommodation hole for the light source B301 and the accommodation hole for the photodetector B201 are formed in the same plane of the support structure B101, B101s (see FIGS. 23B, 25, 28A and 28B), the direction of the excitation light directed from the light source B302 to the reaction vessel 401 and the direction of the emission light directed from the reaction vessel 401 to the photodetector B202 may form an angle of 30-160°, specifically 40-130°, 40-110°, 50-100°, 60-90° or, 70-90° (e.g., 90°).

When accommodation hole for the photodetector B201 is formed in a plane different from the plane of the support structure B101 in which the accommodation hole for the light source B301 is formed, the accommodation hole for the photodetector B201 may be formed in a plane facing the plane of the support structure B101 in which the accommodation hole for the light source B301 is formed (see FIGS. 27A and 27B). In this case, the light source B302 and the photodetector B202 are formed in locations facing each other with respect to the reaction vessel 401 (see FIGS. 27A and 27B). In this arrangement, the photodetector B202 may be located on the opposite side of the light source B302 with respect to the reaction vessel 401 (see FIGS. 27A-27B). According to one embodiment, the photodetector is arranged in a plane facing the front or rear plane of the reaction vessel.

When the accommodation hole for the photodetector B201 is formed in a plane different from the plane of the support structure B101 in which the accommodation hole for the light source B301 is formed, the accommodation hole for the photodetector B201 may be formed in a lateral plane of the support structure B101, B101s and the accommodation hole for the light source B301 is formed in a bottom plane (not shown). According to one embodiment, the photodetector is arranged below the reaction vessel or in a plane facing the front or rear plane of the reaction vessel. According to the conventional known technique (e.g., U.S. Pat. No. 8,236,504), the photodetector is located above the reaction vessel and the photodetector therefore detects the emission light passing through the void zone of the reaction vessel. Most of conventional techniques use a beam splitter to refract emission light to allow the emission light to reach the photodetector. Unlikely, in one embodiment of the present invention, the photodetector B202 is arranged in the emission light path of the emission light which passes through the reaction zone occupied by the reaction mixture in the reaction vessel 401 and does not pass through the void zone not occupied by the reaction mixture, or to detect the emission light emitted in the sideward or downward from the reaction zone (see FIGS. 25 and 27A-27B). Therefore, in one embodiment of the present invention, the photodetector B202 may be arranged below the reaction vessel 401 or in a plane facing the front or rear plane of the reaction vessel 401 to detect the emission light.

In the prior arts, a precise positioning of the photodetector is required because it detects the emission light passing through the upper part of the reaction vessel having a relatively narrow area. In addition, the prior arts have difficulties in detecting emission light with the same light path length from all reaction tubes. The disadvantages of these prior arts lead to a well-to-well variation. According to an embodiment of the present invention, the detection of the emission light using a photodetector arranged in a plane facing the front or rear plane of the reaction vessel (i.e., next to the reaction vessel) permits to detect emission lights with the same light path length for all reaction tubes without precise positioning of the photodetector, thereby reducing the well-to-well variation. Furthermore, the photodetector B202 used in the present invention may not require the conventional beam splitter.

The photodetector B202 used in the present invention comprises various photodetectors known in the art. For example, the photodetector B202 may be fabricated to comprise a plurality of photodiodes, and each of the plurality of photodiodes detects fluorescence of specific wavelength. The photodetector B202 may be configured to have 1-6 channels. The channels may have a maximum detection wavelength of 500-800 nm (specifically, 520-730 nm). For example, the channels may have the maximum detection wavelength of 530 nm, 560 nm, 580 nm, 610 nm, 640 nm, 670 nm or 710 nm.

According to one embodiment, a detection channel may be defined by using a filter B204 to allow emission light of specific wavelength to reach the photodetector B202, before emission light reaches the photodetector B202 (see FIGS. 23A-23B and FIGS. 25-28A). The maximum detection wavelength of the detection channel may be determined according to the maximum emission wavelength of a fluorescent dye, which may be in the range of ±10 nm when these two wavelengths are different.

According to an embodiment, a crosstalk of a fluorophore detected in neighboring channel is 50% or less, more specifically 30% or less. According to an embodiment of the present invention, in order to minimize the crosstalk, the channel of the photodetector B202 exhibits a maximum detection wavelength difference of 25 nm or more.

As the photodetector B202, a photodiode, a photomultiplier, a charge-coupled device (CCD), an avalanche photodiode, a photoresistor, a bolometer or a CMOS image sensor may be used.

In addition, the photodetector B202 may be used in "an optical fiber-photodetector" manner. In this case, the optical fiber is installed in the accommodation hole for the photodetector B201 and the photodetector B202 is installed in another part of the support structure such that the photodetector B202 and the optical fiber are optically connected to each other. In connection with installation in the accommodation hole for the photodetector, the photodetector is understood herein to encompass the optical fiber-photodetector. Therefore, the description that the photodetector is installed in the accommodation hole for the photodetector encompasses that the optical fiber connected to the photodetector is installed in the accommodation hole for the photodetector.

A lens B203 may additionally be installed between the reaction vessel 401 and the photodetector B202 such that the emission light from fluorescent material of reaction mixture is focused on the photodetector B202 (see FIGS. 23A-23B and FIGS. 25-28A).

According to an embodiment, the light source B302, the accommodation hole for the light source B301, the photodetector B202, and/or the accommodation hole for the photodetector B201 are installed such that the excitation light from the light source B302 does not enter the photodetector B202. Both the accommodation hole for the light source B301 and the accommodation hole for the photodetector B201 have a hole structure, which prevents the excitation light from the light source B302 from entering the photodetector B202. Alternatively, by conferring a defined light path, the excitation light from the light source B302 is restrictively transmitted to the reaction vessel 401 along this light path without entering the photodetector B202. The lens 304 which may be additionally installed before the light source B302 may also serve to prevent the excitation light from entering the photodetector B202.

According to an embodiment of the present invention, the optical module comprises a plurality of optical units, and the plurality of optical units provides excitation lights of different wavelengths to the reaction vessel and detects emission lights of different wavelengths from the reaction vessel. For example, the device of the present invention may be manufactured as an optical module having a plurality of optical units comprising a plurality of light sources and a plurality of photodetectors. Each of the plurality of light sources providing excitation lights of different wavelengths to the reaction vessel is used in a pair with each corresponding photodetector of the plurality of photodetectors.

Figure 28A:
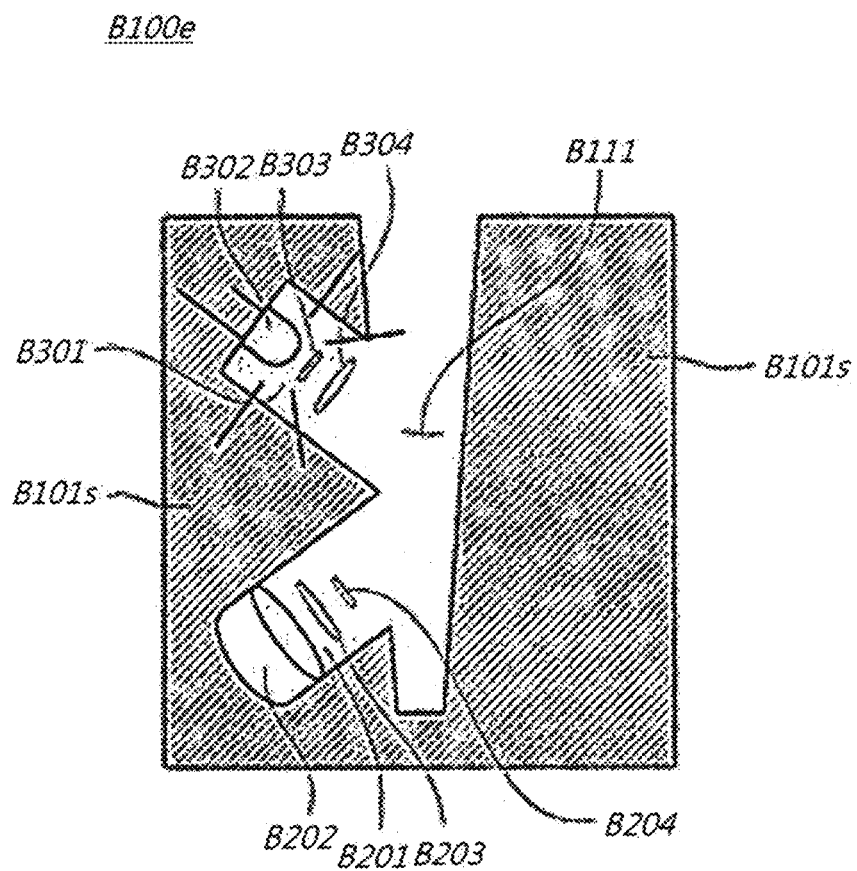
FIG. 28A shows an embodiment of an optical module of the present device using a support structure with a sliding recess.

FIG. 28A represents an embodiment of the optical module of the present invention. In the optical module B100e, the light source B302 and the photodetector B202 are installed in a support structure B101s having a recess B111 structure and the recess B111 provides a space for accommodating the reaction vessel.

The recess B111 may serve as a guide for guiding the movement of the reaction vessel. For example, in a horizontal support structure having recesses in a transverse direction, a plurality of optical units may be manufactured by installing a plurality of photodetectors in one plane of the support structure and then a plurality of light sources in appropriate positions of the same plane. The support structure installed with a plurality of optical units may be considered as one support structure. Alternatively, one part of the support structure in which the respective optical unit comprising one pair of the light source and the photodetector is installed may be considered as one support structure. In this case, the plurality of support structures may be provided as an assembly of support structures or a body combining support structures.

In this embodiment, the plurality of light sources may be different types of light sources from each other. Alternatively, the plurality of light sources may be the same type and excitation lights with different wavelengths of excitation light may be provided to the reaction vessel using different filters. The plurality of photodetectors may be the same type, and each of them may detect an emission light with a desirable wavelength filtered by a filter.

Figure 28B:
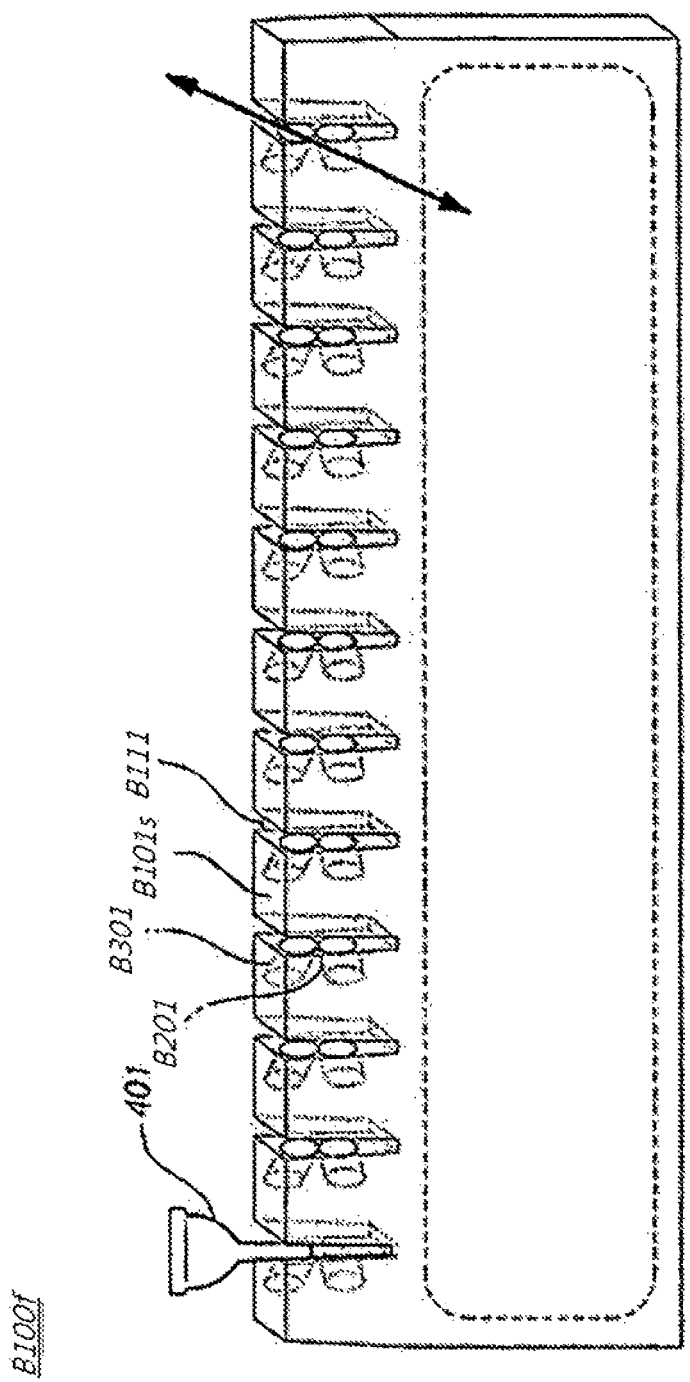
FIG. 28B shows an embodiment of an optical module of the present device using a support structure with a plurality of sliding recesses. The arrow indicates a moving direction of a reaction vessel 401.

According to an embodiment, the at least one optical module comprises two or more optical modules arranged in parallel (specifically, in vertically parallel) to provide one channel, each of the two or more optical modules comprises one light source and one photodetector, and the two or more optical modules provide excitation light of the same wavelength to the reaction vessel and detect emission light of the same wavelength from the reaction vessel (see FIG. 28B). Specifically, the number of optical modules providing one channel is at least 2, at least 4, at least 6, at least 8, at least 10, or at least 12. FIG. 28B represents another embodiment of the optical module B100f of the present invention. FIG. 28B shows a longitudinal support structure. In the longitudinal support structure B101s formed with a plurality of recesses B111 in the transverse direction, the accommodation hole for the photodetector B201 and the accommodation hole for the light source B301 are formed in the same plane of the support structure B101s, and the photodetector and the light source are installed therein, respectively. The reaction vessel 401 is inserted into the recess B111 and moves in the direction of the arrow. In an embodiment of the present invention, the device of the present invention is fabricated with two or more optical modules B100f comprising a plurality of optical units, which may be manufactured in the form of a cartridge (or cassette) providing one channel (see, FIG. 28B). If necessary, by adding an optical module that provides a desired other channel, a detection device having various channels may be provided.

According to an embodiment, the at least one optical module comprises two or more optical modules arranged in series to provide a plurality of channels, each of the plurality of channels comprises one optical module, the one optical module in each of the plurality of channels comprises one light source and one photodetector, and the two or more optical modules provide excitation lights of different wavelengths to the reaction vessel and detect emission lights of different wavelengths from the reaction vessel. For example, in the transverse support structure with recesses in the transverse direction, a plurality of photodetector-light source pairs that provide different channels may be installed in one plane of the support structure. Specifically, the number of optical modules providing the plurality of channels is at least 2, at least 4, or at least 6. In another embodiment, a plurality of photodetector-light source pairs that provide different channels may be used as a fabrication unit and a plurality of fabrication units may be fabricated in accordance with the number of reaction vessels. Specifically, the number of photodetector-light source pairs providing different channels is at least 2, at least 4, at least 6, at least 8, at least 10, or at least 12.

According to an embodiment, the at least one optical module comprises two or more optical modules arranged in parallel to provide one channel, a plurality of the two or more optical modules providing the one channel is arranged in series to provide a plurality of channels, each of the two or more optical modules in each of the plurality of channels comprises one light source and one photodetector, the two or more optical modules providing the one channel provide excitation light of the same wavelength to the reaction vessel and detect emission light of the same wavelength from the reaction vessel, and the two or more optical modules providing the plurality of channels provide excitation lights of different wavelengths to the reaction vessel and detect emission lights of different wavelengths from the reaction vessel. Specifically, the number of the optical modules providing the plurality of channels is at least 2, at least 4, or at least 6, and the number of the optical modules in each of the plurality of channels is at least 2, at least 4, at least 6, at least 8, at least 10 or at least 12. The device of the present invention may be manufactured as a plurality of optical modules comprising a plurality of optical units, and the plurality of optical modules provides different channels from each other. For example, a device having a plurality of optical modules B100f of FIG. 28B may correspond to this embodiment (see FIG. 30A). For example, in a rectangular parallelepiped support structure having a plurality of recesses in the transverse direction, the first to sixth optical modules may be successively installed in a longitudinal direction to provide the optical module of this embodiment. In this case, a plurality of light sources in each optical module providing one channel provides excitation light of the same wavelength to the reaction vessel, and a plurality of photodetectors detects emission light of the same wavelength; and the first to sixth optical modules proving the plurality of channels provide excitation lights of a different wavelengths to the reaction vessel and detect the emission lights of the different wavelengths.

A plurality of optical modules or optical units using even a single light source may be provided and each of the plurality of photodetectors may be installed in the accommodation hole for the photodetector formed in the support structure.

When a plurality of optical modules or optical units is used, a plurality of light sources may be provided in a light source-optical fiber manner. For example, in FIG. 28B, a single light source may be installed in the lower part of the support structure, and the plurality of optical fibers may be connected to the light source and installed in the accommodation hole for the light source. In addition, a single photodetector may be installed in the lower part of the support structure, and the plurality of optical fibers may be connected to the photodetector and be installed in the accommodation hole for the photodetector.

Figure 29:
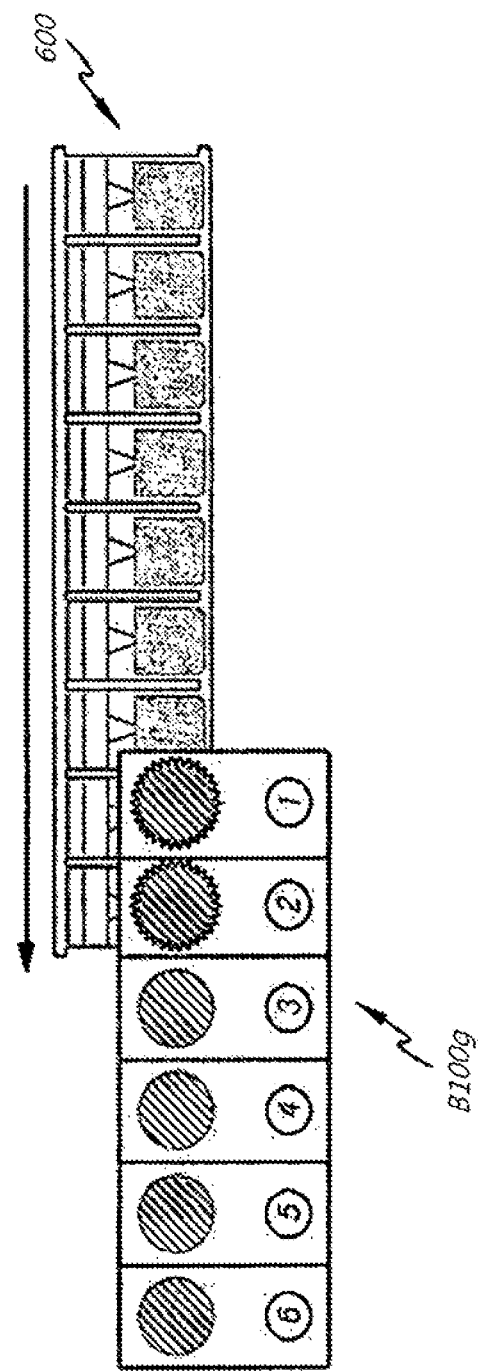
FIG. 29 is a schematic diagram showing the detection of fluorescence from a reaction vessel 600 in the present device including six optical modules B100g.

FIG. 29 is a schematic diagram showing the detection of fluorescence from a reaction vessel 600 in the device of the present invention including six optical modules B100g. As the reaction vessel 600 moves, the fluorescence detection is performed for each reaction tube. When the movement of the reaction vessel 600 allows each reaction tube to place in each of the six optical modules B100g, excitation light from the light source of the optical module B100g facing the front or rear plane of the reaction vessel 600 is provided to each reaction tube of the reaction vessel 600 and emission light generated from the reaction mixture of the reaction tube is detected by the photodetector facing the front or rear plane of the reaction vessel 600.

According to an embodiment, the optical unit or the photodetector is mounted in the support structure in a built-in manner. For example, the light source, the photodetector, the cable, and the processor may be incorporated in the support structure to provide the optical module. Alternatively, the optical unit or the photodetector may be separately formed from the support structure and may be then coupled to the support structure. For example, the light source and the photodetector may be detachably attached to the support structure via a connection means.

According to an embodiment of the present invention, the device further comprises a controller configured to adjust the intensity of the light source and the sensitivity of the photodetector. According to an embodiment of the present invention, the device further comprises a processor for communicating a signal to activate and deactivate the light source with the light source, and a signal processor for processing the signal detected by the photodetector. The controller and the processor may be functionally connected. Components (e.g., controllers and processors) that control the operation of the device of the present invention may be provided in the form of a process control block (PCB). For example, the controller and the processor may be installed at the lower part of the optical module (for example, the lower part of the optical module in FIG. 28B) including the support structure in which the optical unit is mounted.

According to an embodiment, the device of this invention further comprises an optical module base B501, and the optical module B100h is bound to the optical module base B501 in a detachable manner (see FIG. 30A). For example, the bottom of the optical module B100h comprising the support structure B101s in which the optical unit is mounted may be bound to the optical module base B501 in a detachable manner by using a binding means. For example, the optical module base B501 may be prepared to have a recess and the bottom of the optical module B100h may be prepared to have a structure for enabling to insert-in the recess such that the optical module B100h is mounted on the optical module base B501 in a detachable manner.

According to one embodiment, the support structure B101s has at least one sliding recess B111 formed such that when the reaction vessel 401, 150, 250 is inserted into a sliding recess, the reaction vessel is capable of being moved along the sliding recess in relative to the support structure (see, FIGS. 12-22, 28A-28B and 30A-30B). According to an embodiment, the number of the sliding recesses B111 formed in the support structure B101s is at least 2, at least 4, at least 6, at least 8, at least 10, or at least 12. According to an embodiment, the plane of the support structure B101s in which the accommodation hole for the photodetector B201 is formed is a lateral side of the at least one sliding recess of the support structure B111.

In this specification, a support structure having a sliding recess is named as "a sliding support structure", and an optical module comprising the sliding support structure is named as "a sliding optical module". In the sliding support structure B101s of the present invention, the recess B111 structure provides a space for accommodating the reaction vessel and serves as a guide for guiding the movement of the reaction vessel. In addition, the lateral side of the sliding recess B111 provides a location in which the optical unit is mounted. Therefore, the accommodation hole for the photodetector B201 and the accommodation hole for the light source B301 may be formed in the lateral side of the sliding recess B111, and the photodetector and the light source may be installed.

According to an embodiment of the present invention, the sliding recess B111 formed in the support structure B101s is a depression between two projections of the support structure B101s and the depression is a guide for movement of the reaction vessel (see FIGS. 12-22, 28A-28B and 30A-30B).

According to one embodiment, the accommodation hole for the photodetector B201 is formed in the lateral side of the sliding recess B111 (i.e., inner wall of the projection) (see FIGS. 28A-28B). According to one embodiment, the accommodation hole for the photodetector B201 and the accommodation hole for the light source B301 are formed in the lateral side of the sliding recess B111 (i.e., inner wall of the projection) (see FIGS. 28A-28B). According to one embodiment, the accommodation hole for the photodetector B201 and the accommodation hole for the light source B301 are formed in one same lateral side of the sliding recess B111 (i.e., inner wall of the projection) (see FIGS. 28A-28B). Alternatively, the accommodation hole for the photodetector B201 and the accommodation hole for the light source B301 are formed in two opposing lateral sides of the sliding recess B111 (i.e., inner wall of the projection). According to one embodiment, the sliding recess B111 may be tapered toward the bottom plane of the support structure B101s (see FIGS. 28A-28B).

In FIG. 30A, the device of the present invention comprises six optical modules B100h, which are mounted on the optical module base B501 in a detachable manner. The six optical modules B100h comprises the support structures B101s in which the sliding recess B111 is formed. The numbers in circles on the support structure B101s in the longitudinal direction represent six optical modules, and the sliding recesses B111 formed in the support structure of each optical module are connected to each other such that the reaction vessel moves along the sliding recess B111. The six optical modules B100h in FIG. 30A may be provided by arranging adjacently six optical modules each providing one channel as shown in B100f of FIG. 28B. The six adjacent optical modules B100h provide six different channels, provide excitation lights of different wavelengths to the reaction vessel and detect emission lights of different wavelengths from the reaction vessel. Each of the six optical modules B100h may comprise at least 2, at least 4, at least 6, at least 8, at least 10, or at least 12 optical units. When each of the six optical modules B100h includes 12 optical units (not shown), the 12 optical units include 12 light sources (not shown) and 12 photodetectors (not shown), and the 12 light sources provide excitation light of the same wavelength to the reaction vessel and the 12 photodetectors detect the same wavelength of emission light. Each optical unit may have the same arrangement as the optical unit shown in FIG. 28A.

The device of the present invention may be used for all reactions in which a fluorescence signal is changed as a reaction progress. According to one embodiment of the present invention, the device of this invention is used for analyzing a nucleic acid amplification reaction, specifically, a real-time PCR device. For example, the device of the present invention may be used to analyze in real-time manner the following reactions in which a fluorescence signal is changed with nucleic acid amplification: PTO cleavage AND extension (PTOCE) method (WO 2012/096523), PTO Cleavage and Extension-Dependent Signaling Oligonucleotide Hybridization (PCE-SH) method (WO 2013/115442), PTO Cleavage and Extension-Dependent Non-Hybridization (PCE-NH) method (WO 2014/104818), PTO Cleavage and Extension-Dependent Cleavage (PCEC) method (WO 2012/134195), PO Cleavage and Hybridization (POCH) method (WO2012/150835), TaqMan method (U.S. Pat. Nos. 5,210,015 and 5,538,848), Molecular Beacon method (Tyagi et al., Nature Biotechnology, 14:303 (1996)), Scorpion method (Whitcombe et al., Nature Biotechnology 17:804-807 (1999)), Sunrise or Amplifluor method [(Nucarenko et al., 2516-2521 Nucleic Acids Research, 25(12):2516-2521(1997); and U.S. Pat. No. 6,117,635), Lux method (U.S. Pat. No. 7,537,886), CPT (Duck P, Biotechniques, 9:142-148(1990)), LNA method (U.S. Pat. No. 6,977,295), Plexor method (Sherrill CB, et al., Journal of the American Chemical Society, 126:4550-4556 (2004)), Hybeacons method (DJ French, et al., Molecular and Cellular Probes (2001) 13, 363-374 and U.S. Pat. No. 7,348,141), Method using dual labeled self-quenched probe (U.S. Pat. No. 5,876,930) and Method using hybridization probe (Bernard PS, et al., Clin Chem 2000, 46, 147-148).

Figure 31A:
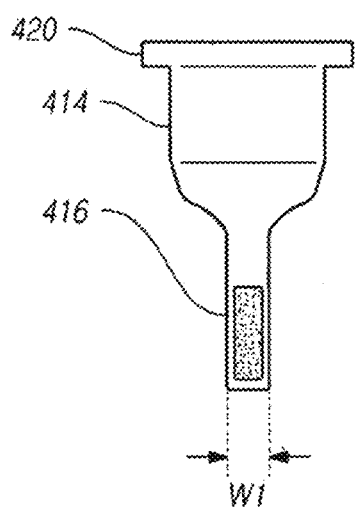
FIGS. 31A to 31C are a side view, a front view, and a plan view of a reaction tube for a nucleic acid amplification according to still another embodiment, respectively.
Figure 31B:
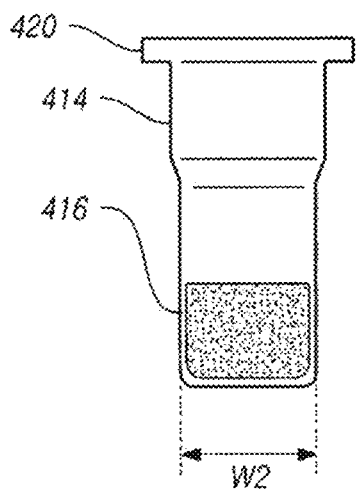
Figure 31C:
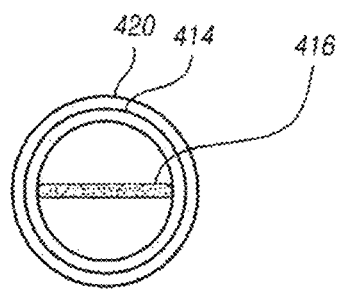

FIGS. 31A to 31C are a side view, a front view, and a plan view of a tube according to still another embodiment, respectively.

Referring to FIGS. 31A to 31C, a tube 400 according to still another embodiment may be a reaction tube for a nucleic acid amplification for use in the apparatus for performing a nucleic acid amplification. The reaction tube 400 for a nucleic acid amplification may be a unit of a reaction container that forms the above mentioned reaction vessel 150, 250, 350, but not limited thereto.

The reaction tube 400 for a nucleic acid amplification may comprise an upper part 414 and a lower part 416 configured to accommodate a reaction mixture for amplifying a nucleic acid.

The reaction tube 400 for a nucleic acid amplification may comprise a rim 420 connected to the upper part 414. As Illustrated in FIGS. 31A to 31C, the rim 420 may protrude outward along the periphery of the reaction tube 400. However, without being limited thereto, the rim 420 may be a shape that is not protruded outward or is inwardly recessed.

The upper part 414 may have a hollow-cylindrical shape or hollow-polygonal column shape, but may have another shape without being limited thereto. As illustrated in FIGS. 31A to 31C, the lower part 416 is positioned below the upper part 414, and is fluidically connected to the upper part 414. The lower part 416 has a flattened shape, including (i) front and rear planes each having a flat face, (ii) side planes narrower than the front plane, and (iii) a bottom plane. The flat face of each of the front and rear planes is thermoconductively in contact with the block used for the a nucleic acid amplification reaction which is positioned at the lower part 416.

The reaction tube 400 for a nucleic acid amplification may have a volume that may accommodate the reaction mixture for amplifying a nucleic acid of 1500 μl or less, 1000 μl or less, 800 μl or less, 700 μl or less, 500 μl or less, 400 μl or less, 300 μl or less, 200 μl or less, or 100 μl or less.

In addition, the lower part 416 of the reaction tube 400 for a nucleic acid amplification may have a volume that may accommodate the reaction mixture for amplifying a nucleic acid of 1 μl or more, 3 μl or more, or 5 μl or more, and of 100 μl or less, 50 μl or less, 40 μl or less, 30 μl or less, 20 μl or less, or 10 μl or less.

In the lower part 416 of the reaction tube 400 for a nucleic acid amplification, each of the front and rear planes has wholly a flat face, or has a flat face at least in the portion in which the reaction mixture for amplifying a nucleic acid is accommodated.

The side planes of the lower part 416 of the reaction tube 400 for a nucleic acid amplification are narrower than the front plane of the lower part 416. Specifically, the width W1 of the side planes of the lower part 416 of the reaction tube 400 may be 80% or less, 70% or less, 50% or less, 40% or less, 30% or less, 25% or less, 20% or less, 15% or less, or 10% or less of the width W2 of the front plane of the lower part 416.

Each of the width and height of the front plane of the lower part 416 may independently have a dimension of 2 mm or more or 3 mm or more, and 15 mm or less, 10 mm or less, or 5 mm or less. Specifically, each of the width and height of the front plane of the lower part 416 may independently have a dimension of 3 mm or more and 15 mm or less, or 3 mm or more and 10 mm or less.

In addition, the width of the side planes of the lower part 416 may have a dimension of 1 mm or more, 2 mm or more, or 3 mm or more, and 10 mm or less, 7 mm or less, or 5 mm or less. Specifically, the width of the side planes of the lower part 416 may have a dimension of 1 mm or more and 7 mm or less.

The height of the front plane of the lower part 416 may be 300% or less, 200% or less, 150% or less, 100% or less, 50% or less, or 30% or less of the width of the front plane of the lower part 416.

As the reaction tube 400 for a nucleic acid amplification has the flattened lower part 416, the reaction tube 400 for a nucleic acid amplification tube may be inserted into the sliding recess 122, 132, 222, 322 of the above-mentioned block 120, 130, 220, 320 (specifically, the above-mentioned block 120, 130, 220, 320 and the optical module 100h), the front plane of the lower part 416 may come in contact with the inner plane of the sliding recess 122, 132, 222, 322.

The first width W1 of the side planes of the lower part 416, which do not come in contact with the inner plane of each of the sliding recesses 122, 132, 222, 322, and so on, may be minimized, and the second width W2 of the front plane of the lower part 416, which comes in contact with the inner plane of each of the siding recesses 122, 132, 222, 322, and so on, may be maximized. Thus, the contact surface of the reaction tube with the blocks may be maximized. Consequently, it is possible to improve either a heating rate or a cooling rate.

While the lower part 416 may have a square column shape as illustrated in FIGS. 31A to 31C, the width W2 of the front plane of the lower part 416 may be narrowed or widened toward the bottom plane. In addition, the width W2 of the front plane of the lower part 416 may be: narrowed, widened, narrowed and then widened, or widened and then narrowed.

At least a portion of the side planes, the front plane, the rear plane, or the bottom plane of the lower part may include a round shape. According to one embodiment, the side planes, the front plane, the rear plane, or the bottom plane may include a convex or concave shape.

The reaction tube 400 for a nucleic acid amplification may be made of a transparent material such that light, which is irradiated from the outside, is capable of penetrating the reaction tube 400 for a nucleic acid amplification. The reaction tube 400 for a nucleic acid amplification may be made of a material that is capable of being autoclaved or that is excellent in thermal conduction efficiency. For example, silicon or polypropylene may be used.

The reaction tube 400 for a nucleic acid amplification may be manufactured in such a manner that at least one of the front plane, the side planes, and the bottom plane of the upper part 414 or the lower part 416 is thick in order to prevent undesirable light or fluorescence other than fluorescence emitted from a label or light irradiated for detecting a signal from penetrating the reaction tube 400 (light leakage phenomenon). Specifically, the tube 400 may be fabricated in such a manner that the side planes are thick. The thick structure may also serve as a frame for maintaining the shape of the tube 400.

The reaction tube 400 for a nucleic acid amplification may be manufactured in such a manner that at least one of the front plane, the side planes, and the bottom plane of the upper part 414 or the lower part 416 is opaque in order to prevent undesirable light or fluorescence other than fluorescence emitted from a label or light irradiated for detecting a signal from penetrating the reaction tube 400 for a nucleic acid amplification. Specifically, the tube may be fabricated in such a manner that the side planes are opaque. Unless the side planes are opaque, fluorescence generated from a tube next to the tube of which the fluorescence measurement is in progress may affect the result of the measurement. Alternatively, except for the top plane of the reaction tube into which the reaction mixture is introduced, all the planes of the tube may be fabricated to be opaque.

Figure 32A:
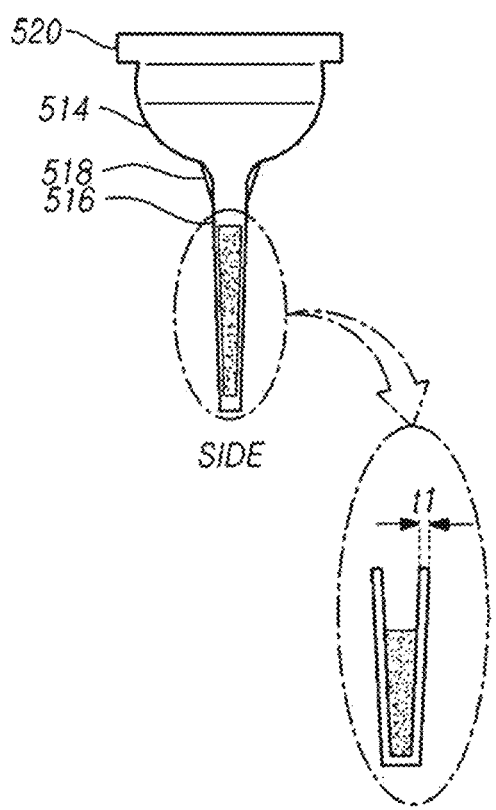
FIGS. 32A to 32C are a side view, a front view, and a plan view of a reaction tube for a nucleic acid amplification according to still another embodiment.
Figure 32B:
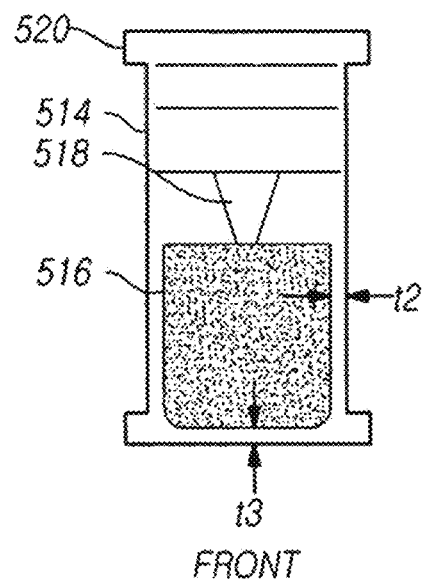
Figure 32C:
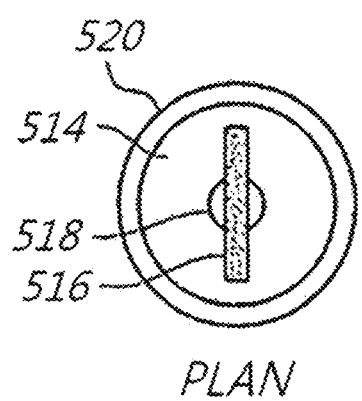

FIGS. 32A to 32C are a side view, a front view, and a plan view of a reaction tube for a nucleic acid amplification according to still another embodiment.

Referring to FIGS. 32A to 32C, in a reaction tube 500 for a nucleic acid amplification according to still another embodiment, side planes of the lower part 516 may be tapered toward the bottom plane, and each of the sliding recess 122, 132, 222, 322, and so on may be tapered toward the bottom plane to accommodate the lower part 516.

The reaction tube 500 for a nucleic acid amplification may comprise a tip guide 518 configured to guide the insertion of a dispensing tip from the upper part 514 to the lower part 516. When dispensing a sample into the tube 500 for a nucleic acid amplification using a dispensing tip (e.g., a dispenser), the dispensing tip may be inserted into the tip guide 518 and then the sample may be easily dispensed into the lower part 516.

The tip guide 518 extends from the upper part 514 to a predetermined position in the lower part 516. In the plan view, the upper part 514 may have a circular or oval shape, and the tip guide 518 may have a circular or oval shape, but not limited thereto.

The thickness t1 in the front plane and thickness t2 in the bottom plane when viewed from a side of the lower part 516 may be substantially equal to each other as illustrated in FIGS. 32A and 32B, but is not limited thereto. Through this, the front plane and the bottom plane of the lower part 516 may be simultaneously in contact with the inner plane of the sliding recess 122, 132, 222, 322, or the like to exchange heat.

The thickness t1 in the front plane of the lower part 516 may be made to be thicker than the thickness t3 in the bottom plane, but is not limited thereto.

Figure 33:
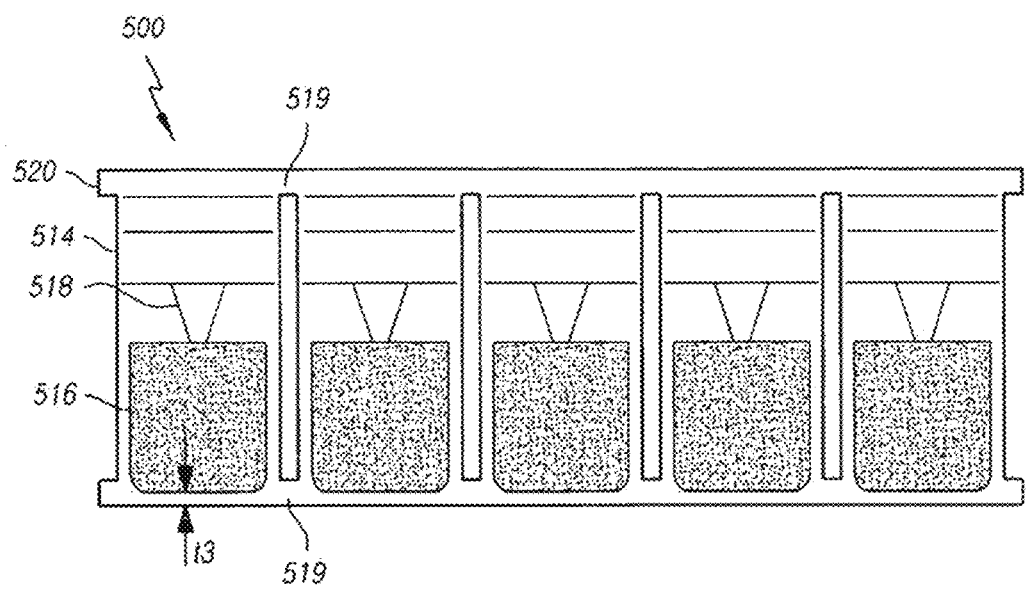
FIG. 33 is a sectional view illustrating a reaction vessel for a nucleic acid amplification according to still another embodiment.

FIG. 33 is a sectional view illustrating a reaction vessel for a nucleic acid amplification according to still another embodiment.

Referring to FIG. 33, a reaction vessel 600 for use in a apparatus for a nucleic acid amplification according to still another embodiment may comprise two or more reaction containers. When the reaction vessel comprises two or more reaction containers, it may include not only a case in which the two or more containers are physically directly connected to each other, but also a case in which the two or more containers are physically indirectly connected through connection means (e.g., a holder). When a plurality of PCR tubes or a plurality of strip tubes is coupled to a holder, it is an implemented example of the reaction vessel to which two or more reaction containers are indirectly connected. The reaction containers may be the tubes 400 or the tubes 500 illustrated in FIGS. 31A to 31C or FIGS. 32A to 32C. A reaction vessel 600 for a nucleic acid amplification according to still another embodiment may have two or more reaction containers 500 which may be: coupled to each other, separated from each other, or arranged in a row.

Each of the reaction containers 500 for a nucleic acid amplification may comprise an upper part 514 and a lower part 516 configured to accommodate a reaction mixture for amplifying a nucleic acid. The two or more reaction containers 500 may be sequentially connected to each other, and may form an integrated body. In addition, the two or more containers 500 may be formed in a regular arrangement on the reaction vessel, and may form an integrated body.

As illustrated in FIG. 33, in two or more reaction containers 500, at least one of the rims 520, the upper parts 514, and the lower parts 516 thereof may be connected to each other.

The width of the connection parts 519 when viewed from a side plane may be fabricated to be sufficiently thick such that the connection parts 519 are not separated by external force, but is not limited thereto.

Figure 34:
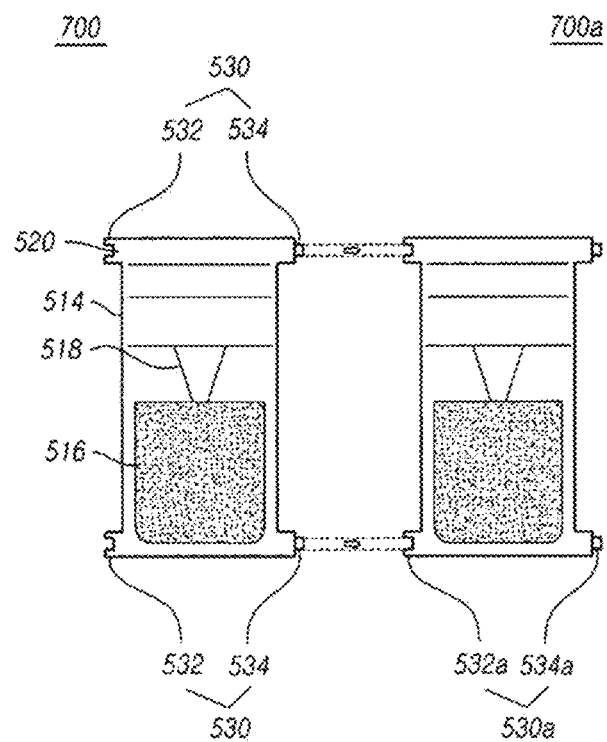
FIG. 34 is a sectional view illustrating a reaction vessel for a nucleic acid amplification according to still another embodiment.

FIG. 34 is a sectional view illustrating a reaction tube for a nucleic acid amplification according to still another embodiment.

Referring to FIG. 34, reaction tubes 700, 700a according to still another embodiment comprise upper and lower parts 514, 516 that are positioned inside each of the reaction tubes 700, 700a and are fluidically connected each other like the reaction tube 500 illustrated in FIGS. 32A to 32C, a tip guide 518 extending from the upper part 514 to the lower part 516, and a rim 520 integrally connected to the upper part 514.

The reaction tube 700 according to still another embodiment may further comprise a connection part 530 configured to connect the reaction tube 700 to another reaction tube 700a.

The connection part 530 may be positioned on any one of the upper part 514, the lower part 516, and the rim 520.

For example, as illustrated in FIG. 34, the connection part 530 may be arranged on each of the lower part 516 and the rim 520.

Each connection part 530 may comprise a concave portion 532 and a convex portion 534. The concave portion 532 and the convex portion 534 may interconnect one reaction tube 700 and another reaction tube 700a through concave-convex coupling or female-male coupling with the convex portion 534 of a reaction tube 700 and the concave portion 532a of another reaction tube 700a.

While it has been described that the connection part 530 illustrated in FIG. 34 comprise both the concave portion 532 and the convex portion 534 on one reaction tube 700, the connection part 530 of one reaction tube 700 may comprise only the concave portion, and the connection part 530a of another reaction tube 700a may comprise only the convex portion. In addition, while it has been described that in the connection part 530, the concave portion 532 is only positioned in one direction and the convex portion 534 is only positioned in the other direction, both the concave portion and the convex portion may be positioned in a specific direction. The connection part 530 may have various shapes, and may be connected through various methods, such as a fitting method or a locking method.

Figure 35:
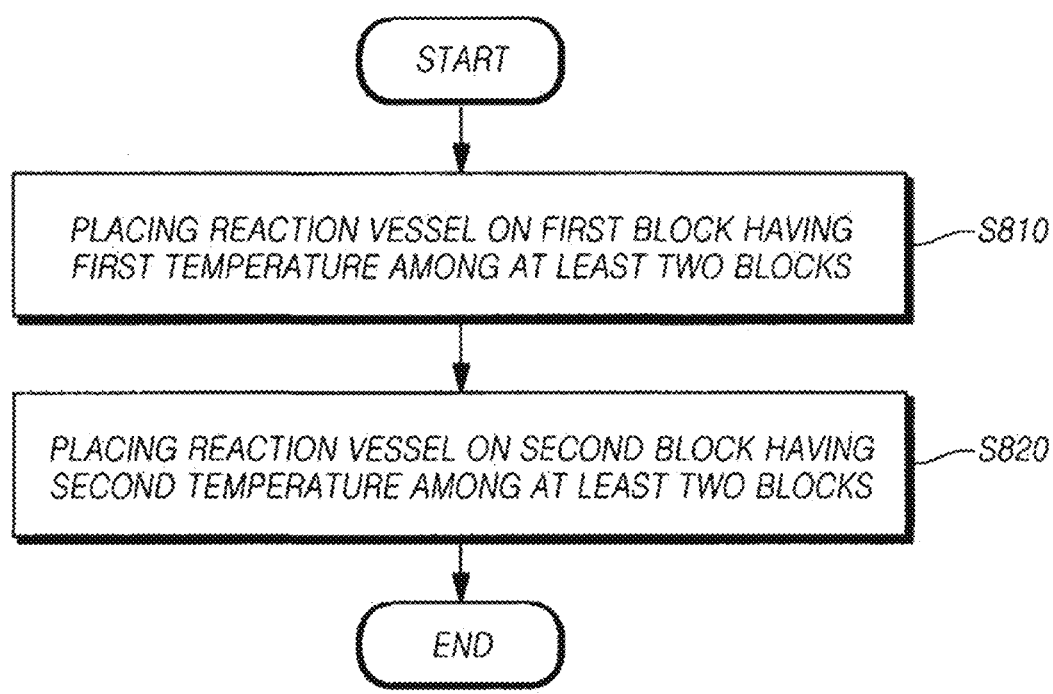
FIG. 35 is a flowchart illustrating a method for a nucleic acid amplification according to still another embodiment.

FIG. 35 is a flowchart illustrating a method for a nucleic acid amplification according to another embodiment.

Referring to FIG. 35, a method 800 for a nucleic acid amplification according to still another embodiment may comprise: (i) placing at a first time a reaction vessel containing a reaction mixture on a first block having a first temperature among at least two blocks such that the reaction vessel is inserted into the sliding recess of the first block; wherein the at least two blocks have at least one sliding recess formed such that when the reaction vessel is inserted into a sliding recess, the reaction vessel is capable of being moved along sliding recesses between the at least two blocks; wherein the at least two blocks are configured to be subjected to independent temperature control; and (ii) placing at a second time the reaction vessel on a second block having a second temperature such that the reaction vessel is inserted into a sliding recess of the second block.

According to one embodiment, the method is performed by repeating the steps (i) and (ii). For example, the number of repetitions of the steps (i) and (ii) may be 2-100 times, 2-80 times, 2-60 times, 2-50 times, 2-40 times, 5-100 times, 5-80 times, 5-60 times, 5-50 times, 5-40 times, 10-100 times, 10-80 times, 10-60 times, 10-50 times, 10-40 times, 20-100 times, 20-80 times, 20-60 times, 20-50 times or 20-40 times.

In the step (i) (S810) and step (ii) (S820), the reaction vessel may be moved between the first and second blocks along the sliding recess of the first and second blocks to be positioned on one of the first and second blocks.

In the step (i) (S810) and step (ii) (S820), one of the first and second blocks may be moved along the reaction vessel inserted so as to allow the reaction vessel to be positioned in one of the first and second blocks.

According to one embodiment, the temperature of the first block is changed into a third temperature at the second time, and the method further comprises placing at a third time the reaction vessel on the first block having the third temperature such that the reaction vessel is inserted into the sliding recess of the first block.

FIG. 36 is a flowchart illustrating a method for a nucleic acid amplification according to yet another embodiment.

Referring to FIG. 36, a method 900 for a nucleic acid amplification according to yet another embodiment may comprise: (i) placing at a first time a reaction vessel containing a reaction mixture on a first block having a first temperature among at least two blocks such that the reaction vessel is inserted into a sliding recess of the first block; wherein the at least two blocks have at least one sliding recess formed such that when the reaction vessel is inserted into a sliding recess, the reaction vessel is capable of being moved along sliding recesses between the at least two blocks; wherein the at least two blocks are configured to be subjected to independent temperature control; (ii) placing at a second time, the reaction vessel on a second block having a second temperature such that the reaction vessel is inserted into a sliding recess of the second block; wherein the temperature of the first block is changed into a third temperature at the second time; and (iii) placing at a third time the reaction vessel on the first block having the third temperature such that the reaction vessel is inserted into the sliding recess of the first block.

According to one embodiment, the method is performed by repeating the steps (i), (ii) and (iii). For example, the number of repetitions of the steps (i), (ii) and (iii) may be 2-100 times, 2-80 times, 2-60 times, 2-50 times, 2-40 times, 5-100 times, 5-80 times, 5-60 times, 5-50 times, 5-40 times, 10-100 times, 10-80 times, 10-60 times, 10-50 times, 10-40 times, 20-100 times, 20-80 times, 20-60 times, 20-50 times or 20-40 times.

In the step (i) (S910), step (ii) (S920), and step (iii) (S930), the reaction vessel may be moved between the first and second blocks along the sliding recess of the first and second blocks to be positioned on one of the first and second blocks.

In the step (i) (S910), step (ii) (S920), and step (iii) (S930), one of the first and second blocks may be moved along the reaction vessel inserted so as to allow the reaction vessel to be positioned in one of the first and second blocks.

While embodiments have been described with reference to the drawings, the present invention is not limited thereto.

For example, the number of blocks is three, and the three blocks may be positioned to be adjacent to each other. At this time, the reaction vessel may be moved along the sliding recess of the blocks to be positioned on any of the three blocks.

That is, at a first time, a reaction vessel containing a sample may be placed on a first block having a first temperature such that the reaction vessel is inserted into the sliding recess of the first block; wherein the three blocks have at least one sliding recess formed in a direction such that when the reaction vessel is inserted into the sliding recess, the reaction vessel is capable of being moved along the sliding vessel; wherein the three blocks are configured to be subjected to independent temperature control.

At a second time, among the blocks, the reaction vessel may be placed on a second block having a second temperature such that the reaction vessel is inserted into the sliding recess of the second block.

At a third time, among the blocks, the reaction vessel may be placed on a third block having a third temperature such that the reaction vessel is inserted into the sliding recess of the third block.

In the first step, second step, and third step, the reaction vessel may be moved among the three blocks along the sliding recesses of the first to third blocks to be positioned on one of the first to third blocks.

As described above, according to the present invention, the structure for a precise temperature control may be simple, and a time required for performing an entire nucleic acid amplification reaction may be short.

According to one embodiment, the method further comprises detecting emission light from the reaction vessel by placing the reaction vessel on a fluorescence detection device such that the reaction vessel is inserted into a sliding recess of a support structure of the fluorescence detection device.

According to one embodiment, the fluorescence detection device comprises at least one optical module, comprising: (a) a support structure; (b) an accommodation hole for a photodetector formed in one plane of the support structure, and having an optically open structure toward a direction in which the reaction vessel is located; and (c) an optical unit comprising: (c-1) a light source for providing excitation light; and (c-2) a photodetector configured to be positioned in the accommodation hole for the photodetector so as to allow the photodetector to be located in an emission light path from the reaction vessel.

According to another aspect of the present invention, the present invention provides a computer-readable recording medium that stores instructions to implement a processor for executing a method for a nucleic acid amplification.

The method comprises the following steps: (i) placing at a first time a reaction vessel containing a reaction mixture on a first block having a first temperature among at least two blocks such that the reaction vessel is inserted into the sliding recess of the first block; wherein the at least two blocks have at least one sliding recess formed such that when the reaction vessel is inserted into a sliding recess, the reaction vessel is capable of being moved along sliding recesses between the at least two blocks; wherein the at least two blocks are configured to be subjected to independent temperature control; and (ii) placing at a second time the reaction vessel on a second block having a second temperature such that the reaction vessel is inserted into a sliding recess of the second block.

According to another aspect of the present invention, the present invention provides a computer program stored in a computer-readable recording medium to implement a processor for executing a nucleic acid amplification method.

The method comprises the following steps: (i) placing at a first time a reaction vessel containing a reaction mixture on a first block having a first temperature among at least two blocks such that the reaction vessel is inserted into a sliding recess of the first block; wherein the at least two blocks have at least one sliding recess formed such that when the reaction vessel is inserted into a sliding recess, the reaction vessel is capable of being moved along sliding recesses between the at least two blocks; wherein the at least two blocks are configured to be subjected to independent temperature control; and (ii) placing at a second time the reaction vessel on a second block having a second temperature such that the reaction vessel is inserted into a sliding recess of the second block.

The recording medium and the computer program of the present invention relate to a method for a nucleic acid amplification using the above-described apparatus of the present invention, and the common contents thereof will be omitted in order to avoid excessively complicating the specification due to repeated descriptions.

The method of the present invention is executed in a processor, which may be a process that is provided to a stand-alone computer, a network-attached computer, or a data acquisition device, such as a real time PCR device.

The computer-readable recording medium may comprise various storage mediums known in the art (e.g., a CD-R, a CD-ROM, a DVD, a flash memory, a floppy disc, a hard drive, a portable HDD, a USB, a magnetic tape, a mini-disc, a non-volatile memory card, an EEPROM, an optical disc, an optical storage medium, a RAM, a ROM, a system memory, and a web server), but is not limited thereto.

Instructions to implement a processor for executing the present invention may be comprised in a logic system. The instructions may be provided as a software recording medium (e.g., a portable HDD, a USB, a floppy disc, a CD, or a DVD), but may be downloaded and may be stored in a memory module (e.g., a hard drive or other memories, such as a local or attached RAM and a ROM). Computer codes to execute the present invention may be executed by various coding languages, such as C, C++, Java, Visual Basic, VBScript, JavaScript, Perl, and XML. In addition, various languages and protocols may be used for internal and external storage and delivery of signals and commands according to the present invention.

The computer processor may be constructed to execute all the above-described performances by one processor. Alternatively, a processor unit may be constructed such that multiple processors execute each performance.

In the foregoing, specific parts of the present invention have been described in detail. However, it is evident to a person ordinarily skilled in the art that the specific techniques are merely implemented examples, and the scope of the present invention is not limited thereby. Accordingly, the practical scope of the present invention is defined by the accompanying claims and the equivalents thereof.

Even if it was described above that all of the components of an embodiment of the present invention are coupled as a single unit or coupled to be operated as a single unit, the present invention is not necessarily limited to such an embodiment. That is, at least two elements of all structural elements may be selectively joined and operate without departing from the scope of the present invention. Further, all structural elements may be implemented in independent hardware respectively, but some or all of the structural elements may be selectively combined and implemented in computer programs which have a program module performing functions of some elements or all elements which are combined in one or more pieces of hardware. Codes and code segments forming the computer program can be easily conceived by an ordinarily skilled person in the technical field of the present invention. Such a computer program may implement the embodiments of the present invention by being stored in a computer readable storage medium, and being read and executed by a computer. A magnetic recording medium, an optical recording medium, or the like may be employed as the storage medium of a computer program.

In addition, since terms, such as "including," "comprising," and "having" mean that one or more corresponding components may exist unless they are specifically described to the contrary, it shall be construed that one or more other components can be included. All the terms that are technical, scientific or otherwise agree with the meanings as understood by a person skilled in the art unless defined to the contrary. Common terms as found in dictionaries should be interpreted in the context of the related technical writings not too ideally or impractically unless the present invention expressly defines them so.

Although a preferred embodiment of the present invention has been described for illustrative purposes, those skilled in the art will appreciate that various modifications, additions and substitutions are possible, without departing from the scope and spirit of the invention as disclosed in the accompanying claims. Therefore, the embodiments disclosed in the present invention are intended to illustrate the scope of the technical idea of the present invention, and the scope of the present invention is not limited by the embodiment. The scope of the present invention shall be construed on the basis of the accompanying claims in such a manner that all of the technical ideas included within the scope equivalent to the claims belong to the present invention.

What is claimed is:

1. An apparatus for performing a nucleic acid amplification reaction, comprising:
   (i) a main body;
   (ii) at least two blocks positioned on the main body and each having at least one sliding recess formed such that when a reaction vessel is inserted into a sliding recess, the reaction vessel is capable of being moved along sliding recesses between the at least two blocks, the at least two blocks being configured to be subjected to independent temperature control; and
   (iii) a moving module configured to move the at least two blocks and/or the reaction vessel such that the reaction vessel is moved along the sliding recesses relative to the at least two blocks.

2. The apparatus according to claim 1, wherein the at least two blocks are physically connected to or separated from each other.

3. The apparatus according to claim 1, wherein the moving module is configured such that the reaction vessel is moved along the sliding recesses between the at least two blocks or at least one of the at least two blocks is moved along the reaction vessel inserted so as to allow the reaction vessel to be positioned in one of the at least two blocks.

4. The apparatus according to claim 1, wherein the moving module comprises:
   a power unit configured to provide power; and
   a power transmission and driving unit coupled to the at least two blocks and/or the reaction vessel, and configured to move the at least two blocks and/or the reaction vessel using the power.

5. The apparatus according to claim 1, wherein the apparatus further comprises a reaction vessel holder configured to accommodate the reaction vessel; and wherein the moving module comprises a power unit configured to provide power; and a power transmission and driving unit coupled to the reaction vessel holder and configured to move the reaction vessel holder using the power.

6. The apparatus according to claim 1, wherein the reaction vessel comprises two or more reaction containers, which are coupled to each other, separated from each other, or arranged in a row; wherein the two or more reaction containers have a tube form comprising: (i) an upper part having a hollow-cylindrical shape or hollow-polygonal column shape; and (ii) a lower part configured to accommodate a reaction mixture for amplifying a nucleic acid, and fluidically connected to the upper part, the lower part having a flattened shape including front and rear planes each having a flat face, side planes narrower than the front plane, and a bottom plane, wherein the flat face of each of the front and rear planes is thermoconductively in contact with the at least two blocks.

7. The apparatus according to claim 1, wherein the apparatus further comprises a fluorescence detection device for reaction analysis comprising at least one optical module comprising:
   (a) a support structure;
   (b) an accommodation hole for a photodetector formed in one plane of the support structure, and having an optically open structure toward a location in which the reaction vessel is positioned; and
   (c) an optical unit comprising:
      (c-1) a light source for providing excitation light; and
      (c-2) a photodetector configured to be positioned in the accommodation hole for the photodetector such that the photodetector is arranged in an emission light path from the reaction vessel.

8. The apparatus according to claim 7, wherein the support structure has at least one sliding recess formed such that when the reaction vessel is inserted into a sliding recess, the reaction vessel is capable of being moved along sliding recesses between the support structure and the at least two blocks.

9. The apparatus according to claim 7, wherein the fluorescence detection device is located between the at least two heat blocks.

* * * * *